US009624309B2

(12) United States Patent
Liu et al.

(10) Patent No.: US 9,624,309 B2
(45) Date of Patent: Apr. 18, 2017

(54) MONOSPECIFIC AND MULTISPECIFIC ANTIBODIES AND METHOD OF USE

(75) Inventors: Bing Liu, Richmond, CA (US); David Light, San Mateo, CA (US); Zhuozhi Wang, Burlingame, CA (US); Douglas Schneider, Lafayette, CA (US)

(73) Assignee: BAYER INTELLECTUAL PROPERTY GmbH, Monheim (DE)

( * ) Notice: Subject to any disclaimer, the term of this patent is extended or adjusted under 35 U.S.C. 154(b) by 1266 days.

(21) Appl. No.: 12/671,942

(22) PCT Filed: Aug. 16, 2008

(86) PCT No.: PCT/EP2008/006750
§ 371 (c)(1),
(2), (4) Date: Feb. 22, 2010

(87) PCT Pub. No.: WO2009/021754
PCT Pub. Date: Feb. 19, 2009

(65) Prior Publication Data
US 2011/0229476 A1 Sep. 22, 2011

Related U.S. Application Data

(60) Provisional application No. 60/955,913, filed on Aug. 15, 2007.

(51) Int. Cl.
*A61K 39/395* (2006.01)
*C07K 16/46* (2006.01)
*A61K 47/48* (2006.01)
*C07K 16/30* (2006.01)
*C07K 16/36* (2006.01)
*A61K 39/00* (2006.01)

(52) U.S. Cl.
CPC .......... *C07K 16/468* (2013.01); *A61K 47/484* (2013.01); *A61K 47/48407* (2013.01); *A61K 47/48453* (2013.01); *A61K 47/48476* (2013.01); *A61K 47/48484* (2013.01); *A61K 47/48569* (2013.01); *A61K 47/48638* (2013.01); *C07K 16/3069* (2013.01); *C07K 16/3076* (2013.01); *C07K 16/36* (2013.01); *A61K 2039/505* (2013.01); *C07K 2317/31* (2013.01); *C07K 2317/56* (2013.01); *C07K 2317/64* (2013.01)

(58) Field of Classification Search
None
See application file for complete search history.

(56) References Cited

U.S. PATENT DOCUMENTS 6,207,804 B1 * 3/2001 Huston et al. ............. 530/387.3
2004/0038316 A1 * 2/2004 Kaiser .................... C07H 21/00
435/7.2

FOREIGN PATENT DOCUMENTS

| WO | WO 01/95942 | | 12/2001 |
|----|----|----|----|
| WO | WO03018616 | * | 3/2003 |
| WO | 2003080672 A1 | | 10/2003 |
| WO | 2004058820 A2 | | 7/2004 |
| WO | WO/2007/024715 | * | 3/2007 |
| WO | WO 2007/024715 | | 3/2007 |

OTHER PUBLICATIONS

Doronina et al. (Nature Biotechnology, vol. 21, No. 7, pp. 778-941, 2003).*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Carter, "Potent Antibody Therapeutics by Design," Nature Reviews, Immunology, vol. 6, pp. 343-357; Apr. 7, 2006.
Hamblett et al, Abstract #610, "SGN-35, an Anti-CD30 Antibody-Drug Conjugate, Exhibits Potent Antitumor Activity for the Treatment of CD30(+) Malignancies," Blood 106, No. 11, p. 181A, Dec. 13, 2005.
Wu et al., "Simultaneous targeting of multiple disease mediators by a dual-variable-domain immunoglobulin," Nature Biotechnology, vol. 25, No. 11, pp. 1290-1297, Nov. 2007.
Little et al., "Of Mice and Men: hybridoma and recombinant antibodies," Immunology Today, vol. 21, No. 8, pp. 364-370, Aug. 1, 2000.
Trail et al., "Monoclonal antibody drug immunoconjugates for targeted treatment of cancer," Cancer Immunology and Immunotherapy, vol. 52, No. 5, pp. 328-337, May 1, 2003.
Denny et al., "Prodrug strategies in cancer therapy," European Journal of Medicinal Chemistry 36, 577-95, 2001.
Donaldson et al., "Design and development of masked therapeutic antibodies to limit off-target effects: Application to anti-EGFR antibodies," Cancer Biology and Therapy 8, 2147-52, 2009.
Extended European Search Report for European application 12172679.4, 8 pages, Nov. 8, 2012.
International Search Report for PCT/EP2008/006750, 6 pages, Feb. 19, 2009.
Jain et al., "Engineering antibodies of clinical applications," Trends in Biotechnology 25, 307-16, 2007.
Oran et al., "Site-specific targeting of antibody activity in vivo mediated by disease-associated proteases," Journal of Controlled Release 161, 804-12, 2012.

(Continued)

*Primary Examiner* — Laura B Goddard
*Assistant Examiner* — Meera Natarajan
(74) *Attorney, Agent, or Firm* — Banner & Witcoff, Ltd.

(57) ABSTRACT

This invention relates to monospecific and multispecific antibodies that may be utilized for the diagnosis and treatment of various diseases. In addition, these antibodies may be modified by protease cleavage. Protease control or regulation may be provided by a protease site located in, for example, a linker. These protease-regulated antibodies may also be utilized for the diagnosis and treatment of various diseases.

38 Claims, 18 Drawing Sheets

(56) References Cited

OTHER PUBLICATIONS

Tamura et al., "Structural Correlates of an Anticarcinoma Antibody: Identification of Specificity-Determining Residues (SDRs) and Development of a Minimally Immunogenic Antibody Variant by Retention of SDRs Only," J. Immunol. 164, 1432-41, 2000.

Wüest et al., "TNF-Selectokine: a novel prodrug generated for tumor targeting and site-specific activation of tumor necrosis factor," Oncogene 21, 4257-65, 2002.

* cited by examiner

MONOSPECIFIC AND MULTISPECIFIC ANTIBODIES AND METHOD OF USE

This application is a national phase application of PCT/EP2008/006750, which was filed on Aug. 16, 2008 and published in English on Feb. 19, 2009. PCT/EP2008/006750 claims the benefit of U.S. Provisional Application Ser. No. 60/955,912, filed Aug. 15, 2007, and U.S. Provisional Application Ser. No. 60/955,913, filed Aug. 15, 2007, the contents of which are incorporated herein by reference in their entireties.

This application incorporates by reference the contents of a 277 kb text file created on Feb. 2, 2010 and named "WO2009021754_sequencelisting.txt," which is the sequence listing for this application.

FIELD OF THE INVENTION

This invention relates to monospecific and multispecific antibodies that may be utilized for the diagnosis and treatment of various diseases. In addition, these antibodies may be modified by protease cleavage. Protease control or regulation may be provided by a protease site located in, for example, a linker. These protease-regulated antibodies may also be utilized for the diagnosis and treatment of various diseases.

BACKGROUND OF THE INVENTION

An antibody may be directed against one or more different antigens or one or more different epitopes on the same antigen. For example, a bispecific antibody is directed against two different antigens or two different epitopes on the same antigen. As bispecific antibodies can simultaneously bind to two distinct targets, these antibodies have great potential for antibody-based diagnosis and for the treatment of various diseases and disorders such as cancer, infectious diseases, autoimmune diseases, and blood diseases. For example, bispecific antibodies can selectively stimulate and expand T lymphocytes (Wong, et al., J. Immunol. 139:1369-1374, 1987; Wong, et al., Clin. Immunol. Immunopathol. 58:236-250, 1991), direct immune cells or toxic agents to kill tumor cells (Lum, et al., Exp. Hematol. 34:1-6, 2006; Wolf, et al., Drug Discov. Today 10:1237-1244, 2005; Cao, et al., Adv. Drug Deliv. Rev. 55:171-197, 2003; Talac, et al., J. Biol. Regul. Homeost. Agents 14:175-181, 2000), and simultaneously block two receptors (Lu, et al., J. Biol. Chem. 279:2856-2565, 2004). In addition, a bispecific antibody may be used as a substitute for Factor VIII to enhance enzymatic reaction (US Patent Application No. 2007/0041978) or to direct stem cells to the site of injury in patients with myocardial infarction (Lum, et al., Blood Cells Mol. Dis. 32:82-87, 2004).

Bispecific antibodies targeting tumor-associated antigens and toxic agents may be used in cancer therapy. For example, using this technology, one arm of the bispecific antibody may be directed to a tumor-associated antigen such as Her2, EGF receptor, CD20, CD22, CD30, CD33, CD52, and CA-125, and the other arm of the bispecific antibody may target a toxin, drug, or cytokine. That is, bispecific antibodies may selectively direct toxic agents to tumor cells enhancing the efficacy of therapeutic antibodies and decreasing systemic toxicity. Examples of toxin/drug include calicheamicin, doxorubicin, epirubicin, methotrexate, ricin A, saporin, gelonin, and vinca alkaloids, and cytokine examples include tumor necrosis factor alpha (TNF-alpha) and IL-2.

Specific cleavage by proteases of defined sites in biologically important effector proteins is a well known method for the natural control of cellular and extracellular physiological processes. Examples include protease activation and inhibition of the coagulation cascade (Butenas, et al., Biochemistry 67:3-12, 2002; Esmon, Chest, 124:26S-32S, 2003), protease activation of protease-activatable receptors (Coughlin, Arterioscler. Thromb. Vasc. Biol. 18:514-518, 1998), protease release of membrane associated cytokines (Amour, et al., FEBS Lett. 435:39-44, 1998), protease processing of prohormones in secretory vesicles (Moore, et al., Arch. Physiol. Biochem. 110:16-25, 2002), and protease processing of proproteins during secretion (Scamuffa, et al., FASEB J. 20:1954-1963, 2006). Proteases are often expressed or located in a tissue-specific or tumor-specific manner and examples include the membrane serine protease corin in heart tissue (Yan, et al., Proc. Natl. Acad. Sci. USA 97:8525-8529, 2000), the kallikrein serine protease prostate-specific antigen (PSA) in prostate tissue, prostate cancer, and seminal fluid (Veveris-Lowe, et al., Semin. Thromb. Hemost. 33:87-99, 2007), the membrane serine protease hepsin in liver tissue and tumors (Xuan, et al., Cancer Res. 66:3611-3619, 2006), coagulation protease factor X expressed in the liver and secreted into blood (Miao, et al., J. Biol. Chem. 267:7395-7401, 1992), and digestive proteases expressed in the pancreas and released to the duodenum (Belorgey, et al., Biochem. J. 313:555-560, 1996). Specific cleavage of amino acid sequences by human proteases include thrombin (Chang, Eur. J. Biochem. 151:217-224, 1985), factor Xa (Nagai, et al., Methods Enzymol. 153:461-481, 1987), furin (Brennan, et al., FEBS Lett. 347:80-84, 1994), subtilisin-like prohormone convertases (Lipkind, et al., J. Biol. Chem. 270:13277-13284, 1995), and the matrix metalloproteinases (Minod, et al., J. Biol. Chem. 281:38302-38313, 2006). Genes encoding specific proteases may be up-regulated in tumor tissue and Table 2 indicates proteases that are associated with cancer tissue.

Protease cleavage is widely used in in vitro studies to specifically remove protein or peptide tags from recombinant proteins or to process hybrid recombinant proteins. For example, human rhinovirus 3C protease, thrombin, or factor Xa have been used to remove glutathione S-transferase (GST) tags (Dian, et al., Life Sciences News—Amersham Biosciences 10:1-5, 2002) and factor Xa has been use to process hybrid proteins (Nagai, et al., 1987). Proteases are often targets for drugs as a means to regulate biological processes; and examples include factor Xa (Phillips, et al., J. Med. Chem. 41:3557-3562, 1998), thrombin (Riester, et al., Proc. Natl. Acad. Sci. USA 102:8597-8602, 2005), urokinase (Killeen, et al., Br. J. Cancer 96:262-268, 2007), and factor VIIa (Kohrt, et al., Bioorg. Med. Chem. Lett. 15:4752-4756, 2005). Finally, proteins developed as biological drugs may be modified to prevent cleavage by proteases and to improve their stability in vitro or in vivo (Light, et al., Eur. J. Biochem. 262:522-533, 1999; Saenko, et al., Haemophilia 12:42-51, 2006).

Specific protease cleavage sites have been incorporated into linkers that link a toxin molecule to a targeting antibody in order to allow protease specific release of the toxin by intracellular proteases (Trail, et al., Cancer Immunol. Immunother. 52:328-337, 2003). Furthermore, targeting antibodies have been created in many formats. For example, bispecific antibodies have been developed to allow binding to two different antigens or two different epitopes of an antigen by a single antibody molecule (Segal, et al., Curr. Opin. Immunol. 11:558-562, 1999; Tomlinson, et al., Methods Enzymol. 326:461-479, 2000; Wu, et al., Nat Biotechnol. 25:1290-

1297, 2007). Other bispecific molecules have been generated with the ability to block two receptors (Lu, et al., J. Biol. Chem. 279:2856-2865, 2004) and to recruit immune cells to attack cancer cells and tumor tissue (Loffler, et al., Leukemia 17:900-909, 2003; Lum, et al., Exp. Hematol. 34:1-6, 2006).

The present invention relates to a novel antibody format, for example, monospecific and multispecific antibodies. The antibodies of the present invention may be constructed by tandem linking of two different heavy chain (H) variable region domains ($V_H$) and two different light chain (L) variable region domains ($V_L$). The heavy chain and light chain may form a Fab-like or IgG-like molecule through the disulfide bond between constant (C) regions. Multispecific antibodies may be generated by linking more than two antibody variable domains.

The antibodies of the present invention may be modified by protease cleavage. These protease-regulated antibodies may be, for example, monospecific antibodies, bispecific antibodies, or antibodies with sequential binding-activity upon protease digestion in either, for example, Fab-like or IgG-like format. Protease control or regulation may be provided by a protease site located in, for example, a linker. These protease-regulated antibodies may be utilized for the diagnosis and treatment of various diseases, and provide an additional level of control for biological drugs for therapeutic or diagnostic applications.

DESCRIPTION OF THE INVENTION

Figure 1:
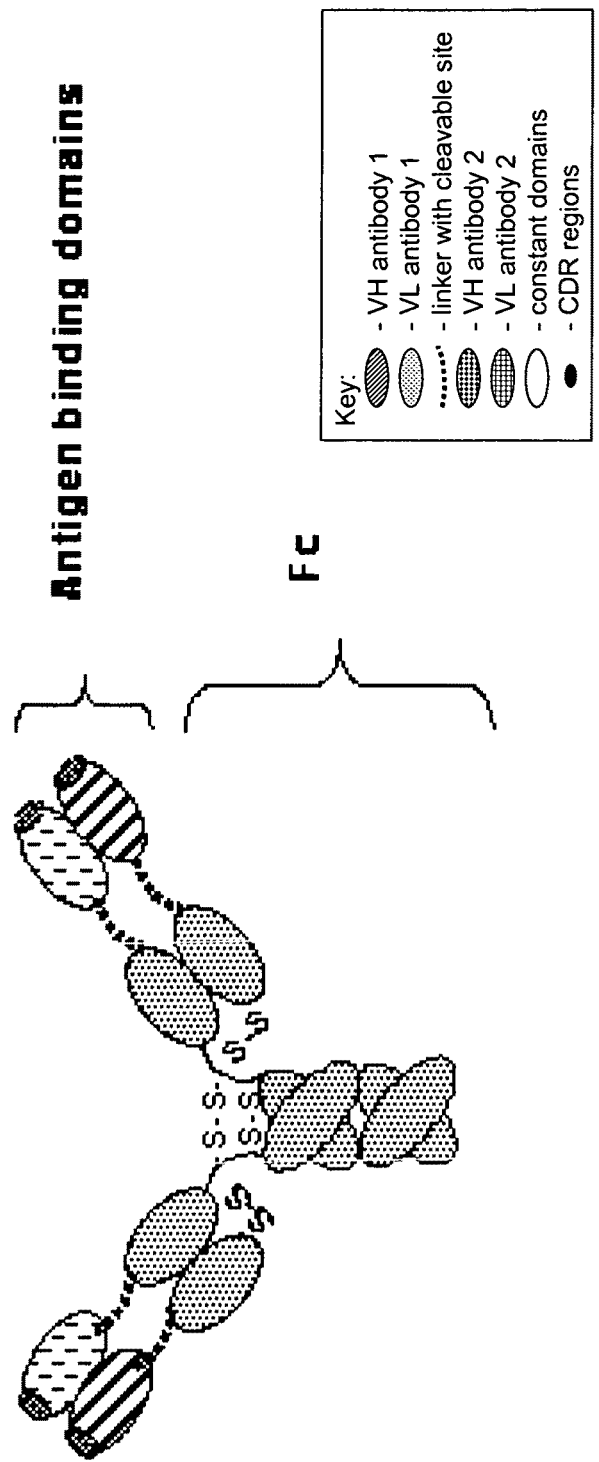
FIG. 1. Schematic drawing of a monospecific protease-regulated antibody with a linker which contains a protease site between variable domain and Fc domain ("Type 1").

It is to be understood that this invention is not limited to the particular methodology, protocols, cell lines, animal species or genera, constructs, and reagents described and as such may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural reference unless the context clearly dictates otherwise. Thus, for example, reference to "an antibody" is a reference to one or more antibodies and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are hereby incorporated herein by reference for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

For convenience, the meaning of certain terms and phrases employed in the specification, examples, and appended claims are provided below.

"Antibody" as used herein includes intact immunoglobulin molecules (e.g., IgG1, IgG2a, IgG2b, IgG3, IgM, IgD, IgE, IgA), as well as fragments thereof, such as Fab, F(ab')$_2$, scFv, Fv, and diabody which are capable of specific binding to an epitope of a protein. The term antibody also extends to other protein scaffolds that are able to orient antibody complementarity-determining region (CDR) inserts into the same active binding conformation as that found in natural antibodies such that the binding to the target antigen observed with these chimeric proteins is maintained relative to the binding activity of the natural antibody from which the CDRs were derived.

"Antibody fragments" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; monospecific antibodies; bispecific antibodies; and multispecific antibodies formed from antibody fragments.

The term "autoimmune diseases" includes, but is not limited to, multiple sclerosis, rheumatoid arthritis, lupus, type I diabetes mellitus, Crohn's disease, autoimmune hemolytic anemia, autoimmune hepatitis, glomerulonephritis, inflammatory bowel disease, myocarditis, psoriasis, thyroiditis, ulcerative colitis, and Graves' disease.

The terms "biological sample" or "patient sample" as used herein, refers to a sample obtained from an organism or from components (e.g., cells) of an organism. The sample may be of any biological tissue or fluid. The sample may be a "clinical sample" which is a sample derived from a patient. Such samples include, but are not limited to, sputum, blood, serum, plasma, blood cells (e.g., white cells), tissue samples, biopsy samples, urine, peritoneal fluid, and pleural fluid, saliva, semen, breast exudate, cerebrospinal fluid, tears, mucous, lymph, cytosols, ascites, amniotic fluid, bladder washes, and bronchioalveolar lavages or cells therefrom, among other body fluid samples. The patient samples may be fresh or frozen, and may be treated with heparin, citrate, or EDTA. Biological samples may also include sections of tissues such as frozen sections taken for histological purposes.

The term "cancer" includes, but is not limited to, solid tumors, such as cancers of the breast, respiratory tract, brain, reproductive organs, digestive tract, urinary tract, eye, liver, skin, head and neck, thyroid, parathyroid, and their distant metastases. The term also includes lymphomas, sarcomas, and leukemias.

The term "conjugate" refers to an antibody chemically linked to a chemical moiety, such as a therapeutic or cytotoxic agent.

The term "infectious diseases" includes, but is not limited to, HTV/AIDS, lower respiratory infections, diarrheal diseases, tuberculosis, malaria, measles, pertussis, tetanus, meningitis, syphilis, hepatitis B and tropical diseases.

The term "linker" refers to a peptide (or polypeptide) comprising two or more amino acid residues joined by peptide bonds and used to link one or more antibody domains. The linker may contain one or more protease cleavage sites.

The term "protease" refers to any enzyme, including the endopeptidases and exopeptidases, which catalyze the hydrolytic breakdown of proteins into peptides or amino acids.

The present invention is directed to the design and production of monospecific, bispecific antibodies, and multispecific antibodies. For example, the bispecific antibodies and multispecific antibodies may comprise tandem linked $V_H a$-$V_H b$-$V_H c$ ... $C_H$ in one polypeptide and $V_L a$-$V_L b$-$V_L c$ ... $C_L$ in another polypeptide. Alternately, the $V_H$ and $V_L$ domains may be exchanged from one polypeptide to another to create polypeptides such as $V_H a$-$V_L b$-$V_H c$ ... $C_H$ and $V_L a$-$V_H b$-$V_L c$ ... $C_L$. The two polypeptides may form □immers in the Fab format or the half IgG-like format, or two of each polypeptide may form a four polypeptide-containing homodimer of the IgG-like format. These bispecific or multispecific antibodies or antibody fragments thereof may simultaneously bind different antigens or different epitopes of the same antigen.

As an example, a recombinant IgG-like bispecific antibody may be constructed by the tandem linking of two different $V_H$ domains of a heavy chain and two different $V_L$ domains of a light chain. The construct is exemplified as follows:

heavy chain=$NH_2$-$V_H 1$-$V_H 2$-$C_H 1$-$C_H 2$-$C_H 3$-COOH
light chain=$NH_2$-$V_L 1$-$V_L 2$-$C_L$.

Another bispecific antibody may comprise the following:
heavy chain=$NH_2$-$V_L 1$-$V_H 2$-$C_H 1$-$C_H 2$-$C_H 3$-COOH
light chain=$NH_2$-$V_H 1$-$V_L 2$-$C_L$-COOH.

The present invention also relates to protease-regulated antibodies. Protease-regulated antibodies may be, for example, monospecific antibodies, bispecific antibodies, multispecific antibodies, or antibodies with sequential binding-activity upon protease digestion in either, for example, Fab-like or IgG-like format. Protease control or regulation may be provided by a selective protease site located in, for example, a linker. These protease-regulated antibodies may be utilized for the diagnosis and treatment of various diseases including but not limited to cancer, infectious disease, and autoimmune diseases, and provide an additional level of control for biological drugs for therapeutic or diagnostic applications.

Protease-regulated antibodies may comprise a heavy chain (H) variable domain ($V_H$)-linker-heavy chain constant domain (CH) in one polypeptide and a light chain (L) variable domain ($V_L$)-linker-light chain constant domain (CL) in another polypeptide. Bispecific protease-regulated antibodies may comprise, for example, $V_{H1}$-linker-$V_{H2}$-CH in one polypeptide and $V_{L1}$-linker-$V_{L2}$-CL in another polypeptide, both regulated by proteolytic cleavage of the linker. Alternately, the $V_H$ and $V_L$ domains in the bispecific protease-regulated antibodies may be exchanged from one polypeptide to another polypeptide to create polypeptides such as, for example, $V_{H1}$-linker-$V_{L2}$-CH and $V_{L1}$-linker-$V_{H2}$-CL. The two polypeptides may form □immers, for example, in a Fab-like format, a half-IgG-like format, or an IgG-like format (e.g., two of each polypeptide forming a four polypeptide-containing homodimer). The bispecific and sequential protease-regulated antibodies or antibody fragments may (1) simultaneously bind two different antigens or different epitopes of the same antigen, (2) sequentially bind two different antigens or different epitopes on the same antigen in a manner that may be dependent on the length, adjacent sequence, and design of the linker, or (3) a monospecific protease-activated binder which is in latent or prodrug form prior to protease digestion and which is switched on by protease cleavage. Libraries of bispecific protease-regulated antibodies in the Fab-like format can be readily created, expressed in bacteria, and screened for specific functionalities, including susceptibility of the linker to cleavage by a specific protease and optimization of this cleavage step.

Several types of protease-regulated antibodies are described herein whereby antibody formats are designed with selectivity due to specific protease-dependent binding or protease-specific functionality. In particular, these protease-regulated antibodies may be described by deletions and/or additions of antibody framework, location of the linker, and its properties including length and solvent accessibility. Furthermore, the linker may contain a cleavage site specific for a protease found in a target cell or tissue. One example of a protease-regulated antibody may contain a protease site in a linker located between the variable domain and the constant region domain and this antibody may bind only one antigen as illustrated in FIG. 1 ("Type 1").

Figure 2:
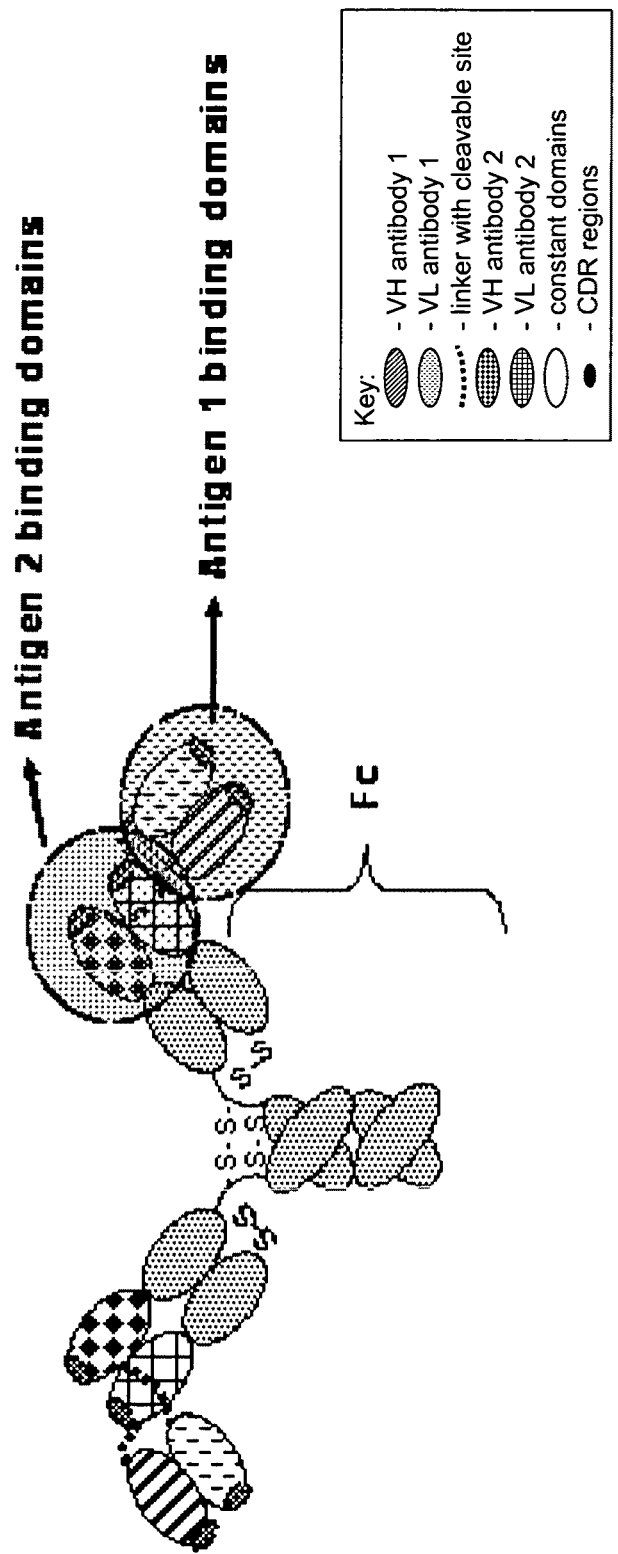
FIG. 2. Schematic drawing of a bispecific protease-regulated antibody with a linker which contains a protease cleavage sequence that allows removal of one antigen-binding site ("Type 2").
Figure 3:
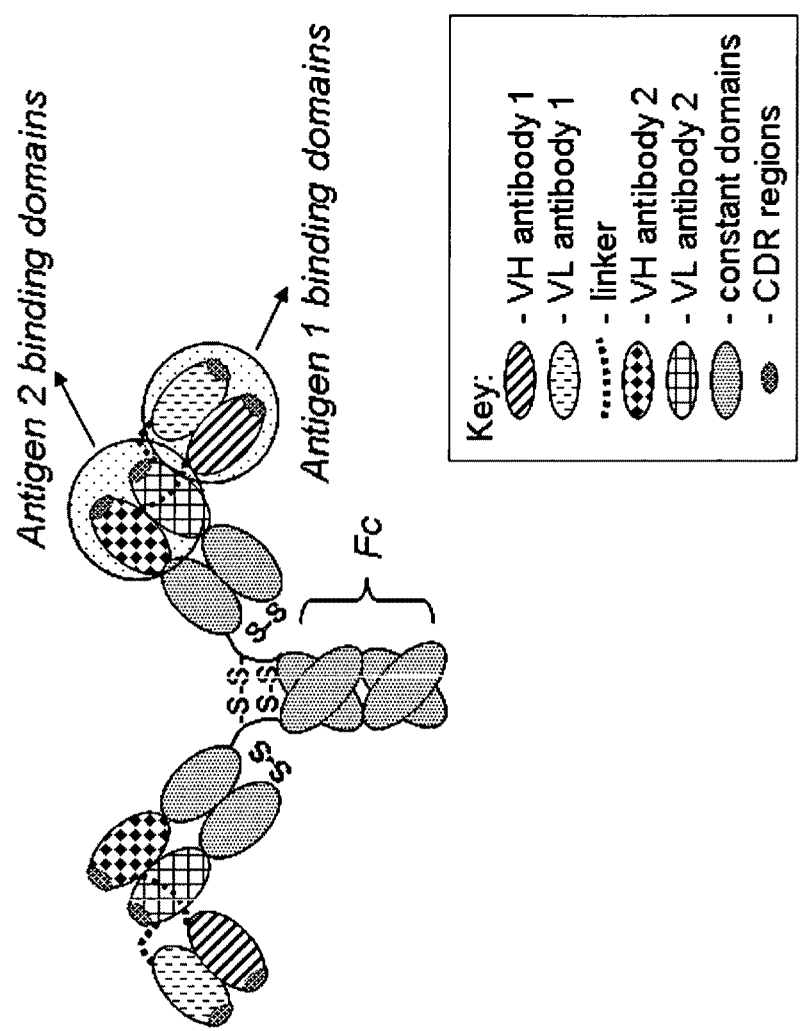
FIG. 3. Schematic drawing of another bispecific protease-regulated antibody with a linker which contains a protease cleavage sequence that allows removal of one antigen-binding site ("Type 2").

Another example of a protease-regulated antibody may simultaneously bind two different antigens or two different epitopes as shown in FIGS. 2 and 3 ("Type 2") in the absence of a protease. The first $V_H/V_L$ domains of this antibody bind to an antigen without blocking the second $V_H/V_L$ domains from binding to a second antigen. This antibody can bind to antigens without steric blocking of the CDR regions of the second variable domains. The simultaneous binding of this protease-regulated antibody to both antigens is prevented by proteolytic cleavage. That is, when the linker is cleaved by a protease, the antibody can only bind to the second antigen or separately bind two antigens. Simultaneous antigen binding is important for antibody function, for example, in cross-linking receptors, which may be prevented by proteolytic cleavage. Thus, an additional degree of specificity is added by including a protease site in the linker.

Figure 4:
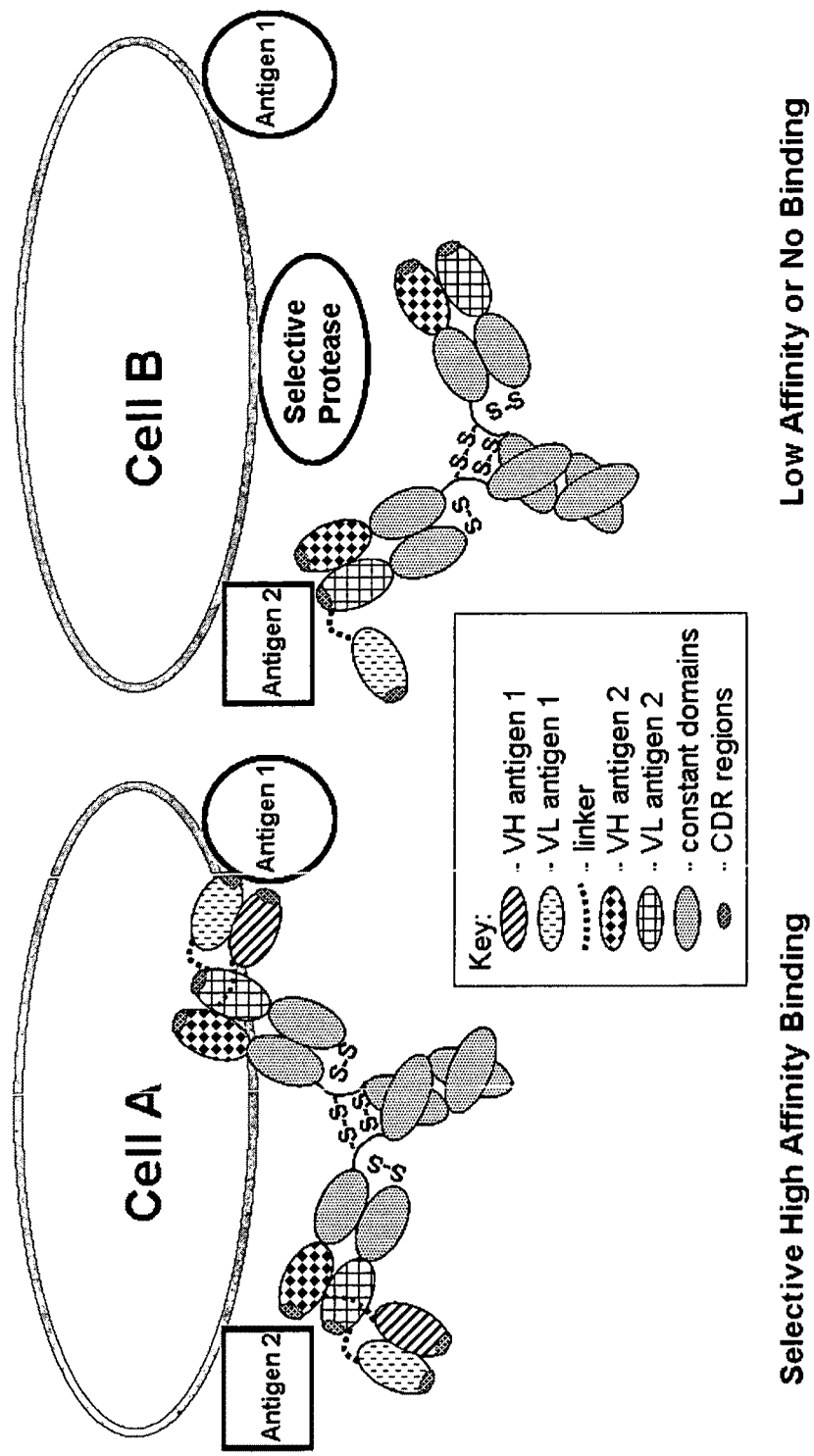
FIG. 4. Schematic drawing of the application of a bispecific protease-regulated antibody that simultaneously binds two different antigens.

This bispecific protease-regulated antibody is more selective than a monospecific antibody because this antibody will specifically target cells or tissues expressing both antigens. The additional degree of specificity is provided by the specific protease site in the linker. In FIG. 4, Cell A and Cell B express both Antigen 1 and Antigen 2, however only Cell B expresses the selective protease. The bispecific protease-regulated antibody with the uncleavable linker (i.e., this linker does not contain the protease cleavage site) will bind to Cell A with greater avidity because the bispecific antibody is able to bind to both antigens. In contrast, the bispecific protease-regulated antibody will bind to Cell B with lower avidity because the Antigen 1 binding domain is removed by proteolytic cleavage of the linker by the selective protease expressed by Cell B (alternately, the selective protease may be expressed by adjacent cells localized in the same tissue as Cell B).

Figure 5:
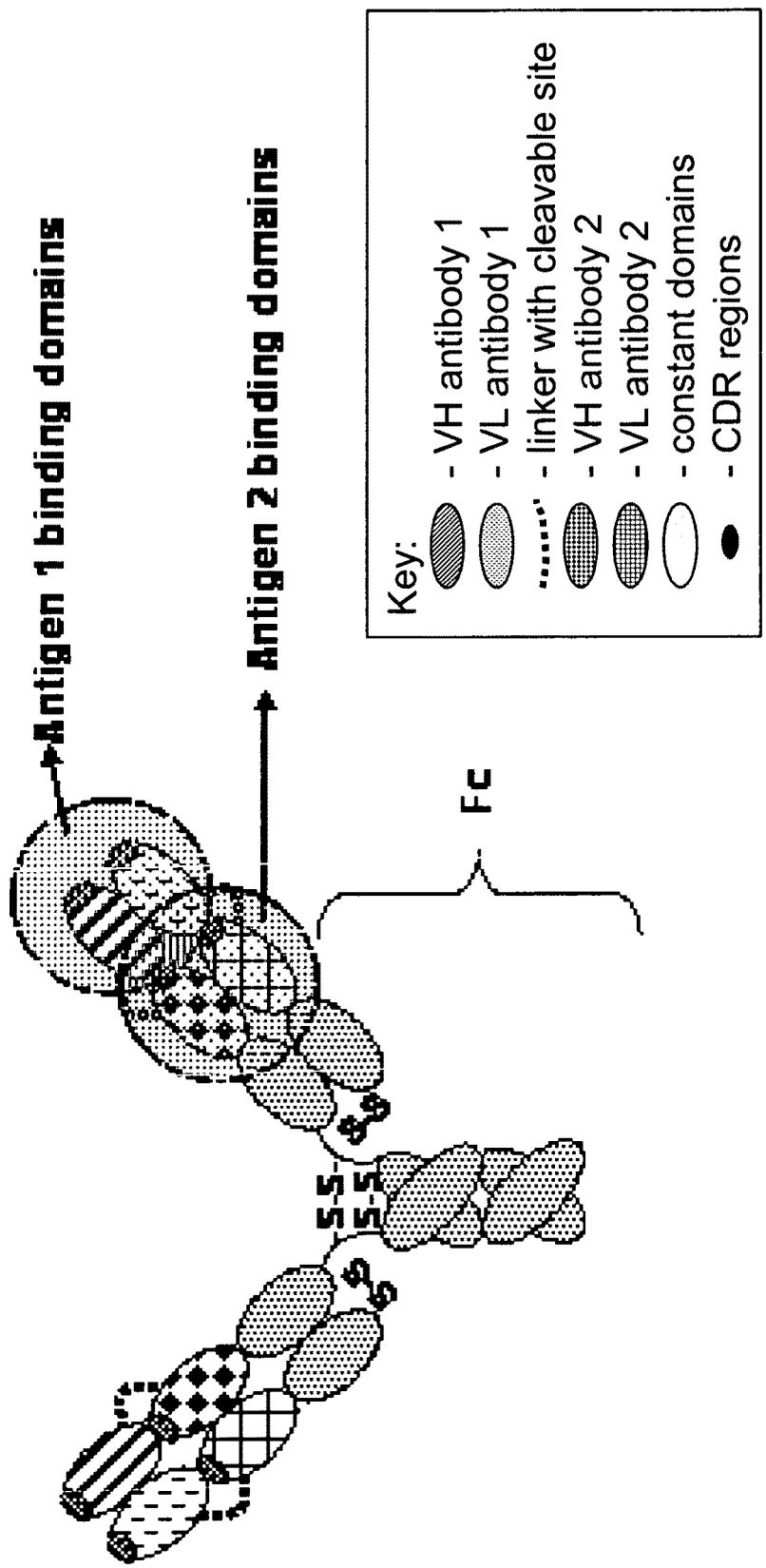
FIG. 5. Schematic drawing of a protease-regulated antibody that cannot bind to two different antigens simultaneously ("Type 3").

In contrast, FIG. 5 illustrates a protease-regulated antibody that may sequentially bind to each antigen in a protease-dependent manner. That is, prior to protease cleavage of the linker, the protease-regulated antibody binds to a first antigen and following protease cleavage, the antibody binds to a second antigen ("Type 3"). The $V_H/V_L$ domains of the N-terminal antibody bind to an antigen, but block the CDR regions of the downstream $V_H/V_L$ domains from binding to a second antigen. Protease cleavage of the linker allows removal of the N-terminal antibody, and removing the N-terminal antibody domains then permits binding to a second antigen. This allows for greater cell and/or tissue selectivity by requiring sequential binding.

Figure 6:
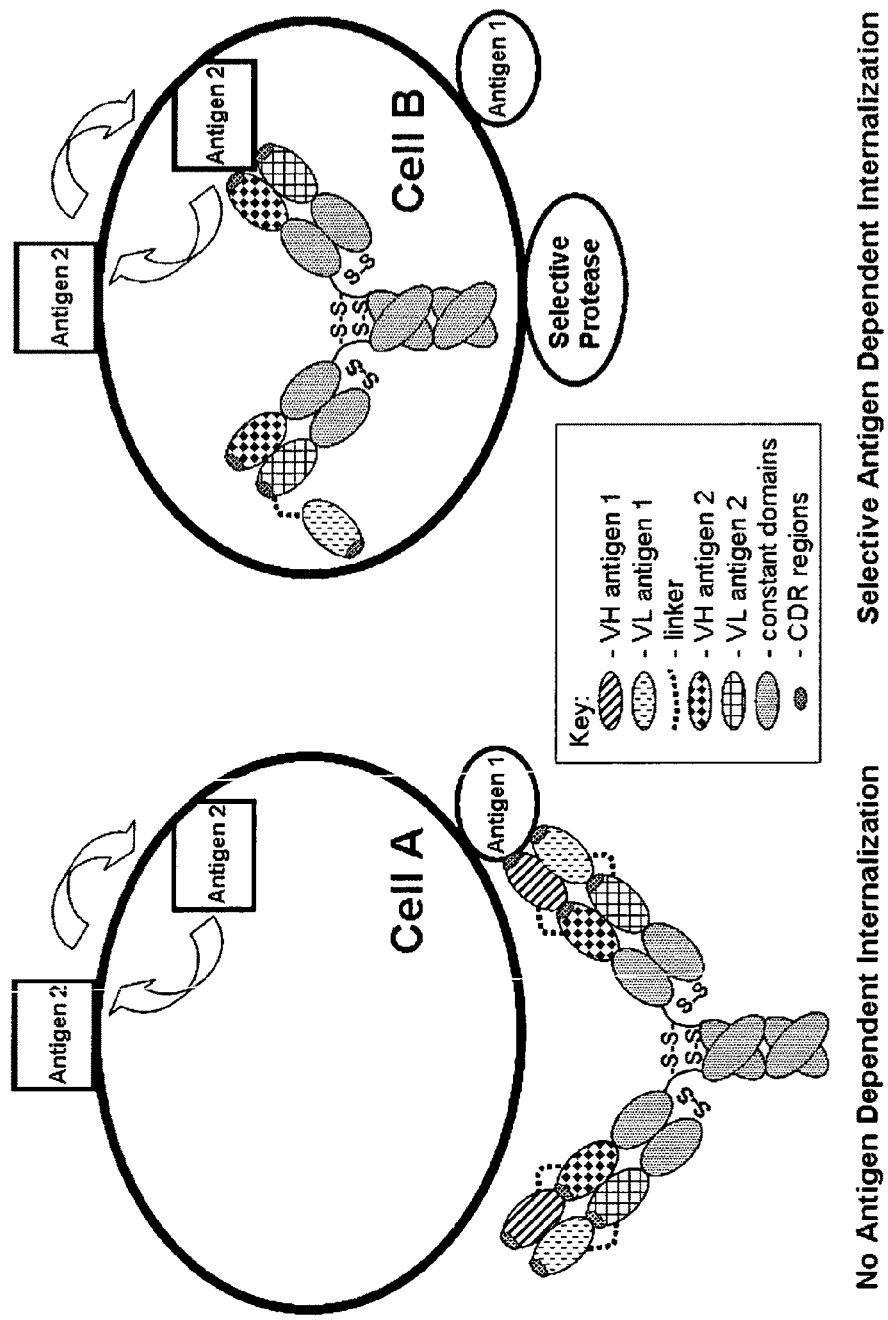
FIG. 6. Schematic drawing of the application of a protease-regulated antibody that cannot bind to two different antigens simultaneously.

In FIG. 6, Cell A and Cell B express both Antigen 1 and Antigen 2, but only Cell B expresses the selective protease. In addition, Antigen 2 is a cell surface receptor that internalizes into the cell and allows internalization of antibodies that bind to it. The protease-regulated antibody will bind to Antigen 1 expressed by Cell A and Cell B. However, only Cell B expresses the selective protease (or possibly cells adjacent to Cell B in the same tissue). The protease-regulated antibody will be activated by proteolytic cleavage and internalized via Antigen 2 expressed on Cell B. Thus, this protease-regulated antibody will be specifically internalized by cells expressing Antigen 1, Antigen 2, and the selective protease.

Figure 7:
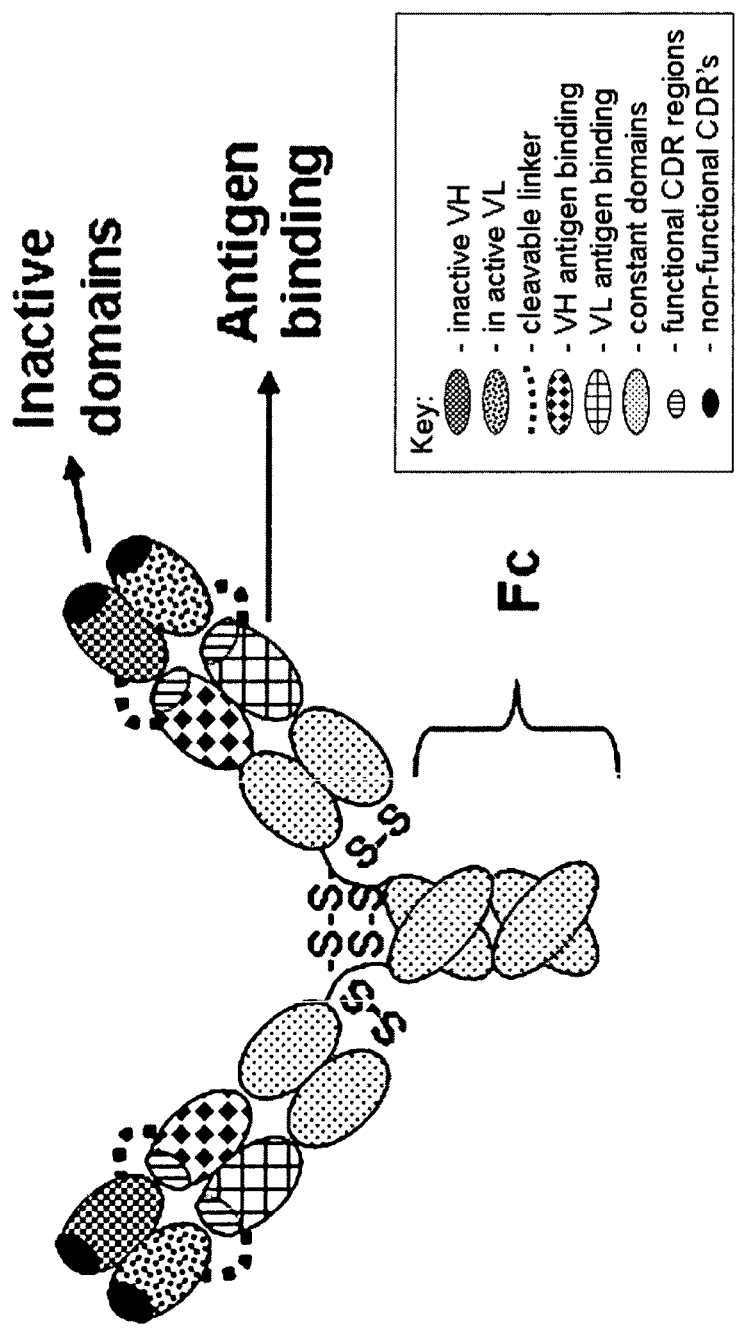
FIG. 7. Schematic drawing of a monospecific protease-regulated antibody 'prodrug' that can only bind antigen following protease activation to remove inactive blocking antibody domains ("Type 4").

In an additional example, a protease-regulated antibody may not bind to an antigen before protease digestion, but may bind to antigen following protease digestion ("Type 4"). An example of this antibody is illustrated in FIG. 7. This monospecific protease-regulated antibody also contains a protease cleavage linker that allows removal of the N-terminal non-functional antibody which then leads to binding to an antigen by the functional antibody domains that are thus exposed. Type 4 protease-regulated antibodies may be created by three approaches. In the first approach the protease cleavable linker sequence is modified so that it prevents the N-terminal $V_H$ and $V_L$ domains of a Type III antibody ($V_H1$ and $V_L1$) from binding to the first antigen. Examples of these linkers are shown in the sequences in Table 8. In the second approach, the linkers utilized in Type III antibodies shown in Tables 6 and 7 are now combined with heterodimeric N-terminal $V_H$ and $V_L$ domains that have been mutated to destroy their antigen binding function. Examples of this approach are shown in the sequences in Table 9 in which the CDR3 of $V_H1$ and CDR3 of $V_L1$ are replaced by a poly-alanine sequence of a similar length as the respective CDR. In the third approach, the linkers utilized in Type III antibodies shown in Tables 6 and 7 are combined with homodimeric N-terminal domains derived from the constant regions of antibodies. For example, the complete $V_H1$ and $V_L1$ domains of a Type III antibody are both replaced by the same constant domain that is capable of heterodimerization, for example, the CH3 domain of IgG or the CH4 domain of IgE.

These protease-regulated antibodies may be modified by protease cleavage of the linker as described below. For example, the protease-regulated antibody illustrated in FIG. 1 (Type 1) contains a protease site in the linker between the antigen binding domains and the Fc domain. This antibody will specifically target cells or tissues that present the antigen. When the linker is cleaved by the protease, the resultant protease-regulated antibody releases the functional Fc portion. In tissues where the protease is present, this antibody will release the Fc portion which is essential to antigen crosslinking, and induce an immune response such as antibody-dependent cellular cytotoxicity (ADCC) and complement-dependent cytotoxicity (CDC). To illustrate, hepsin, a serine protease, is expressed in both tumor tissue and normal liver tissue. In a cancer patient treated with a protease-regulated antibody against hepsin, the antibody would attack the tumor cells via the Fc portion-induced ADCC and CDC. However, in the liver, the protease-regulated antibody would initially bind to hepsin, but the Fc portion would be cleaved by a liver-specific protease prior to initiation of ADCC or CDC preventing liver toxicity.

The peptide (or polypeptide) linker of the protease-regulated antibody may comprise two or more amino acid residues and may contain one or more protease cleavage sites. The linkers may alter antibody conformation, stability, and antigen-binding activities. The length of linkers may range, for example, from 0 to about 100 amino acid residues. The following are examples of linkers:

```
Linker 1:
SDDDDK                           (SEQ ID NO: 1)

Linker 2:
GGGGSDDDDK                       (SEQ ID NO: 2)

Linker 3:
GGGGSDDDDKGGGGS                  (SEQ ID NO: 3)

Linker 4:
GGGGSGGGGSGGGGS                  (SEQ ID NO: 4)

Linker 5:
IHPVLSGLSRIVNGEDAVPG             (SEQ ID NO: 5)

Linker 6:
VAAPFDDDDKIVGGYICEEN             (SEQ ID NO: 6)

Linker 7:
ELLESYIDGRIVEGSDAEIG             (SEQ ID NO: 7)

Linker 8:
STQSFNDFTRVVGGEDAKPG             (SEQ ID NO: 8)

Linker 9:
PERGDNNLTRIVGGQECKDG             (SEQ ID NO: 9)

Linker 10:
EDQEDQVDPRLIDGKMTRRG             (SEQ ID NO: 10)

Linker 11:
KRNASKPQGRIVGGKVCPKG             (SEQ ID NO: 11)

Linker 12:
SVCTTKTSTRIVGGTNSSWG             (SEQ ID NO: 12)

Linker 13:
SRIVG                            (SEQ ID NO: 13)

Linker 14:
GSLVSGSCSQIINGEDCSPH             (SEQ ID NO: 14)

Linker 15:
SRIIN                            (SEQ ID NO: 15)

Linker 16:
NKLVH                            (SEQ ID NO: 16)

Linker 17:
DKIID                            (SEQ ID NO: 17)

Linker 18:
FNVLG                            (SEQ ID NO: 18)

Linker 19:
TRAIG                            (SEQ ID NO: 19)

Linker 20:
TRLDP                            (SEQ ID NO: 20)

Linker 21:
TRIIK                            (SEQ ID NO: 21)

Linker 22:
SGSNQ                            (SEQ ID NO: 22)

Linker 23:
SKVLN                            (SEQ ID NO: 23)

Linker 24:
NKIIG                            (SEQ ID NO: 24)

Linker 25:
DKLLE                            (SEQ ID NO: 25)
```

Table 1 illustrates the excision site of several proteases.

TABLE 1

| Excision site ↓ | Cleavage Enzyme/Self-Cleavage |
|---|---|
| Asp-Asp-Asp-Asp-Lys↓ (DDDDK) (SEQ ID NO: 26) | Enterokinase |
| Ile-Glu/Asp-Gly-Arg↓ (IE/DGR) (SEQ ID NO: 27) | Factor Xa protease |
| Leu-Val-Pro-Arg↓Gly-Ser (LVPR \| GS) (SEQ ID NO: 28) | Thrombin |
| Glu-Asn-Leu-Tyr-Phe-Gln↓Gly (ENLYFQ \| G) (SEQ ID NO: 29) | TEV protease |
| Leu-Glu-Val-Leu-Phe-Gln↓Gly-Pro (LEVLFQ \| GP) (SEQ ID NO: 30) | Human rhinovirus 3C protease |
| Ser-Ser-Val-Phe-Ala-Gln↓Ser-Ile-Pro (SSVFAQ \| SIP) (SEQ ID NO: 31) | PCSK9 (NARC-1) |
| Lys-Gln-Leu-Arg↓Val-Val-Asn-Gly (KQLR \| VVNG) (SEQ ID NO: 32) | Hepsin |

TABLE 1-continued

| Excision site ↓ | Cleavage Enzyme/ Self-Cleavage |
|---|---|
| Specific intein-encoded sequences | Intein 1 & intein 2 |
| Signal sequences | Signal peptidases |

The cleavage sites of additional proteases that may be incorporated in a linker are described in Table 2.

TABLE 2

| TUMOR ASSOCIATED PROTEASES (Extracellular Or Intracellular) |
|---|
| ADAM metallopeptidase domain 9 (meltrin gamma) |
| ADAM metallopeptidase domain 10 |
| ADAM metallopeptidase domain 17 (TNFalpha, converting enzyme) |
| ADAM metallopeptidase domain 28 |
| ADAM-like, decysin 1 |
| ADAM metallopeptidase, thrombospondin type 1 motif 1 |
| ADAM metallopeptidase, thrombospondin type 1 motif 5, aggrecanase-2 |
| ADAMTS-like 3 |
| ADAMTS-like 4 |
| Beta-site APP-cleaving enzyme 1 |
| Bleomycin hydrolase |
| Bone morphogenetic protein 1 |
| Complement component 1, r subcomponent |
| Complement component 1, s subcomponent |
| Calpain 2, (m/II) large subunit |
| Caspase 1, apoptosis-related cysteine peptidase (IL-1β convertase) |
| Caspase 2, apoptosis-related cysteine peptidase |
| Caspase 3, apoptosis-related cysteine peptidase |
| Caspase 4, apoptosis-related cysteine peptidase |
| Caspase 6, apoptosis-related cysteine peptidase |
| Caspase 7, apoptosis-related cysteine peptidase |
| Caspase 9, apoptosis-related cysteine peptidase |
| Complement factor D (adipsin) |
| CASP8 and FADD-like apoptosis regulator |
| Cathepsin B |
| Cathepsin F |
| Cathepsin H |
| Cathepsin K |
| Cathepsin L |
| Cathepsin L2 |
| Cathepsin O |
| Cathepsin S |
| Cylindromatosis (turban tumor syndrome) |
| Extra spindle pole bodies homolog 1 (S. Cerevisiae) |
| Granzyme A (granzyme 1, CTL-associated serine esterase 3) |
| Histocompatibility (minor) 13 |
| Hepsin (transmembrane protease, serine 1) |
| HtrA serine peptidase 1 |
| Kallikrein-related peptidase 11 |
| Legumain |
| Lon peptidase 1, mitochondrial |
| Mucosa associated lymphoid tissue lymphoma translocation gene 1 |
| Membrane-bound transcription factor peptidase, site 1 |
| Matrix metallopeptidase 1 (interstitial collagenase) |
| Matrix metallopeptidase 12 (macrophage elastase) |
| Matrix metallopeptidase 14 (membrane-inserted) |
| Matrix metallopeptidase 9 (gelatinase B, 92 kDa type IV collagenase) |
| N-acetylated alpha-linked acidic dipeptidase-like 1 |
| Napsin A aspartic peptidase |
| Pregnancy-associated plasma protein A, pappalysin 1 |
| Proprotein convertase subtilisin/kexin type 5 |
| Plasminogen activator, tissue |
| Plasminogen activator, urokinase |
| Peptidase (mitochondrial processing) beta |
| Protease, serine, 3 (mesotrypsin) |
| Protease, serine, 8 (prostasin) |
| Proteasome (prosome, macropain) subunit, alpha type, 1 |
| Proteasome (prosome, macropain) subunit, alpha type, 6 |
| Proteasome (prosome, macropain) subunit, beta type, 4 |
| Proteasome (prosome, macropain) subunit, beta type, 9 |
| Proteasome (prosome, macropain) subunit, beta type, 10 |
| SUMO1/sentrin specific peptidase 1 |

TABLE 2-continued

| TUMOR ASSOCIATED PROTEASES (Extracellular Or Intracellular) |
|---|
| Suppression of tumorigenicity 14 (colon carcinoma) |
| Tubulointerstitial nephritis antigen |
| Torsin family 1, member A (torsin A) |
| Tripeptidyl peptidase I |
| Tripeptidyl peptidase II |
| Tryptase alpha/beta 1 |
| Tryptase alpha/beta 1 |
| Ubiquitin specific peptidase 4 (proto-oncogene) |
| Ubiquitin specific peptidase 10 |
| Ubiquitin specific peptidase 11 |
| Ubiquitin specific peptidase 14 (tRNA-guanine transglycosylase) |
| Ubiquitin specific peptidase 15 |
| Ubiquitin specific peptidase 16 |
| Ubiquitin specific peptidase 18 |
| Ubiquitin specific peptidase 25 |
| YME1-like 1 (S. cerevisiae) |
| Zinc metallopeptidase (STE24 homolog, yeast) |

The protease-regulated antibodies of the present invention may bind one or more antigens. These antigens may be selected from the group consisting of cytokines, cell surface receptors, enzymes, and receptors. These antigens include, but are not limited to, CD3, CD4, CD8, CD20, CD25, CD28, CD33, CD52, IL-2, IL-7, IL-8, TNF-alpha, TGF-beta INF-beta, INF-gamma, GMCSF, GCSF, VEGF, C5, EpCAM, EGF receptor, CD2 receptor, IL 2 receptor, IgE receptor, intergrin, and MHC class II.

The antibodies of the present invention may be utilized for the diagnosis and therapy of various diseases. For example, antibodies directed against human immunological cells and tumor-associated antigen may be used for cancer therapy. These antibodies may also be directed against tumor-associated antigen and toxic agents or enzymes for use as a cancer therapeutic. The antibodies of the present invention may also be utilized for the treatment of hemophilia and thrombosis as well as stem cell transplantation. These antibodies may be used for the selective stimulation and expansion of lymphocyte subset. In addition, these antibodies may used for the detection of disease-related antigens.

For cancer immunotherapy, bispecific antibodies may be used to recruit the immune system to attach tumor cells. Targets on immunological cells include, but are not limited to, CD3, CD8, and Fc receptor. Tumor-associated antigens include, but are not limited to, Her2, EGF receptor, CD20, CA-125, and carcinoembryonic antigen (CEA). For example, a bispecific antibody against CD8 and Her2 can direct CD8-expressing cytotoxic lymphocytes to attack Her2 expressing breast cancer cells.

The antibodies or antibody fragments of the invention, or compositions including the antibodies or fragments, can include a cytoxic agent that is conjugated to the antibody or fragment. In one aspect, the cytotoxic agent is monomethylauristatin-E (MMAE), however, other cytoxic agents are also provided, which can include, for example, functional analogs of MMAE (e.g. monomethylauristatin-F), and other cytotoxic agents, e.g., aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-I 1), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FUdR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribomiclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin, or combinations thereof. Any of the cytoxic agents can also include functional analogs thereof.

Antibody Technology

A number of technologies are available to produce antibodies. For example, phage-antibody technology may be used to generate antibodies (Knappik, et al., J. Mol. Biol. 296:57-86, 2000). Another approach for obtaining antibodies is to screen a DNA library from B cells as described by Dower, et al., (WO 91/17271) and McCafferty, et al., (WO 92/01047). In these methods, libraries of phage are produced in which members display different antibodies on their outer surfaces. Antibodies are usually displayed as Fv or Fab fragments. Phage displaying antibodies are selected by affinity enrichment for binding to a selected protein. Antibodies may also be produced using trioma methodology (Oestberg, et al., Hybridoma 2:361-367, 1983; U.S. Pat. No. 4,634,664; U.S. Pat. No. 4,634,666).

Antibodies may also be purified from any cell that expresses the antibodies, including host cells that have been transfected with antibody-encoding expression constructs. The host cells may be cultured under conditions whereby the antibodies are expressed. Purified antibody may be separated from other cellular components that may associate with the antibody in the cell, such as certain proteins, carbohydrates, or lipids using methods well known in the art. Such methods include, but are not limited to, size exclusion chromatography, ammonium sulfate fractionation, ion exchange chromatography, affinity chromatography, and preparative gel electrophoresis. Purity of the preparations may be assessed by any means known in the art, such as SDS-polyacrylamide gel electrophoresis. A preparation of purified antibodies may contain more than one type of antibody.

Alternatively, antibodies may be produced using chemical methods to synthesize its amino acid sequence, such as by direct peptide synthesis using solid-phase techniques (see, e.g., Merrifield, J. Am. Chem. Soc. 85:2149-2154, 1963; Roberge, et al., Science 269:202-204, 1995). Protein synthesis may be performed using manual techniques or by automation. Automated synthesis may be achieved, for example, using Applied Biosystems 431A Peptide Synthesizer (Perkin Elmer). Optionally, fragments of antibodies may be separately synthesized and combined using chemical methods to produce a full-length molecule.

The antibodies of the present invention may be generated from parental antibodies. Parent antibodies may be selected from various antibodies capable of binding specific targets and well known in the art, such as, but not limited to, but are not limited to anti-TNF antibody, anti-IL-12 antibody; anti-IL-18 antibody, anti-O5, anti-CD147, anti-gp120, anti-CD11a, anti-CD18, anti-VEGF, anti-CD40L, anti-ICAM-1, anti-CD2, anti-EGFR, anti-TGF-beta 2, anti-E-selectin, anti-Her2/neu, anti-CD14, anti-ICAM-3, anti-CD80, anti-CD4, anti-CD3, anti-CD23, anti-beta2-integrin, anti-CD52, anti-CD22, anti-CD20, anti-CD25, anti-CD33, anti-HLA, anti-IL-1alpha, anti-IL-1, anti-IL-1 receptor, anti-IL-2 receptor, anti-IL-4, anti-IL4 receptor, anti-IL5, anti-IL-5 receptor, anti-IL-6, anti-IL-8, anti-IL-9, anti-IL-13, anti-IL-13 receptor, anti-IL-17, and anti-IL-23. Parent antibodies may also be selected from various therapeutic antibodies including, but are not limited to, rituximab, trastuzumab, pertuzumab, cetuximab, alemtuzumab, muromonab, ibritumomab, gemtuzumab ozogamicin, alefacept, abciximab, basiliximab, palivizumab, infliximab, adalimumab, etanercept, natalizumab, bevacizumab, omalizumab, efalizumab, clenoliximab, labetuzumab, epratuzumab, and visilizumab.

The newly synthesized molecules may be substantially purified by preparative high performance liquid chromatography (see, e.g., Creighton, *Proteins: Structures and Molecular Principles*, WH Freeman and Co., New York, N.Y., 1983). The composition of a synthetic polypeptide may be confirmed by amino acid analysis or sequencing (e.g., using Edman degradation).

The present invention also relates to bispecific or bifunctional antibodies that have one binding site that specifically binds to a first antigen and a second binding site that specifically binds to a second antigen. This results in multifunctional valency, that is, an ability to bind at least two different epitopes simultaneously.

Polynucleotides Encoding Antibodies

The present invention also relates to polynucleotides encoding antibodies. These polynucleotides may be used, for example, to produce quantities of the antibodies for therapeutic or diagnostic use.

Polynucleotides of the present invention may also be isolated from host cells, free of other cellular components such as membrane components, proteins, and lipids. Polynucleotides may be isolated using standard nucleic acid purification techniques, or synthesized using an amplification technique such as the polymerase chain reaction (PCR), or by using an automatic synthesizer. Methods for isolating polynucleotides are routine and are known in the art. Any such technique for obtaining a polynucleotide may be used to obtain isolated polynucleotides encoding antibodies of the invention. For example, restriction enzymes and probes may be used to isolate polynucleotides which encode antibodies.

Antibody-encoding cDNA molecules may be made with standard molecular biology techniques, using mRNA as a template. Thereafter, cDNA molecules may be replicated using molecular biology techniques known in the art and disclosed in manuals such as Sambrook, et al., (*Molecular Cloning: A Laboratory Manual*, (Second Edition, Cold Spring Harbor Laboratory Press; Cold Spring Harbor, N.Y.; 1989) Vol. 1-3). An amplification technique, such as PCR, may be used to obtain additional copies of the polynucleotides. Alternatively, synthetic chemistry techniques may be used to synthesize polynucleotides encoding antibodies of the invention.

To express a polynucleotide encoding an antibody, the polynucleotide may be inserted into an expression vector that contains the necessary elements for the transcription and translation of the inserted coding sequence. Methods that are well known to those skilled in the art may be used to construct expression vectors containing sequences encoding antibodies and appropriate transcriptional and translational control elements. These methods include in vitro recombinant DNA techniques, synthetic techniques, and in vivo genetic recombination. Such techniques are described, for example, in Sambrook, et al. (1989) and in Ausubel, et al., (*Current Protocols in Molecular Biology*, John Wiley & Sons, New York, N.Y., 1995).

A variety of expression vector/host systems may be utilized to contain and express sequences encoding antibodies. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV); or bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements may vary in strength and specificity. Depending on the vector system and host utilized, any number of suitable transcription and translation elements, including constitutive and inducible promoters, may be used. For example, when cloning in bacterial systems, inducible promoters can be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses may be used. If it is necessary to generate a cell line that contains multiple copies of a nucleotide sequence encoding an antibody, vectors based on SV40 or EBV may be used with an appropriate selectable marker.

General texts describing additional molecular biological techniques useful herein, including the preparation of antibodies include Berger and Kimmel (*Guide to Molecular Cloning Techniques, Methods in Enzymology*, Vol. 152, Academic Press, Inc.); Sambrook, et al., (*Molecular Cloning: A Laboratory Manual*, (Second Edition, Cold Spring Harbor Laboratory Press; Cold Spring Harbor, N.Y.; 1989) Vol. 1-3); *Current Protocols in Molecular Biology*, (F. M. Ausabel et al. [Eds.], Current Protocols, a joint venture between Green Publishing Associates, Inc. and John Wiley & Sons, Inc. (supplemented through 2000)); Harlow et al., (*Monoclonal Antibodies: A Laboratory Manual*, Cold Spring Harbor Laboratory Press (1988), Paul [Ed.]); *Fundamental Immunology*, (Lippincott Williams & Wilkins (1998)); and Harlow, et al., (*Using Antibodies: A Laboratory Manual*, Cold Spring Harbor Laboratory Press (1998)).

Assays

The affinity ($K_d$) of antibody binding to an antigen may be assayed using any method known in the art including, for example, immunoassays such as enzyme-linked immununospecific assay (ELISA), Bimolecular Interaction Analysis (BIA) (see, e.g., Sjolander and Urbaniczky; Anal. Chem. 63:2338-2345, 1991; Szabo, et al., Curr. Opin. Struct. Biol. 5:699-705, 1995), and fluorescence-activated cell sorting (FACS) for quantification of antibody binding to cells that express an antigen. BIA is a technology for analyzing biospecific interactions in real time, without labeling any of the interactants (e.g., BIAcore™). Changes in the optical phenomenon surface plasmon resonance (SPR) may be used as an indication of real-time reactions between biological molecules.

The present invention also relates to the use of quantitative immunoassays to measure levels of proteins in patient samples. Many formats may be adapted for use with the methods of the present invention. For example, the detection and quantitation of a protein in patient samples may be performed, by enzyme-linked immunosorbent assays, radioimmunoassays, dual antibody sandwich assays, agglutination assays, fluorescent immunoassays, immunoelectron and scanning microscopy, among other assays commonly known in the art. The quantitation of a protein in such assays may be adapted by conventional methods known in the art. Serial changes in circulating a protein levels may be detected and quantified by a sandwich assay in which the capture antibody has been immobilized using conventional techniques on the surface of the support.

Suitable supports include, for example, synthetic polymer supports, such as polypropylene, polystyrene, substituted polystyrene, polyacrylamides (such as polyamides and polyvinylchloride), glass beads, agarose, and nitrocellulose.

The antibodies useful to identify proteins may be labeled in any conventional manner. An example of a label is horseradish peroxidase, and an example of a method of labeling antibodies is by using biotin-strepavidin complexes.

As appropriate, antibodies used in the immunoassays of this invention that are used as tracers may be labeled in any manner, directly or indirectly, that results in a signal that is visible or can be rendered visible. Detectable marker substances include radionuclides, such as $^3H$, $^{125}I$, and $^{131}I$; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatases, glucose oxidase, glucose-6-phosphate dehydrogenase, acetylcholinesterase, alpha beta-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatases and paranitrophenyl phosphate (pNPP).

Another detection and quantitation systems according to this invention produce luminescent signals, bioluminescent (BL) or chemiluminescent (CL). In chemiluminescent (CL) or bioluminescent (BL) assays, the intensity or the total light emission is measured and related to the concentration of the unknown analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, *Vargulla* and *Renilla*. Luminol can be used optionally with an enhancer molecule such as 4-iodophenol or 4-hydroxy-cinnamic acid. Typically, a CL signal is generated by treatment with an oxidant under basic conditions.

Additional luminescent detection systems are those wherein the signal (detectable marker) is produced by an enzymatic reaction upon a substrate. CL and BL detection schemes have been developed for assaying alkaline phosphatases (AP), glucose oxidase, glucose 6-phosphate dehydrogenase, horseradish peroxidase (HRP), and xanthine-oxidase labels, among others. AP and HRP are two enzyme labels which can be quantitated by a range of CL and BL reactions. For example, AP can be used with a substrate, such as an adamantyl 1,2-dioxetane aryl phosphate substrate (e.g. AMPPD or CSPD; Kricka, L. J., "Chemiluminescence and Bioluminescence, Analysis by," *Molecular Biology and Biotechnology: A Comprehensive Desk Reference* (ed. R. A. Meyers) (VCH Publishers; N.Y., N.Y.; 1995)); for example, a disodium salt of 4-methoxy-4-(3-phosphatephenyl)spiro [1,2-dioxetane-3,2'-adamantane], with or without an enhancer molecule such as 1-(trioctylphosphonium methyl)-4-(tributylphosphonium methyl)benzene diochloride. HRP is may be used with substrates, such as, 2',3',6'-trifluorophenyl-methoxy-10-methylacridan-9-carboxylate.

CL and BL reactions may be adapted for analysis not only of enzymes, but also of other substrates, cofactors, inhibitors, metal ions, and the like. For example, luminol, firefly luciferase, and marine bacterial luciferase reactions are indicator reactions for the production or consumption of peroxide, ATP, and NADPH, respectively. They may be coupled to other reactions involving oxidases, kinases, and dehydrogenases, and may be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between an antibody and a marker or the use of a signal amplification system.

Examples of binding pairs that may be used to link antibodies to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B 12/intrinsic factor; cortisone, cortisol/cortisol binding protein; and ligands for specific receptor protein/membrane associated specific receptor proteins.

Various means for linking labels directly or indirectly to antibodies are known in the art. For example, labels may be bound either covalently or non-covalently. Exemplary antibody conjugation methods are described in Avarmeas, et al., Scan. J. Immunol. 8(Suppl. 7): 7, 1978); Bayer, et al., Meth. Enzymol. 62:308, 1979; Chandler, et al., J. Immunol. Meth. 53:187, 1982; Ekeke and Abuknesha, J. Steroid Biochem. 11:1579, 1979; Engvall and Perlmann, J. Immunol. 109:129, 1972; Geoghegan, et al., Immunol. Comm. 7:1, 1978; and Wilson and Nakane, *Immunofluorescence and Related Techniques*, Elsevier/North Holland Biomedical Press; Amsterdam (1978).

Depending upon the nature of the label, various techniques may be employed for detecting and quantitating the label. For fluorescers, a large number of fluorometers are available. For chemiluminescers, luminometers or films are available. With enzymes, a fluorescent, chemiluminescent, or colored product may be determined or measured fluorometrically, luminometrically, spectrophotometrically, or visually.

Various types of chemiluminescent compounds having an acridinium, benzacridinium, or acridan type of heterocyclic ring systems are other examples of labels. Examples of acridinium esters include those compounds having heterocyclic rings or ring systems that contain the heteroatom in a positive oxidation state including such ring systems as acridinium, benz[a]acridinium, benz[b]acridinium, benz[c] acridinium, a benzimidazole cation, quinolinium, isoquinolinium, quinolizinium, a cyclic substituted quinolinium, phenanthridinium, and quinoxalinium.

The tracer may be prepared by attaching to the selected antibody either directly or indirectly a reactive functional group present on the acridinium or benzacridinium ester, as is well known to those skilled in the art (see, e.g., Weeks, et al., Clin. Chem. 29(8):1474-1479, 1983). Examples of compounds are acridinium and benzacridinium esters with an aryl ring leaving group and the reactive functional group present in either the para or the meta position of the aryl ring. (see, e.g., U.S. Pat. No. 4,745,181 and WO 94/21823).

Methods of Use

As used herein, various terms are defined below.

The term "treatment" includes any process, action, application, therapy, or the like, wherein a subject (or patient), including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a disease, condition, and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The antibodies of the invention may be administered in combination with the following agents: cytotoxic agent, angiogenesis inhibitors, antirheumatic agent, muscle relaxant, narcotic, non-steroid anti-inflammatory drug, analgesic, anesthetic, sedative, local anesthetic, neuromuscular blocker, antimicrobial agent, immunoglobulins, antidepressant, asthma medication, cytokine, and cytokine antagonist.

For example, the antibodies of the invention may be administered in combination with various anti-cancer agents including, but not limited to, bleomycin, docetaxel, doxorubicin, edatrexate, erlotinib, etoposide, finasteride, flutamide, gemcitabine, genitinib, goserelin acetate, granisetron, imatinib, irinotecan, ondansetron, paclitaxel, pegaspargase, pilocarpine hydrochloride, porfimer sodium, interleukin-2, rituximab, topotecan, trastuzumab, triapine, vincristine, and vinorelbine tartrate, or therapeutic antibodies or fragments thereof, or anti-angiogenic agent, such as, for example, angiostatin, bevacizumab, sorafenib, baculostatin, canstatin, maspin, anti-VEGF antibodies or peptides, anti-placental growth factor antibodies or peptides, anti-Flk-1 antibodies, anti-Fit-1 antibodies or peptides, laminin peptides, fibronectin peptides, plasminogen activator inhibitors, tissue metalloproteinase inhibitors, interferons, interleukin 12, Gro-β, thrombospondin, 2-methoxyoestradiol, proliferin-related protein, carboxiamidotriazole, CM1O1, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline.

The phrase "therapeutically effective" means the amount of each agent administered that will achieve the goal of improvement in a disease, condition, and/or disorder severity, while avoiding or minimizing adverse side effects associated with the given therapeutic treatment.

The term "pharmaceutically acceptable" means that the subject item is appropriate for use in a pharmaceutical product.

The antibodies of this invention are expected to be valuable as therapeutic agents. Accordingly, an embodiment of this invention includes a method of treating the various conditions in a patient (including mammals) which comprises administering to said patient a composition containing an amount of an antibody of the invention that is effective in treating the target condition.

The antibodies of the present invention may be used in the treatment or prevention of various diseases including, but not limited to, cancer, infectious disease, and autoimmune diseases.

The antibodies of the present invention or compositions including the antibodies may include a cytotoxic agent (e.g., monomethylauristatin-E) that is conjugated to the antibody.

Antibodies of the present invention may be administered alone or in combination with one or more additional therapeutic agents. Combination therapy includes administration of a single pharmaceutical dosage formulation which contains an antibody of the present invention and one or more additional therapeutic agents, as well as administration of the antibody of the present invention and each additional therapeutic agents in its own separate pharmaceutical dosage formulation. For example, an antibody of the present invention and a therapeutic agent may be administered to the patient together in a single oral dosage composition or each agent may be administered in separate oral dosage formulations.

Where separate dosage formulations are used, the antibody of the present invention and one or more additional therapeutic agents may be administered at essentially the same time (e.g., concurrently) or at separately staggered times (e.g., sequentially).

To assess the ability of a particular antibody to be therapeutically useful to treat cancer, as an example, the antibody may be tested in vivo in a mouse xenograft tumor model. An example of a therapeutic model is detailed in Example 8.

Pharmaceutical Compositions

The antibodies described herein may be provided in a pharmaceutical composition comprising a pharmaceutically acceptable carrier. The pharmaceutically acceptable carrier may be non-pyrogenic. The compositions may be administered alone or in combination with at least one other agent, such as stabilizing compound, which may be administered in any sterile, biocompatible pharmaceutical carrier including, but not limited to, saline, buffered saline, dextrose, and water. A variety of aqueous carriers may be employed including, but not limited to saline, glycine, or the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, and the like. The concentration of the antibody of the invention in such pharmaceutical formulation may vary widely, and may be selected primarily based on fluid volumes, viscosities, etc., according to the particular mode of administration selected. If desired, more than one type of antibody may be included in a pharmaceutical composition.

The compositions may be administered to a patient alone, or in combination with other agents, drugs or hormones. In addition to the active ingredients, these pharmaceutical compositions may contain suitable pharmaceutically acceptable carriers comprising excipients and auxiliaries that facilitate processing of the active compounds into preparations which may be used pharmaceutically. Pharmaceutical compositions of the invention may be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., $20^{th}$ edition, 2000).

Diagnostic Methods

The present invention also provides diagnostic methods with which a particular antigen may be detected in a patient sample or biological sample. Such diagnostic methods may be used, for example, to diagnose disorders in which a particular antigen is elevated or reduced. Such disorders include, but are not limited to, cancer, infectious disease, and autoimmune diseases. As an example, when used for diagnosis, detection of an amount of the antibody-antigen complex in a sample from a patient which is greater than an amount of the complex in a normal sample identifies the patient as likely to have the disorder The patient sample may be contacted with an antibody of the invention, and the patient sample may then be assayed for the presence of an antibody-antigen complex. As described above, the antibody may comprise a detectable label, such as a fluorescent, radioisotopic, chemiluminescent, or enzymatic label, such as horseradish peroxidase, alkaline phosphatase, or luciferase.

Optionally, the antibody may be bound to a solid support, which may accommodate automation of the assay. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art may be used to attach the antibody to the solid support, including use of covalent and non-covalent linkages, passive absorption, or pairs of binding moieties attached to the antibody and the solid support. Binding of antigen and the antibody may be accomplished in any vessel suitable for containing the reactants. Examples of such vessels include microtiter plates, test tubes, and microcentrifuge tubes.

Determination of a Therapeutically Effective Dose

The determination of a therapeutically effective dose is well within the capability of those skilled in the art. A therapeutically effective dose refers to the amount of an antibody that may be used to effectively treat a disease (e.g., cancer) compared with the efficacy that is evident in the absence of the therapeutically effective dose.

The therapeutically effective dose may be estimated initially in animal models (e.g., rats, mice, rabbits, dogs, or pigs). The animal model may also be used to determine the appropriate concentration range and route of administration. Such information may then be used to determine useful doses and routes for administration in humans.

Therapeutic efficacy and toxicity (e.g., $ED_{50}$—the dose therapeutically effective in 50% of the population and $LD_{50}$—the dose lethal to 50% of the population) of an antibody may be determined by standard pharmaceutical procedures in cell cultures or experimental animals. The dose ratio of toxic to therapeutic effects is the therapeutic index, and it may be expressed as the ratio, $LD_{50}/ED_{50}$. The data obtained from animal studies may used in formulating a range of dosage for human use. The dosage contained in such compositions may be within a range of circulating concentrations that include the $ED_{50}$ with little or no toxicity. The dosage varies within this range depending upon the dosage form employed, sensitivity of the patient, and the route of administration.

The exact dosage may be determined by the practitioner, in light of factors related to the patient who requires treatment. Dosage and administration may be adjusted to provide sufficient levels of the antibody or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Effective in vivo dosages of an antibody are in the range of about 5 µg to about 500 µg/kg of patient body weight.

The mode of administration of antibody-containing pharmaceutical compositions of the present invention may be any suitable route which delivers the antibody to the host. As an example, pharmaceutical compositions of the invention may be useful for parenteral administration (e.g., subcutaneous, intramuscular, intravenous, or intranasal administration).

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLES

In order that this invention may be better understood, the following examples are set forth. These examples are for the purpose of illustration only, and are not to be construed as limiting the scope of the invention in any manner. All publications mentioned herein are incorporated by reference in their entirety.

Example 1

Construction, Expression, and Purification of Fab-Like Antibody

Figure 8:
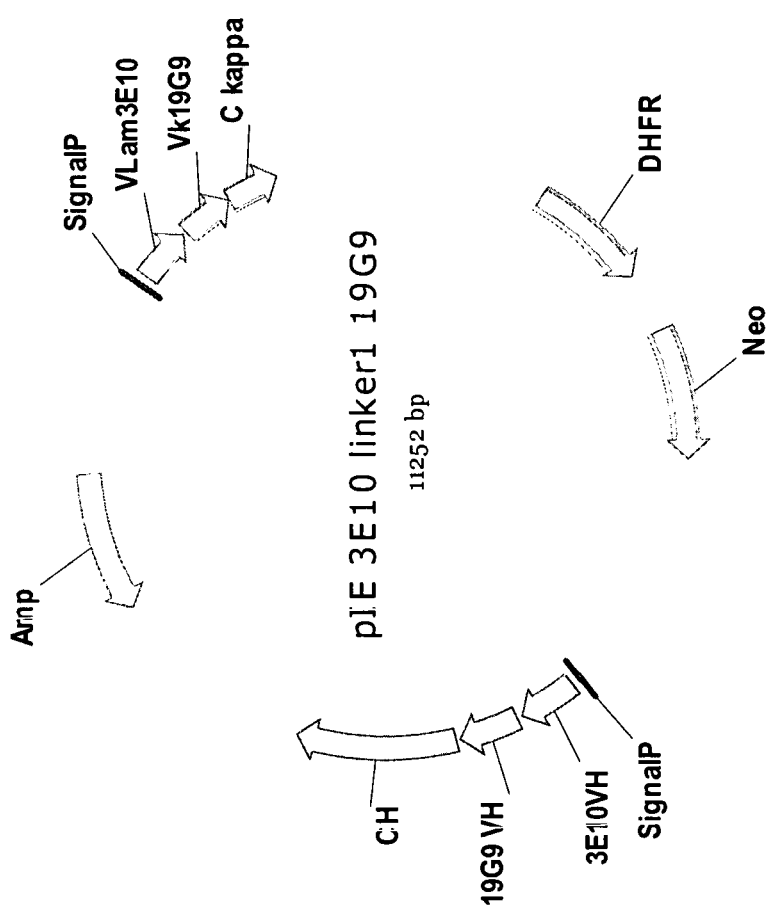
FIG. 8. Map of an expression vector for an IgG-like bispecific antibody. SignalP: signal peptide; VLam3E10: variable region of 3E10 lambda chain; Vk19G9: variable region of 19G9 kappa chain; C kappa: constant region of kappa chain; DHFR: dihydrofolate reductase; $V_H$: variable region of heavy chain; Neo: neomycin resistant gene; 3E10VH: variable region of 3E10 heavy chain; 19G9VH: variable region of 19G9 heavy chain; CH: constant region of heavy chain; Amp: ampicillin resistant gene.
Figure 9:
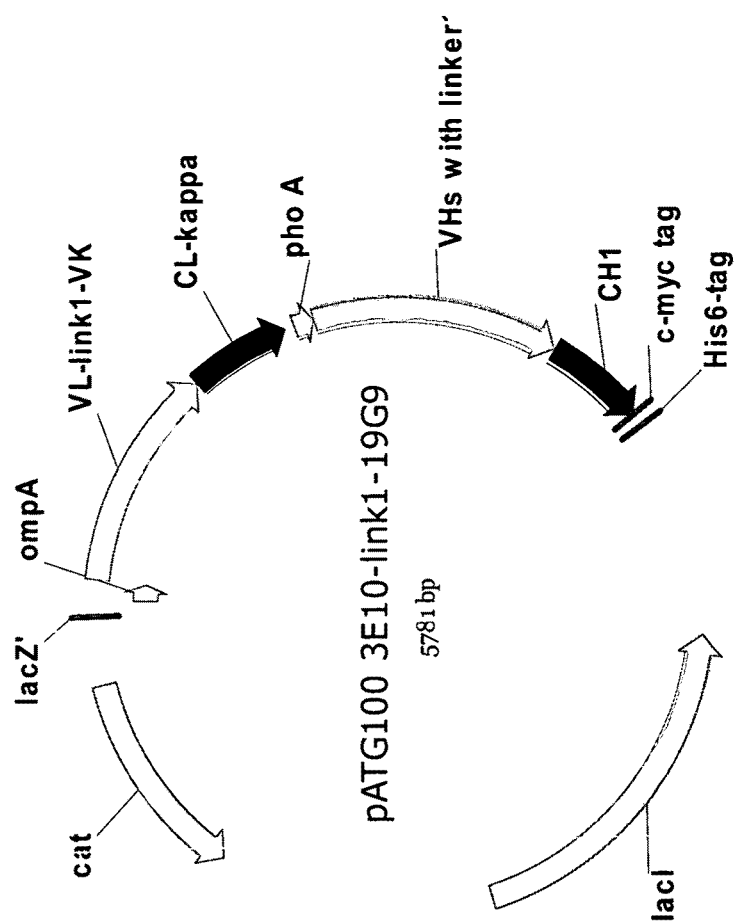
FIG. 9. Map of expression vector of Fab-like bispecific antibody. LacZ, lac Z promoter; ompA and pho A, signal peptide; VL-link1-VK, variable region of light chain of bispecific antibody against tissue factor and RG1; CL-kappa, constant region of kappa chain; VHs with linker, variable region of heavy chain of bispecific antibody against tissue factor and RG1; CH1, the first constant region of IgG heavy chain; cat, chloramphenicol resistant gene.

Antibodies 3E10 and 19G9 recognize tissue factor (TF) and tumor-associated antigen RG1, respectively. These two antibodies were used to construct protease-regulated antibodies containing the protease site DDDDK (SEQ ID NO: 26) linker located between the antigen binding domains and constant region domain. Specifically, these antibodies contained $V_L$-DDDDK-CL on the light chain and $V_H$-DDDDK-CH1-Myc-His6 on the heavy chain, where the linker is cleavable by enterokinase, and Myc and His6 are tags for detection and purification. The DNA sequences for the two antibodies were cloned into bacterial expression vectors using standard molecular biology technologies, and the constructs were confirmed by DNA sequencing. Examples of plasmid are shown in FIGS. 8 and 9. The plasmid containing either 3E10 or 19G9 was expressed and purified from bacterial strain TG1. Briefly, a single colony of bacteria strain TG1 containing the antibody expression plasmid was selected and grown overnight in 8 ml of 2× YT medium in the presence of 34 µg/ml chloramphenicol and 1% glucose. A volume of culture (7 ml) was transferred to 250 ml fresh 2× YT medium containing 34 µg/ml chloramphenicol and 0.1% glucose. After 3 hours of incubation, 0.5 mM IPTG was added to induce Fab expression. The culture was incubated overnight at 25° C. Following incubation, the culture was centrifuged to pellet the bacterial cells, and the pellet was resuspended in a Bug Buster® lysis buffer (Novagen, Madison, Wis.). After centrifugation, the bacterial lysis supernatant was filtered, and the Fab fragments were affinity-purified through a Ni-NTA column (Qiagen, Valencia, Calif.) according to the manufacturer's instruction.

Other examples of protease-regulated antibodies were also constructed using tandem linked variable regions from 3E10 and 1909. These antibodies contained, for example, $V_L$3E10-DDDDK-$V_L$19G9-CL on the light chain and $V_H$3E10-DDDDK-$V_H$19G9-CH1-Myc-His6 on the heavy chain, where the linker is cleavable by enterokinase, and Myc and His6 are tags for detection and purification. An antibody library was also constructed using the framework regions (FR), for example, FR4 of 3E10 and FR1 of 19G9 either intact or truncated. Several types of protease-regulated antibodies were screened from this library. The cloning, expression, and purification were performed as described above.

Example 2

Cloning and Expression of IgG-Like Antibodies

The expression vector pIE_SRgamma_fa contains cDNAs encoding the constant regions of human IgG1 (fa haplotype) and kappa chains, respectively. An overlap PCR was performed to link the variable regions of anti-TF antibody 3E10 and anti-RG1 antibody 19G9. The native signal peptide of 19G9 was used for secretion of the protease-regulated antibodies. Four examples of peptide linkers located between the variable regions of 3E10 and 19G9 are Linker 1: SDDDDK (SEQ ID NO: 2), Linker 2: GGGGSDDDDK (SEQ ID NO: 3), Linker 3: GGGGSDDDDKGGGGS (SEQ ID NO: 4), and Linker 4: GGGGSGGGGSGGGGS (SEQ ID NO: 5). The primers for amplification of the variable region of the light chain introduced Hind III and Bsiw I sites into the 5' and 3' ends of PCR fragment, respectively. The resulting PCR-amplified $V_L$ genes were cloned into the HindIII/Bsiw site of pIE_SRgamma1_fa to create pIE-3E10$V_L$-linker-19G9$V_L$. The same strategy was used to clone in frame $V_H$ fusions of 3E10 and 19G9 (including linkers 1-4) into pIE-3E10$V_L$-linker-19G9$V_L$. Briefly, the primer pairs of the variable regions of 3E10 and 19G9 contained NotI/ApaI sites. The PCR products were digested with NotI/ApaI and inserted upstream of the CH region of pIE-3E10$V_H$-linker-19G9$V_H$ ensuring that the $V_H$ regions were in frame with the CH region in the respective pIE derivatives. The final constructs were verified by DNA sequencing analysis.

Transfection and transient expression of the protease-regulated antibodies were conducted using mammalian cells. Approximately $4 \times 10^8$ CHO-S cells supplemented with CHO-SF medium were prepared for transfection. Transfection was carried out using Lipofectamine™ 2000 (Invitrogen, Carlsbad, Calif.) and 1 mg plasmid DNA following the manufacturer's instruction. The cells were grown for three days after transfection, and the culture media was harvested and filtered for antibody isolation and purification.

Examples of the protease-regulated antibodies are described in Tables 3-9

TABLE 3

PROTEASE-REGULATED ANTIBODIES (Type 1)

| Light chain | Heavy chain |
| --- | --- |

Fab-like protease-regulated antibodies against TF (3E10)

| | |
| --- | --- |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGAGGGGSDD DDKRTVAAPSVFIFPPSDEQLKSGTASVVC LLNNFYPREAKVQWKVDNALQSGNSQESVT EQDSKDSTYSLSSTLTLSKADYEKHKVYAC EVTHQGLSSPVTKSFNRGEC (SEQ ID NO: 33) | DLVESGGTLVQPGGSLRLSCAASGFSFTDAW MSWVRQAPGKELEWVSSISGSGGSTYYAGSV KGRFTISRDNSKNTLYLQMNSLRAEDTAVYY CARVLSLTDYYWYGMDVWGQGTLVTVSASDD DDKSSASTKGPSVFPLAPSSKSTSGGTAALG CLVKDYFPEPVTVSWNSGALTSGVHTFPAVL QSSGLYSLSSVVTVPSSSLGTQTYICNVNHK PSNTKVDKKVEPKCEF (SEQ ID NO: 34) |

Fab-like protease-regulated antibodies against RG1 (19G9)

| | |
| --- | --- |
| DIVLTQSPGTLSLSPGERATLSCRASQSVSS SYLAWYQQKPGQAPRLLIYGASSRATGIPDR FSGSGSGTDFTLTISRLEPEDFAVYYCQQYS SSLTFGGGTKVEIKDDDDKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC (SEQ ID NO: 35) | QLVQSGGGLVQPGGSLRLSCAGSGFTFSSYV MHWLRQAPGKGLEWVSVIGTGGVTHYADSVK GRFTISRDNAKNSLYLQMNSLRAEDTAVYYC ARWGYYGSGSYENDAFDIWGQGTMVTVDDDD KSSASTKGPSVFPLAPSSKSTSGGTAALGCL VKDYFPEPVTVSWNSGALTSGVHTFPAVLQS SGLYSLSSVVTVPSSSLGTQTYICNVNHKPS NTKVDKKVEPKCEF (SEQ ID NO: 36) |

IgG-like protease-regulated antibodies against TF (3E10)

| | |
| --- | --- |
| NFMLTQPHSVSASPGKTVTISCTRSSGSVAS YYVQWYQQRPGSSPTTVIYEDNHRPSGVPDR FSGSIDTSSNSASLTISGLKTEDEADYYCQS YDSNNLVVFGGGTKLTVLGQSDDDDKPKAAP SVTLFPPSSEELQANKATLVCLISDFYPGAV TVAWKADSSPVKAGVETTTPSKQSNNKYAAS SYLSLTPEQWKSHRSYSCQVTHEGSTVEKTV APTECS (SEQ ID NO: 37) | QVNLRESGGTLVQPGGSLRLSCAASGFSFTD AWMSWVRQAPGKELEWVSSISGSGGSTYYAG SVKGRFTISRDNSKNTLYLQMNSLRAEDTAV YYCARVLSLTDYYWYGMDVWGQGTLVTVSAS DDDDKTKGPSVFPLAPSSKSTSGGTAALGCL VKDYFPEPVTVSWNSGALTSGVHTFPAVLQS SGLYSLSSVVTVPSSSLGTQTYICNVNHKPS NTKVDKRVEPKSCDKTHTCPPCPAPELLGGP SVFLFPPKPKDTLMISRTPEVTCVVVDVSHE DPEVKFNWYVDGVEVHNAKTKPREEQYNSTY RVVSVLTVLHQDWLNGKEYKCKVSNKALPAP IEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 38) |

IgG-like protease-regulated antibodies against RG1 (19G9)

| | |
| --- | --- |
| EIVLTQSPGTLSLSPGERATLSCRASQSVS SSYLAWYQQKPGQAPRLLIYGASSRATGIP DRFSGSGSGTDFTLTISRLEPEDFAVYYCQ QYSSSLTFGGGTKVEIKRTSDDDDKVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC (SEQ ID NO: 39) | EVQLVQSGGGLVQPGGSLRLSCAGSGFTFS SYVMHWLRQAPGKGLEWVSVIGTGGVTHYA DSVKGRFTISRDNAKNSLYLQMNSLRAEDT AVYYCARWGYYGSGSYENDAFDIWGQGTMV TVSSADDDDDKTKGPSVFPLAPSSKSTSG GTAALGCLVKDYFPEPVTVSWNSGALTSGV HTFPAVLQSSGLYSLSSVVTVPSSSLGTQT YICNVNHKPSNTKVDKRVEPKSCDKTHTCP PCPAPELLGGPSVFLFPPKPKDTLMISRTP EVTCVVVDVSHEDPEVKFNWYVDGVEVHNA KTKPREEQYNSTYRVVSVLTVLHQDWLNGK EYKCKVSNKALPAPIEKTISKAKGQPREPQ VYTLPPSREEMTKNQVSLTCLVKGFYPSDI AVEWESNGQPENNYKTTPPVLDSDGSFFLY SKLTVDKSRWQQGNVFSCSVMHEALHNHYT QKSLSLSPGK (SEQ ID NO: 40) |

TABLE 4

PROTEASE-REGULATED ANTIBODIES (Type 2)
Fab-like protease-regulated antibodies against TF and RG1

| Light chain | Heavy chain |
|---|---|
| H1L1 | |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKE IVLTQSPGTLSLSPGERATLSCRASQSVSS SYLAWYQQKPGQAPRLLIYGASSRATGIPD RFSGSGSGTDFTLTISRLEPEDFAVYYCQQ YSSSLTFGGGTKVEIKRTVAAPSVFIFPPS DEQLKSGTASVVCLLNNFYPREAKVQWKVD NALQSGNSQESVTEQDSKDSTYSLSSTLTL SKADYEKHKVYACEVTHQGLSSPVTKSFNR GEC (SEQ ID NO: 41) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKEVQLVQSGGGLVQPGGSLRLS CAGSGFTFSSYVMHWLRQAPGKGLEWVSVI GTGGVTHYADSVKGRFTISRDNAKNSLYLQ MNSLRAEDTAVYYCARWGYYGSGSYENDAF DIWGQGTMVTVSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKKVEPKCEF (SEQ ID NO: 42) |
| H1L4 | |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKL TQSPGTLSLSPGERATLSCRASQSVSSSYL AWYQQKPGQAPRLLIYGASSRATGIPDRFS GSGSGTDFTLTISRLEPEDFAVYYCQQYSS SLTFGGGTKVEIKRTVAAPSVFIFPPSDEQ LKSGTASVVCLLNNFYPREAKVQWKVDNAL QSGNSQESVTEQDSKDSTYSLSSTLTLSKA DYEKHKVYACEVTHQGLSSPVTKSFNRGEC (SEQ ID NO: 43) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKEVQLVQSGGGLVQPGGSLRLS CAGSGFTFSSYVMHWLRQAPGKGLEWVSVI GTGGVTHYADSVKGRFTISRDNAKNSLYLQ MNSLRAEDTAVYYCARWGYYGSGSYENDAF DIWGQGTMVTVSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKKVEPKCEF (SEQ ID NO: 44) |
| H1L7 | |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKS PGTLSLSPGERATLSCRASQSVSSSYLAWY QQKPGQAPRLLIYGASSRATGIPDRFSGSG SGTDFTLTISRLEPEDFAVYYCQQYSSSLT FGGGTKVEIKRTVAAPSVFIFPPSDEQLKS GTASVVCLLNNFYPREAKVQWKVDNALQSG NSQESVTEQDSKDSTYSLSSTLTLSKADYE KHKVYACEVTHQGLSSPVTKSFNRGEC (SEQ ID NO: 45) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKEVQLVQSGGGLVQPGGSLRLS CAGSGFTFSSYVMHWLRQAPGKGLEWVSVI GTGGVTHYADSVKGRFTISRDNAKNSLYLQ MNSLRAEDTAVYYCARWGYYGSGSYENDAF DIWGQGTMVTVSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKKVEPKCEF (SEQ ID NO: 46) |
| H4L2 | |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKEIV LTQSPGTLSLSPGERATLSCRASQSVSSSY LAWYQQKPGQAPRLLIYGASSRATGIPDRF SGSGSGTDFTLTISRLEPEDFAVYYCQQYS SSLTFGGGTKVEIKRTVAAPSVFIFPPSDE QLKSGTASVVCLLNNFYPREAKVQWKVDNA LQSGNSQESVTEQDSKDSTYSLSSTLTLSK ADYEKHKVYACEVTHQGLSSPVTKSFNRGE C (SEQ ID NO: 47) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKQSGGGLVQPGGSLRLSCAGSGFTF SSYVMHWLRQAPGKGLEWVSVIGTGGVTHY ADSVKGRFTISRDNAKNSLYLQMNSLRAED TAVYYCARWGYYGSGSYENDAFDIWGQGTM VTVSSASTKGPSVFPLAPSSKSTSGGTAAL GCLVKDYFPEPVTVSWNSGALTSGVHTFPA VLQSSGLYSLSSVVTVPSSSLGTQTYICNV NHKPSNTKVDKKVEPKCEF (SEQ ID NO: 48) |
| H4L5 | |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKLTQ SPGTLSLSPGERATLSCRASQSVSSSYLAW YQQKPGQAPRLLIYGASSRATGIPDRFSGS GSGTDFTLTISRLEPEDFAVYYCQQYSSSL TFGGGTKVEIKRTVAAPSVFIFPPSDEQLK SGTASVVCLLNNFYPREAKVQWKVDNALQS | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKQSGGGLVQPGGSLRLSCAGSGFTF SSYVMHWLRQAPGKGLEWVSVIGTGGVTHY ADSVKGRFTISRDNAKNSLYLQMNSLRAED TAVYYCARWGYYGSGSYENDAFDIWGQGTM VTVSSASTKGPSVFPLAPSSKSTSGGTAAL |

TABLE 4-continued

PROTEASE-REGULATED ANTIBODIES (Type 2)
Fab-like protease-regulated antibodies against TF and RG1

| Light chain | Heavy chain |
|---|---|
| GNSQESVTEQDSKDSTYSLSSTLTLSKADY EKHKVYACEVTHQGLSSPVTKSFNRGEC (SEQ ID NO: 49) | GCLVKDYFPEPVTVSWNSGALTSGVHTFPA VLQSSGLYSLSSVVTVPSSSLGTQTYICNV NHKPSNTKVDKKVEPKCEF (SEQ ID NO: 50) |

H4L7

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKS PGTLSLSPGERATLSCRASQSVSSSYLAWY QQKPGQAPRLLIYGASSRATGIPDRFSGSG SGTDFTLTISRLEPEDFAVYYCQQYSSSLT FGGGTKVEIKRTVAAPSVFIFPPSDEQLKS GTASVVCLLNNFYPREAKVQWKVDNALQSG NSQESVTEQDSKDSTYSLSSTLTLSKADYE KHKVYACEVTHQGLSSPVTKSFNRGEC (SEQ ID NO: 51) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKQSGGGLVQPGGSLRLSCAGSGFTF SSYVMHWLRQAPGKGLEWVSVIGTGGVTHY ADSVKGRFTISRDNAKNSLYLQMNSLRAED TAVYYCARWGYYGSGSYENDAFDIWGQGTM VTVSSASTKGPSVFPLAPSSKSTSGGTAAL GCLVKDYFPEPVTVSWNSGALTSGVHTFPA VLQSSGLYSLSSVVTVPSSSLGTQTYICNV NHKPSNTKVDKKVEPKCEF (SEQ ID NO: 52) |

H5L5

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKLTQ SPGTLSLSPGERATLSCRASQSVSSSYLAW YQQKPGQAPRLLIYGASSRATGIPDRFSGS GSGTDFTLTISRLEPEDFAVYYCQQYSSSL TFGGGTKVEIKRTVAAPSVFIFPPSDEQLK SGTASVVCLLNNFYPREAKVQWKVDNALQS GNSQESVTEQDSKDSTYSLSSTLTLSKADY EKHKVYACEVTHQGLSSPVTKSFNRGEC (SEQ ID NO: 53) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKLVQPGGSLRLSCAGSGFTFSS YVMHWLRQAPGKGLEWVSVIGTGGVTHYAD SVKGRFTISRDNAKNSLYLQMNSLRAEDTA VYYCARWGYYGSGSYENDAFDIWGQGTMVT VSSASTKGPSVFPLAPSSKSTSGGTAALGC LVKDYFPEPVTVSWNSGALTSGVHTFPAVL QSSGLYSLSSVVTVPSSSLGTQTYICNVNH KPSNTKVDKKVEPKCEF (SEQ ID NO: 54) |

TABLE 5

PROTEASE-REGULATED ANTIBODIES (Type 2)
IgG-like protease-regulated antibodies against TF and RG1

| Light chain | Heavy chain |
|---|---|

3E10-Linker1-19G9

| Light chain | Heavy chain |
|---|---|
| NFMLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKE IVLTQSPGTLSLSPGERATLSCRASQSVSS SYLAWYQQKPGQAPRLLIYGASSRATGIPD RFSGSGSGTDFTLTISRLEPEDFAVYYCQQ YSSSLTFGGGTKVEIKRTVAAPSVFIFPPS DEQLKSGTASVVCLLNNFYPREAKVQWKVD NALQSGNSQESVTEQDSKDSTYSLSSTLTL SKADYEKHKVYACEVTHQGLSSPVTKSFNR GEC (SEQ ID NO: 55) | QVNLRESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKEVQLVQSGGGLVQPGGSLRLS CAGSGFTFSSYVMHWLRQAPGKGLEWVSVI GTGGVTHYADSVKGRFTISRDNAKNSLYLQ MNSLRAEDTAVYYCARWGYYGSGSYENDAF DIWGQGTMVTVSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKRVEPKSCDKTH TCPPCPAPELLGGPSVFLFPPKPKDTLMIS RTPEVTCVVVDVSHEDPEVKFNWYVDGVEV HNAKTKPREEQYNSTYRVVSVLTVLHQDWL NGKEYKCKVSNKALPAPIEKTISKAKGQPR EPQVYTLPPSREEMTKNQVSLTCLVKGFYP SDIAVEWESNGQPENNYKTTPPVLDSDGSF FLYSKLTVDKSRWQQGNVFSCSVMHEALHN HYTQKSLSLSPGK (SEQ ID NO: 56) |

3E10-Linker2-19G9

| Light chain | Heavy chain |
|---|---|
| NFMLTQPHSVSASPGKTVTISCTRSSGSVA SYYVQWYQQRPGSSPTTVIYEDNHRPSGVP | QVNLRESGGTLVQPGGSLRLSCAASGFSFT DAWMSWVRQAPGKELEWVSSISGSGGSTYY |

TABLE 5-continued

PROTEASE-REGULATED ANTIBODIES (Type 2)
IgG-like protease-regulated antibodies against TF and RG1

| Light chain | Heavy chain |
|---|---|
| DRFSGSIDTSSNSASLTISGLKTEDEADYY<br>CQSYDSNNLVVFGGGTKLTVLGAGGGGSDD<br>DDKEIVLTQSPGTLSLSPGERATLSCRASQ<br>SVSSSYLAWYQQKPGQAPRLLIYGASSRAT<br>GIPDRFSGSGSGTDFTLTISRLEPEDFAVY<br>YCQQYSSSLTFGGGTKVEIKRTVAAPSVFI<br>FPPSDEQLKSGTASVVCLLNNFYPREAKVQ<br>WKVDNALQSGNSQESVTEQDSKDSTYSLSS<br>TLTLSKADYEKHKVYACEVTHQGLSSPVTK<br>SFNRGEC<br>(SEQ ID NO: 57) | AGSVKGRFTISRDNSKNTLYLQMNSLRAED<br>TAVYYCARVLSLTDYYWYGMDVWGQGTLVT<br>VSAGGGGSDDDDKEVQLVQSGGGLVQPGGS<br>LRLSCAGSGFTFSSYVMHWLRQAPGKGLEW<br>VSVIGTGGVTHYADSVKGRFTISRDNAKNS<br>LYLQMNSLRAEDTAVYYCARWGYYGSGSYE<br>NDAFDIWGQGTMVTVSSASTKGPSVFPLAP<br>SSKSTSGGTAALGCLVKDYFPEPVTVSWNS<br>GALTSGVHTFPAVLQSSGLYSLSSVVTVPS<br>SSLGTQTYICNVNHKPSNTKVDKRVEPKSC<br>DKTHTCPPCPAPELLGGPSVFLFPPKPKDT<br>LMISRTPEVTCVVVDVSHEDPEVKFNWYVD<br>GVEVHNAKTKPREEQYNSTYRVVSVLTVLH<br>QDWLNGKEYKCKVSNKALPAPIEKTISKAK<br>GQPREPQVYTLPPSREEMTKNQVSLTCLVK<br>GFYPSDIAVEWESNGQPENNYKTTPPVLDS<br>DGSFFLYSKLTVDKSRWQQGNVFSCSVMHE<br>ALHNHYTQKSLSLSPGK<br>(SEQ ID NO: 58) |

3E10-Linker3-19G9

| Light chain | Heavy chain |
|---|---|
| NFMLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGAGGGGSDD<br>DDKGGGGSEIVLTQSPGTLSLSPGERATLS<br>CRASQSVSSSYLAWYQQKPGQAPRLLIYGA<br>SSRATGIPDRFSGSGSGTDFTLTISRLEPE<br>DFAVYYCQQYSSSLTFGGGTKVEIKRTVAA<br>PSVFIFPPSDEQLKSGTASVVCLLNNFYPR<br>EAKVQWKVDNALQSGNSQESVTEQDSKDST<br>YSLSSTLTLSKADYEKHKVYACEVTHQGLS<br>SPVTKSFNRGEC<br>(SEQ ID NO: 59) | QVNLRESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VSAGGGGSDDDDKGGGGSEVQLVQSGGGLV<br>QPGGSLRLSCAGSGFTFSSYVMHWLRQAPG<br>KGLEWVSVIGTGGVTHYADSVKGRFTISRD<br>NAKNSLYLQMNSLRAEDTAVYYCARWGYYG<br>SGSYENDAFDIWGQGTMVTVSSASTKGPSV<br>FPLAPSSKSTSGGTAALGCLVKDYFPEPVT<br>VSWNSGALTSGVHTFPAVLQSSGLYSLSSV<br>VTVPSSSLGTQTYICNVNHKPSNTKVDKRV<br>EPKSCDKTHTCPPCPAPELLGGPSVFLFPP<br>KPKDTLMISRTPEVTCVVVDVSHEDPEVKF<br>NWYVDGVEVHNAKTKPREEQYNSTYRVVSV<br>LTVLHQDWLNGKEYKCKVSNKALPAPIEKT<br>ISKAKGQPREPQVYTLPPSREEMTKNQVSL<br>TCLVKGFYPSDIAVEWESNGQPENNYKTTP<br>PVLDSDGSFFLYSKLTVDKSRWQQGNVFSC<br>SVMHEALHNHYTQKSLSLSPGK<br>(SEQ ID NO: 60) |

3E10-Linker4-19G9

| Light chain | Heavy chain |
|---|---|
| NFMLTQPHSVSASPGKTVTISCTRSSGSVASYYVQ<br>WYQQRPGSSPTTVIYEDNHRPSGVPDRFSGSIDTS<br>SNSASLTISGLKTEDEADYYCQSYDSNNLVVFGGG<br>TKLTVLGAGGGGSGGGGSGGGGSEIVLTQSPGTLS<br>LSPGERATLSCRASQSVSSSYLAWYQQKPGQAPRL<br>LIYGASSRATGIPDRFSGSGSGTDFTLTISRLEPE<br>DFAVYYCQQYSSSLTFGGGTKVEIKRTVAAPSVFI<br>FPPSDEQLKSGTASVVCLLNNFYPREAKVQWKVDN<br>ALQSGNSQESVTEQDSKDSTYSLSSTLTLSKADYE<br>KHKVYACEVTHQGLSSPVTKSFNRGEC<br>(SEQ ID NO: 61) | QVNLRESGGTLVQPGGSLRLSCAASGFSFTDAWMS<br>WVRQAPGKELEWVSSISGSGGSTYYAGSVKGRFTI<br>SRDNSKNTLYLQMNSLRAEDTAVYYCARVLSLTDY<br>YWYGMDVWGQGTLVTVSAGGGGSGGGGSGGGGSEV<br>QLVQSGGGLVQPGGSLRLSCAGSGFTFSSYVMHWL<br>RQAPGKGLEWVSVIGTGGVTHYADSVKGRFTISRD<br>NAKNSLYLQMNSLRAEDTAVYYCARWGYYGSGSYE<br>NDAFDIWGQGTMVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHK<br>PSNTKVDKRVEPKSCDKTHTCPPCPAPELLGGPSV<br>FLFPPKPKDTLMISRTPEVTCVVVDVSHEDPEVKF<br>NWYVDGVEVHNAKTKPREEQYNSTYRVVSVLTVLH<br>QDWLNGKEYKCKVSNKALPAPIEKTISKAKGQPRE<br>PQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK<br>(SEQ ID NO: 62) |

3E10-Link1-19G9 Fab

| Light chain | Heavy chain |
|---|---|
| DIVLTQPHSVSASPGKTVTISCTRSSGSVASYYVQ<br>WYQQRPGSSPTTVIYEDNHRPSGVPDRFSGSIDTS<br>SNSASLTISGLKTEDEADYYCQSYDSNNLVVFGGG<br>TKLTVLGASDDDDKEIVLTQSPGTLSLSPGERATL<br>SCRASQSVSSSYLAWYQQKPGQAPRLLIYGASSRA<br>TGIPDRFSGSGSGTDFTLTISRLEPEDFAVYYCQQ<br>YSSSLTFGGGTKVEIKRTVAAPSVFIFPPSDEQLK<br>SGTASVVCLLNNFYPREAKVQWKVDNALQSGNSQE | QVQLVESGGTLVQPGGSLRLSCAASGFSFTDAWMS<br>WVRQAPGKELEWVSSISGSGGSTYYAGSVKGRFTI<br>SRDNSKNTLYLQMNSLRAEDTAVYYCARVLSLTDY<br>YWYGMDVWGQGTLVTVSASDDDDKEVQLVQSGGGL<br>VQPGGSLRLSCAGSGFTFSSYVMHWLRQAPGKGLE<br>WVSVIGTGGVTHYADSVKGRFTISRDNAKNSLYLQ<br>MNSLRAEDTAVYYCARWGYYGSGSYENDAFDIWGQ<br>GTMVTVSSASTKGPSVFPLAPSSKSTSGGTAALGC |

TABLE 5-continued

PROTEASE-REGULATED ANTIBODIES (Type 2)
IgG-like protease-regulated antibodies against TF and RG1

| Light chain | Heavy chain |
| --- | --- |
| SVTEQDSKDSTYSLSSTLTLSKADYEKHKVYACEV THQGLSSPVTKSFNRGEA (SEQ ID NO: 63) | LVKDYFPEPVTVSWNSGALTSGVHTFPAVLQSSGL YSLSSVVTVPSSSLGTQTYICNVNHKPSNTKVDKK VEPKSEF (SEQ ID NO: 64) |

TABLE 6

PROTEASE-REGULATED ANTIBODIES (Type 3)
Fab-like protease-regulated antibodies

| Light chain | Heavy chain |
| --- | --- |

H1L5

| Light chain | Heavy chain |
| --- | --- |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKLTQ SPGTLSLSPGERATLSCRASQSVSSSYLAW YQQKPGQAPRLLIYGASSRATGIPDRFSGS GSGTDFTLTISRLEPEDFAVYYCQQYSSSL TFGGGTKVEIKRTVAAPSVFIFPPSDEQLK SGTASVVCLLNNFYPREAKVQWKVDNALQS GNSQESVTEQDSKDSTYSLSSTLTLSKADY EKHKVYACEVTHQGLSSPVTKSFNRGEC (SEQ ID NO: 65) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKEVQLVQSGGGLVQPGGSLRLS CAGSGFTFSSYVMHWLRQAPGKGLEWVSVI GTGGVTHYADSVKGRFTISRDNAKNSLYLQ MNSLRAEDTAVYYCARWGYYGSGSYENDAF DIWGQGTMVTVSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKKVEPKCEF (SEQ ID NO: 66) |

H2L1

| Light chain | Heavy chain |
| --- | --- |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKE IVLTQSPGTLSLSPGERATLSCRASQSVSS SYLAWYQQKPGQAPRLLIYGASSRATGIPD RFSGSGSGTDFTLTISRLEPEDFAVYYCQQ YSSSLTFGGGTKVEIKRTVAAPSVFIFPPS DEQLKSGTASVVCLLNNFYPREAKVQWKVD NALQSGNSQESVTEQDSKDSTYSLSSTLTL SKADYEKHKVYACEVTHQGLSSPVTKSFNR GEC (SEQ ID NO: 67) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKEVQLVQSGGGLVQPGGSLRLSCAG SGFTFSSYVMHWLRQAPGKGLEWVSVIGTG GVTHYADSVKGRFTISRDNAKNSLYLQMNS LRAEDTAVYYCARWGYYGSGSYENDAFDIW GQGTMVTVSSASTKGPSVFPLAPSSKSTSG GTAALGCLVKDYFPEPVTVSWNSGALTSGV HTFPAVLQSSGLYSLSSVVTVPSSSLGTQT YICNVNHKPSNTKVDKKVEPKCEF (SEQ ID NO: 68) |

H2L2

| Light chain | Heavy chain |
| --- | --- |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKEIV LTQSPGTLSLSPGERATLSCRASQSVSSSY LAWYQQKPGQAPRLLIYGASSRATGIPDRF SGSGSGTDFTLTISRLEPEDFAVYYCQQYS SSLTFGGGTKVEIKRTVAAPSVFIFPPSDE QLKSGTASVVCLLNNFYPREAKVQWKVDNA LQSGNSQESVTEQDSKDSTYSLSSTLTLSK ADYEKHKVYACEVTHQGLSSPVTKSFNRGE C (SEQ ID NO: 69) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKEVQLVQSGGGLVQPGGSLRLSCAG SGFTFSSYVMHWLRQAPGKGLEWVSVIGTG GVTHYADSVKGRFTISRDNAKNSLYLQMNS LRAEDTAVYYCARWGYYGSGSYENDAFDIW GQGTMVTVSSASTKGPSVFPLAPSSKSTSG GTAALGCLVKDYFPEPVTVSWNSGALTSGV HTFPAVLQSSGLYSLSSVVTVPSSSLGTQT YICNVNHKPSNTKVDKKVEPKCEF (SEQ ID NO: 70) |

H2L4

| Light chain | Heavy chain |
| --- | --- |
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASASDDDD KLTQSPGTLSLSPGERATLSCRASQSVSSS YLAWYQQKPGQAPRLLIYGASSRATGIPDR FSGSGSGTDFTLTISRLEPEDFAVYYCQQY SSSLTFGGGTKVEIKRTVAAPSVFIFPPSD EQLKSGTASVVCLLNNFYPREAKVQWKVDN ALQSGNSQESVTEQDSKDSTYSLSSTLTLS | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VDDDDKEVQLVQSGGGLVQPGGSLRLSCAG SGFTFSSYVMHWLRQAPGKGLEWVSVIGTG GVTHYADSVKGRFTISRDNAKNSLYLQMNS LRAEDTAVYYCARWGYYGSGSYENDAFDIW GQGTMVTVSSASTKGPSVFPLAPSSKSTSG GTAALGCLVKDYFPEPVTVSWNSGALTSGV |

TABLE 6-continued

PROTEASE-REGULATED ANTIBODIES (Type 3)
Fab-like protease-regulated antibodies

| Light chain | Heavy chain |
|---|---|
| KADYEKHKVYACEVTHQGLSSPVTKSFNRG<br>EC<br>(SEQ ID NO: 71) | HTFPAVLQSSGLYSLSSVVTVPSSSLGTQT<br>YICNVNHKPSNTKVDKKVEPKCEF<br>(SEQ ID NO: 72) |

H2L5

| Light chain | Heavy chain |
|---|---|
| DIVLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGDDDDKLTQ<br>SPGTLSLSPGERATLSCRASQSVSSSYLAW<br>YQQKPGQAPRLLIYGASSRATGIPDRFSGS<br>GSGTDFTLTISRLEPEDFAVYYCQQYSSSL<br>TFGGGTKVEIKRTVAAPSVFIFPPSDEQLK<br>SGTASVVCLLNNFYPREAKVQWKVDNALQS<br>GNSQESVTEQDSKDSTYSLSSTLTLSKADY<br>EKHKVYACEVTHQGLSSPVTKSFNRGEC<br>(SEQ ID NO: 73) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG<br>GTAALGCLVKDYFPEPVTVSWNSGALTSGV<br>HTFPAVLQSSGLYSLSSVVTVPSSSLGTQT<br>YICNVNHKPSNTKVDKKVEPKCEF<br>(SEQ ID NO: 74) |

H2L7

| Light chain | Heavy chain |
|---|---|
| DIVLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGASDDDDKS<br>PGTLSLSPGERATLSCRASQSVSSSYLAWY<br>QQKPGQAPRLLIYGASSRATGIPDRFSGSG<br>SGTDFTLTISRLEPEDFAVYYCQQYSSSLT<br>FGGGTKVEIKRTVAAPSVFIFPPSDEQLKS<br>GTASVVCLLNNFYPREAKVQWKVDNALQSG<br>NSQESVTEQDSKDSTYSLSSTLTLSKADYE<br>KHKVYACEVTHQGLSSPVTKSFNRGEC<br>(SEQ ID NO: 75) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG<br>GTAALGCLVKDYFPEPVTVSWNSGALTSGV<br>HTFPAVLQSSGLYSLSSVVTVPSSSLGTQT<br>YICNVNHKPSNTKVDKKVEPKCEF<br>(SEQ ID NO: 76) |

H2L8

| Light chain | Heavy chain |
|---|---|
| DIVLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGDDDDKSPG<br>TLSLSPGERATLSCRASQSVSSSYLAWYQQ<br>KPGQAPRLLIYGASSRATGIPDRFSGSGSG<br>TDFTLTISRLEPEDFAVYYCQQYSSSLTFG<br>GGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKH<br>KVYACEVTHQGLSSPVTKSFNRGEC<br>(SEQ ID NO: 77) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG<br>GTAALGCLVKDYFPEPVTVSWNSGALTSGV<br>HTFPAVLQSSGLYSLSSVVTVPSSSLGTQT<br>YICNVNHKPSNTKVDKKVEPKCEF<br>(SEQ ID NO: 78) |

TABLE 7

PROTEASE-REGULATED ANTIBODIES (Type 3)
IgG-like protease-regulated antibodies

| Light chain | Heavy chain |
|---|---|
| 3E10-Linker1 a-19G9 | |

| Light chain | Heavy chain |
|---|---|
| NFMLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVSDDDDKEIVL<br>TQSPGTLSLSPGERATLSCRASQSVSSSYL<br>AWYQQKPGQAPRLLIYGASSRATGIPDRFS<br>GSGSGTDFTLTISRLEPEDFAVYYCQQYSS<br>SLTFGGGTKVEIKRTVAAPSVFIFPPSDEQ<br>LKSGTASVVCLLNNFYPREAKVQWKVDNAL | QVNLRESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG |

TABLE 7-continued

PROTEASE-REGULATED ANTIBODIES (Type 3)
IgG-like protease-regulated antibodies

| Light chain | Heavy chain |
| --- | --- |
| QSGNSQESVTEQDSKDSTYSLSSTLTLSKA<br>DYEKHKVYACEVTHQGLSSPVTKSFNRGEC<br>(SEQ ID NO: 79) | GTAALGCLVKDYFPEPVTVSWNSGALTSGV<br>HTFPAVLQSSGLYSLSSVVTVPSSSLGTQT<br>YICNVNHKPSNTKVDKRVEPKSCDKTHTCP<br>PCPAPELLGGPSVFLFPPKPKDTLMISRTP<br>EVTCVVVDVSHEDPEVKFNWYVDGVEVHNA<br>KTKPREEQYNSTYRVVSVLTVLHQDWLNGK<br>EYKCKVSNKALPAPIEKTISKAKGQPREPQ<br>VYTLPPSREEMTKNQVSLTCLVKGFYPSDI<br>AVEWESNGQPENNYKTTPPVLDSDGSFFLY<br>SKLTVDKSRWQQGNVFSCSVMHEALHNHYT<br>QKSLSLSPGK<br>(SEQ ID NO: 80) |

3E10-Linker1b-19G9

| Light chain | Heavy chain |
| --- | --- |
| NFMLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVSDDDDKLTQS<br>PGTLSLSPGERATLSCRASQSVSSSYLAWY<br>QQKPGQAPRLLIYGASSRATGIPDRFSGSG<br>SGTDFTLTISRLEPEDFAVYYCQQYSSSLT<br>FGGGTKVEIKRTVAAPSVFIFPPSDEQLKS<br>GTASVVCLLNNFYPREAKVQWKVDNALQSG<br>NSQESVTEQDSKDSTYSLSSTLTLSKADYE<br>KHKVYACEVTHQGLSSPVTKSFNRGEC<br>(SEQ ID NO: 81) | QVNLRESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKQSGGGLVQPGGSLRLSCAGSGFTF<br>SSYVMHWLRQAPGKGLEWVSVIGTGGVTHY<br>ADSVKGRFTISRDNAKNSLYLQMNSLRAED<br>TAVYYCARWGYYGSGSYENDAFDIWGQGTM<br>VTVSSASTKGPSVFFLAPSSKSTSGGTAAL<br>GCLVKDYFPEPVTVSWNSGALTSGVHTFPA<br>VLQSSGLYSLSSVVTVPSSSLGTQTYICNV<br>NHKPSNTKVDKRVEPKSCDKTHTCPPCPAP<br>ELLGGPSVFLFPPKPKDTLMISRTPEVTCV<br>VVDVSHEDPEVKFNWYVDGVEVHNAKTKPR<br>EEQYNSTYRVVSVLTVLHQDWLNGKEYKCK<br>VSNKALPAPIEKTISKAKGQPREPQVYTLP<br>PSREEMTKNQVSLTCLVKGFYPSDIAVEWE<br>SNGQPENNYKTTPPVLDSDGSFFLYSKLTV<br>DKSRWQQGNVFSCSVMHEALHNHYTQKSLS<br>LSPGK<br>(SEQ ID NO: 82) |

3E10-Linker1c-19G9

| Light chain | Heavy chain |
| --- | --- |
| NFMLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGASDDDDKL<br>TQSPGTLSLSPGERATLSCRASQSVSSSYL<br>AWYQQKPGQAPRLLIYGASSRATGIPDRFS<br>GSGSGTDFTLTISRLEPEDFAVYYCQQYSS<br>SLTFGGGTKVEIKRTVAAPSVFIFPPSDEQ<br>LKSGTASVVCLLNNFYPREAKVQWKVDNAL<br>QSGNSQESVTEQDSKDSTYSLSSTLTLSKA<br>DYEKHKVYACEVTHQGLSSPVTKSFNRGEC<br>(SEQ ID NO: 83) | QVNLRESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VSASDDDDKQSGGGLVQPGGSLRLSCAGSG<br>FTFSSYVMHWLRQAPGKGLEWVSVIGTGGV<br>THYADSVKGRFTISRDNAKNSLYLQMNSLR<br>AEDTAVYYCARWGYYGSGSYENDAFDIWGQ<br>GTMVTVSSASTKGPSVFPLAPSSKSTSGGT<br>AALGCLVKDYFPEPVTVSWNSGALTSGVHT<br>FPAVLQSSGLYSLSSVVTVPSSSLGTQTYI<br>CNVNHKPSNTKVDKRVEPKSCDKTHTCPPC<br>PAPELLGGPSVFLFPPKPKDTLMISRTPEV<br>TCVVVDVSHEDPEVKFNWYVDGVEVHNAKT<br>KPREEQYNSTYRVVSVLTVLHQDWLNGKEY<br>KCKVSNKALPAPIEKTISKAKGQPREPQVY<br>TLPPSREEMTKNQVSLTCLVKGFYPSDIAV<br>EWESNGQPENNYKTTPPVLDSDGSFFLYSK<br>LTVDKSRWQQGNVFSCSVMHEALHNHYTQK<br>SLSLSPGK<br>(SEQ ID NO: 84) |

TABLE 8

PROTEASE-REGULATED ANTIBODIES (Type 4)

| Light chain | Heavy chain |
| --- | --- |
| | H3L1 |
| DIVLTQPHSVSASPGKTVTISCTRSSGSVA<br>SYYVQWYQQRPGSSPTTVIYEDNHRPSGVP<br>DRFSGSIDTSSNSASLTISGLKTEDEADYY | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED |

TABLE 8-continued

PROTEASE-REGULATED ANTIBODIES (Type 4)

| Light chain | Heavy chain |
|---|---|
| CQSYDSNNLVVFGGGTKLTVLGASDDDDKE IVLTQSPGTLSLSPGERATLSCRASQSVSS SYLAWYQQKPGQAPRLLIYGASSRATGIPD RFSGSGSGTDFTLTISRLEPEDFAVYYCQQ YSSSLTFGGGTKVEIKRTVAAPSVFIFPPS DEQLKSGTASVVCLLNNFYPREAKVQWKVD NALQSGNSQESVTEQDSKDSTYSLSSTLTL SKADYEKHKVYACEVTHQGLSSPVTKSFNR GEC (SEQ ID NO: 85) | TAVYYCARVLSLTDYYWYGMDVWGQGTLVT VSASDDDDKQSGGGLVQPGGSLRLSCAGSG FTFSSYVMHWLRQAPGKGLEWVSVIGTGGV THYADSVKGRFTISRDNAKNSLYLQMNSLR AEDTAVYYCARWGYYGSGSYENDAFDIWGQ GTMVTVSSASTKGPSVFPLAPSSKSTSGGT AALGCLVKDYFPEPVTVSWNSGALTSGVHT FPAVLQSSGLYSLSSVVTVPSSSLGTQTYI CNVNHKPSNTKVDKKVEPKCEF (SEQ ID NO: 86) |

H3L2

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKEIV LTQSPGTLSLSPGERATLSCRASQSVSSSY LAWYQQKPGQAPRLLIYGASSRATGIPDRF SGSGSGTDFTLTISRLEPEDFAVYYCQQYS SSLTFGGGTKVEIKRTVAAPSVFIFPPSDE QLKSGTASVVCLLNNFYPREAKVQWKVDNA LQSGNSQESVTEQDSKDSTYSLSSTLTLSK ADYEKHKVYACEVTHQGLSSPVTKSFNRGE C (SEQ ID NO: 87) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKQSGGGLVQPGGSLRLSCAGSG FTFSSYVMHWLRQAPGKGLEWVSVIGTGGV THYADSVKGRFTISRDNAKNSLYLQMNSLR AEDTAVYYCARWGYYGSGSYENDAFDIWGQ GTMVTVSSASTKGPSVFPLAPSSKSTSGGT AALGCLVKDYFPEPVTVSWNSGALTSGVHT FPAVLQSSGLYSLSSVVTVPSSSLGTQTYI CNVNHKPSNTKVDKKVEPKCEF (SEQ ID NO: 88) |

H3L4

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKL TQSPGTLSLSPGERATLSCRASQSVSSSYL AWYQQKPGQAPRLLIYGASSRATGIPDRFS GSGSGTDFTLTISRLEPEDFAVYYCQQYSS SLTFGGGTKVEIKRTVAAPSVFIFPPSDEQ LKSGTASVVCLLNNFYPREAKVQWKVDNAL QSGNSQESVTEQDSKDSTYSLSSTLTLSKA DYEKHKVYACEVTHQGLSSPVTKSFNRGEC (SEQ ID NO: 89) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKQSGGGLVQPGGSLRLSCAGSG FTFSSYVMHWLRQAPGKGLEWVSVIGTGGV THYADSVKGRFTISRDNAKNSLYLQMNSLR AEDTAVYYCARWGYYGSGSYENDAFDIWGQ GTMVTVSSASTKGPSVFPLAPSSKSTSGGT AALGCLVKDYFPEPVTVSWNSGALTSGVHT FPAVLQSSGLYSLSSVVTVPSSSLGTQTYI CNVNHKPSNTKVDKKVEPKCEF (SEQ ID NO: 90) |

H3L5

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGDDDDKLTQ SPGTLSLSPGERATLSCRASQSVSSSYLAW YQQKPGQAPRLLIYGASSRATGIPDRFSGS GSGTDFTLTISRLEPEDFAVYYCQQYSSSL TFGGGTKVEIKRTVAAPSVFIFPPSDEQLK SGTASVVCLLNNFYPREAKVQWKVDNALQS GNSQESVTEQDSKDSTYSLSSTLTLSKADY EKHKVYACEVTHQGLSSPVTKSFNRGEC (SEQ ID NO: 91) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKQSGGGLVQPGGSLRLSCAGSG FTFSSYVMHWLRQAPGKGLEWVSVIGTGGV THYADSVKGRFTISRDNAKNSLYLQMNSLR AEDTAVYYCARWGYYGSGSYENDAFDIWGQ GTMVTVSSASTKGPSVFPLAPSSKSTSGGT AALGCLVKDYFPEPVTVSWNSGALTSGVHT FPAVLQSSGLYSLSSVVTVPSSSLGTQTYI CNVNHKPSNTKVDKKVEPKCEF (SEQ ID NO: 92) |

H3L7

| Light chain | Heavy chain |
|---|---|
| DIVLTQPHSVSASPGKTVTISCTRSSGSVA SYYVQWYQQRPGSSPTTVIYEDNHRPSGVP DRFSGSIDTSSNSASLTISGLKTEDEADYY CQSYDSNNLVVFGGGTKLTVLGASDDDDKS PGTLSLSPGERATLSCRASQSVSSSYLAWY QQKPGQAPRLLIYGASSRATGIPDRFSGSG SGTDFTLTISRLEPEDFAVYYCQQYSSSLT FGGGTKVEIKRTVAAPSVFIFPPSDEQLKS GTASVVCLLNNFYPREAKVQWKVDNALQSG NSQESVTEQDSKDSTYSLSSTLTLSKADYE KHKVYACEVTHQGLSSPVTKSFNRGEC (SEQ ID NO: 93) | QVQLVESGGTLVQPGGSLRLSCAASGFSFT DAWMSWVRQAPGKELEWVSSISGSGGSTYY AGSVKGRFTISRDNSKNTLYLQMNSLRAED TAVYYCARVLSLTDYYWYGMDVWGQGTLVT VSASDDDDKQSGGGLVQPGGSLRLSCAGSG FTFSSYVMHWLRQAPGKGLEWVSVIGTGGV THYADSVKGRFTISRDNAKNSLYLQMNSLR AEDTAVYYCARWGYYGSGSYENDAFDIWGQ GTMVTVSSASTKGPSVFPLAPSSKSTSGGT AALGCLVKDYFPEPVTVSWNSGALTSGVHT FPAVLQSSGLYSLSSVVTVPSSSLGTQTYI CNVNHKPSNTKVDKKVEPKCEF (SEQ ID NO: 94) |

TABLE 8-continued

PROTEASE-REGULATED ANTIBODIES (Type 4)

| Light chain | Heavy chain |
|---|---|

H1L2

DIVLTQPHSVSASPGKTVTISCTRSSGSVA
SYYVQWYQQRPGSSPTTVIYEDNHRPSGVP
DRFSGSIDTSSNSASLTISGLKTEDEADYY
CQSYDSNNLVVFGGGTKLTVLGDDDDKEIV
LTQSPGTLSLSPGERATLSCRASQSVSSSY
LAWYQQKPGQAPRLLIYGASSRATGIPDRF
SGSGSGTDFTLTISRLEPEDFAVYYCQQYS
SSLTFGGGTKVEIKRTVAAPSVFIFPPSDE
QLKSGTASVVCLLNNFYPREAKVQWKVDNA
LQSGNSQESVTEQDSKDSTYSLSSTLTLSK
ADYEKHKVYACEVTHQGLSSPVTKSFNRGE
C
(SEQ ID NO: 95)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARVLSLTDYYWYGMDVWGQGTLVT
VSASDDDDKEVQLVQSGGGLVQPGGSLRLS
CAGSGFTFSSYVMHWLRQAPGKGLEWVSVI
GTGGVTHYADSVKGRFTISRDNAKNSLYLQ
MNSLRAEDTAVYYCARWGYYGSGSYENDAF
DIWGQGTMVTVSSASTKGPSVFPLAPSSKS
TSGGTAALGCLVKDYFPEPVTVSWNSGALT
SGVHTFPAVLQSSGLYSLSSVVTVPSSSLG
TQTYICNVNHKPSNTKVDKKVEPKCEF
(SEQ ID NO: 96)

H5L1

DIVLTQPHSVSASPGKTVTISCTRSSGSVA
SYYVQWYQQRPGSSPTTVIYEDNHRPSGVP
DRFSGSIDTSSNSASLTISGLKTEDEADYY
CQSYDSNNLVVFGGGTKLTVLGASDDDDKE
IVLTQSPGTLSLSPGERATLSCRASQSVSS
SYLAWYQQKPGQAPRLLIYGASSRATGIPD
RFSGSGSGTDFTLTISRLEPEDFAVYYCQQ
YSSSLTFGGGTKVEIKRTVAAPSVFIFPPS
DEQLKSGTASVVCLLNNFYPREAKVQWKVD
NALQSGNSQESVTEQDSKDSTYSLSSTLTL
SKADYEKHKVYACEVTHQGLSSPVTKSFNR
GEC
(SEQ ID NO: 97)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARVLSLTDYYWYGMDVWGQGTLVT
VSASDDDDKLVQPGGSLRLSCAGSGFTFSS
YVMHWLRQAPGKGLEWVSVIGTGGVTHYAD
SVKGRFTISRDNAKNSLYLQMNSLRAEDTA
VYYCARWGYYGSGSYENDAFDIWGQGTMVT
VSSASTKGPSVFPLAPSSKSTSGGTAALGC
LVKDYFPEPVTVSWNSGALTSGVHTFPAVL
QSSGLYSLSSVVTVPSSSLGTQTYICNVNH
KPSNTKVDKKVEPKCEF
(SEQ ID NO: 98)

H5L4

DIVLTQPHSVSASPGKTVTISCTRSSGSVA
SYYVQWYQQRPGSSPTTVIYEDNHRPSGVP
DRFSGSIDTSSNSASLTISGLKTEDEADYY
CQSYDSNNLVVFGGGTKLTVLGASDDDDKL
TQSPGTLSLSPGERATLSCRASQSVSSSYL
AWYQQKPGQAPRLLIYGASSRATGIPDRFS
GSGSGTDFTLTISRLEPEDFAVYYCQQYSS
SLTEGGGTKVEIKRTVAAPSVFIFPPSDEQ
LKSGTASVVCLLNNFYPREAKVQWKVDNAL
QSGNSQESVTEQDSKDSTYSLSSTLTLSKA
DYEKHKVYACEVTHQGLSSPVTKSFNRGEC
(SEQ ID NO: 99)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARVLSLTDYYWYGMDVWGQGTLVT
VSASDDDDKLVQPGGSLRLSCAGSGFTFSS
YVMHWLRQAPGKGLEWVSVIGTGGVTHYAD
SVKGRFTISRDNAKNSLYLQMNSLRAEDTA
VYYCARWGYYGSGSYENDAFDIWGQGTMVT
VSSASTKGPSVFPLAPSSKSTSGGTAALGC
LVKDYFPEPVTVSWNSGALTSGVHTFPAVL
QSSGLYSLSSVVTVPSSSLGTQTYICNVNH
KPSNTKVDKKVEPKCEF
(SEQ ID NO: 100)

H5L7

DIVLTQPHSVSASPGKTVTISCTRSSGSVA
SYYVQWYQQRPGSSPTTVIYEDNHRPSGVP
DRFSGSIDTSSNSASLTISGLKTEDEADYY
CQSYDSNNLVVFGGGTKLTVLGASDDDDKS
PGTLSLSPGERATLSCRASQSVSSSYLAWY
QQKPGQAPRLLIYGASSRATGIPDRFSGSG
SGTDFTLTISRLEPEDFAVYYCQQYSSSLT
FGGGTKVEIKRTVAAPSVFIFPPSDEQLKS
GTASVVCLLNNFYPREAKVQWKVDNALQSG
NSQESVTEQDSKDSTYSLSSTLTLSKADYE
KHKVYACEVTHQGLSSPVTKSFNRGEC
(SEQ ID NO: 101)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARVLSLTDYYWYGMDVWGQGTLVT
VSASDDDDKLVQPGGSLRLSCAGSGFTFSS
YVMHWLRQAPGKGLEWVSVIGTGGVTHYAD
SVKGRFTISRDNAKNSLYLQMNSLRAEDTA
VYYCARWGYYGSGSYENDAFDIWGQGTMVT
VSSASTKGPSVFPLAPSSKSTSGGTAALGC
LVKDYFPEPVTVSWNSGALTSGVHTFPAVL
QSSGLYSLSSVVTVPSSSLGTQTYICNVNH
KPSNTKVDKKVEPKCEF
(SEQ ID NO: 102)

H5L8

DIVLTQPHSVSASPGKTVTISCTRSSGSVA
SYYVQWYQQRPGSSPTTVIYEDNHRPSGVP
DRFSGSIDTSSNSASLTISGLKTEDEADYY
CQSYDSNNLVVFGGGTKLTVLGDDDDKSPG
TLSLSPGERATLSCRASQSVSSSYLAWYQQ
KPGQAPRLLIYGASSRATGIPDRFSGSGSG
TDFTLTISRLEPEDFAVYYCQQYSSSLTFG
GGTKVEIKRTVAAPSVFIFPPSDEQLKSGT
ASVVCLLNNFYPREAKVQWKVDNALQSGNS

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARVLSLTDYYWYGMDVWGQGTLVT
VSASDDDDKLVQPGGSLRLSCAGSGFTFSS
YVMHWLRQAPGKGLEWVSVIGTGGVTHYAD
SVKGRFTISRDNAKNSLYLQMNSLRAEDTA
VYYCARWGYYGSGSYENDAFDIWGQGTMVT
VSSASTKGPSVFPLAPSSKSTSGGTAALGC

TABLE 8-continued

PROTEASE-REGULATED ANTIBODIES (Type 4)

| Light chain | Heavy chain |
|---|---|
| QESVTEQDSKDSTYSLSSTLTLSKADYEKH<br>KVYACEVTHQGLSSPVTKSFNRGEC<br>(SEQ ID NO: 103) | LVKDYFPEPVTVSWNSGALTSGVHTFPAVL<br>QSSGLYSLSSVVTVPSSSLGTQTYICNVNH<br>KPSNTKVDKKVEPKCEF<br>(SEQ ID NO: 104) |

H6L1

| | |
|---|---|
| DIVLTQPHSVSASPGKTVTISCTRSSGSVA<br>SYYVQWYQQRPGSSPTTVIYEDNHRPSGVP<br>DRFSGSIDTSSNSASLTISGLKTEDEADYY<br>CQSYDSNNLVVFGGGTKLTVLGASDDDDKE<br>IVLTQSPGTLSLSPGERATLSCRASQSVSS<br>SYLAWYQQKPGQAPRLLIYGASSRATGIPD<br>RFSGSGSGTDFTLTISRLEPEDFAVYYCQQ<br>YSSSLTFGGGTKVEIKRTVAAPSVFIFPPS<br>DEQLKSGTASVVCLLNNFYPREAKVQWKVD<br>NALQSGNSQESVTEQDSKDSTYSLSSTLTL<br>SKADYEKHKVYACEVTHQGLSSPVTKSFNR<br>GEC<br>(SEQ ID NO: 105) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARVLSLTDYYWYGMDVWGQGTLVT<br>VDDDDKLVQPGGSLRLSCAGSGFTFSSYVM<br>HWLRQAPGKGLEWVSVIGTGGVTHYADSVK<br>GRFTISRDNAKNSLYLQNNSLRAEDTAVYY<br>CARWGYYGSGSYENDAFDIWGQGTMVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKCEF<br>(SEQ ID NO: 106) |

TABLE 9

PROTEASE-REGULATED ANTIBODIES (Type 4)

| Heavy chain | Heavy chain |
|---|---|

H1L5a

| | |
|---|---|
| QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VSASDDDDKEVQLVQSGGGLVQPGGSLRLS<br>CAGSGFTFSSYVMHWLRQAPGKGLEWVSVI<br>GTGGVTHYADSVKGRFTISRDNAKNSLYLQ<br>MNSLRAEDTAVYYCARWGYYGSGSYENDAF<br>DIWGQGTMVTVSSASTKGPSVFPLAPSSKS<br>TSGGTAALGCLVKDYFPEPVTVSWNSGALT<br>SGVHTFPAVLQSSGLYSLSSVVTVPSSSLG<br>TQTYICNVNHKPSNTKVDKKVEPKCEF<br>(SEQ ID NO: 107) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VSASDDDDKEVQLVQSGGGLVQPGGSLRLS<br>CAGSGFTFSSYVMHWLRQAPGKGLEWVSVI<br>GTGGVTHYADSVKGRFTISRDNAKNSLYLQ<br>MNSLRAEDTAVYYCARWGYYGSGSYENDAF<br>DIWGQGTMVTVSSASTKGPSVFPLAPSSKS<br>TSGGTAALGCLVKDYFPEPVTVSWNSGALT<br>SGVHTFPAVLQSSGLYSLSSVVTVPSSSLG<br>TQTYICNVMHKPSNTICVDKICVEPKCEF<br>(SEQ ID NO: 108) |

H2L1a

| | |
|---|---|
| QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG<br>GTAALGCLVKDYFPEPVTVSWNSGALTSGV<br>HTFPAVLQSSGLYSLSSVVTVPSSSLGTQT<br>YICNVNHKPSNTKVDKKVEPKCEF<br>(SEQ ID NO: 109) | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG<br>GTAALGCLVKDYFPEPVTVSWNSGALTSGV<br>HTFPAVLQSSGLYSLSSVVTVPSSSLGTQT<br>YICNVNHKPSNTKVDKKVEPKCEF<br>(SEQ ID NO: 110) |

H2L2a

| | |
|---|---|
| QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG | QVQLVESGGTLVQPGGSLRLSCAASGFSFT<br>DAWMSWVRQAPGKELEWVSSISGSGGSTYY<br>AGSVKGRFTISRDNSKNTLYLQMNSLRAED<br>TAVYYCARAAAAAAAAAAAAAAAWGQGTLVT<br>VDDDDKEVQLVQSGGGLVQPGGSLRLSCAG<br>SGFTFSSYVMHWLRQAPGKGLEWVSVIGTG<br>GVTHYADSVKGRFTISRDNAKNSLYLQMNS<br>LRAEDTAVYYCARWGYYGSGSYENDAFDIW<br>GQGTMVTVSSASTKGPSVFPLAPSSKSTSG |

TABLE 9-continued

PROTEASE-REGULATED ANTIBODIES (Type 4)

| Heavy chain | Heavy chain |
|---|---|

GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 111)

GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 112)

H2L4a

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 113)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTICVDKICVEPKCEF
(SEQ ID NO: 114)

H2L5a

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 115)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 116)

H2L7a

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 117)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 118)

H2L8a

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 119)

QVQLVESGGTLVQPGGSLRLSCAASGFSFT
DAWMSWVRQAPGKELEWVSSISGSGGSTYY
AGSVKGRFTISRDNSKNTLYLQMNSLRAED
TAVYYCARAAAAAAAAAAAAAAAAWGQGTLVT
VDDDDKEVQLVQSGGGLVQPGGSLRLSCAG
SGFTFSSYVMHWLRQAPGKGLEWVSVIGTG
GVTHYADSVKGRFTISRDNAKNSLYLQMNS
LRAEDTAVYYCARWGYYGSGSYENDAFDIW
GQGTMVTVSSASTKGPSVFPLAPSSKSTSG
GTAALGCLVKDYFPEPVTVSWNSGALTSGV
HTFPAVLQSSGLYSLSSVVTVPSSSLGTQT
YICNVNHKPSNTKVDKKVEPKCEF
(SEQ ID NO: 120)

Example 3

TF-Binding ELISA

Figure 10:
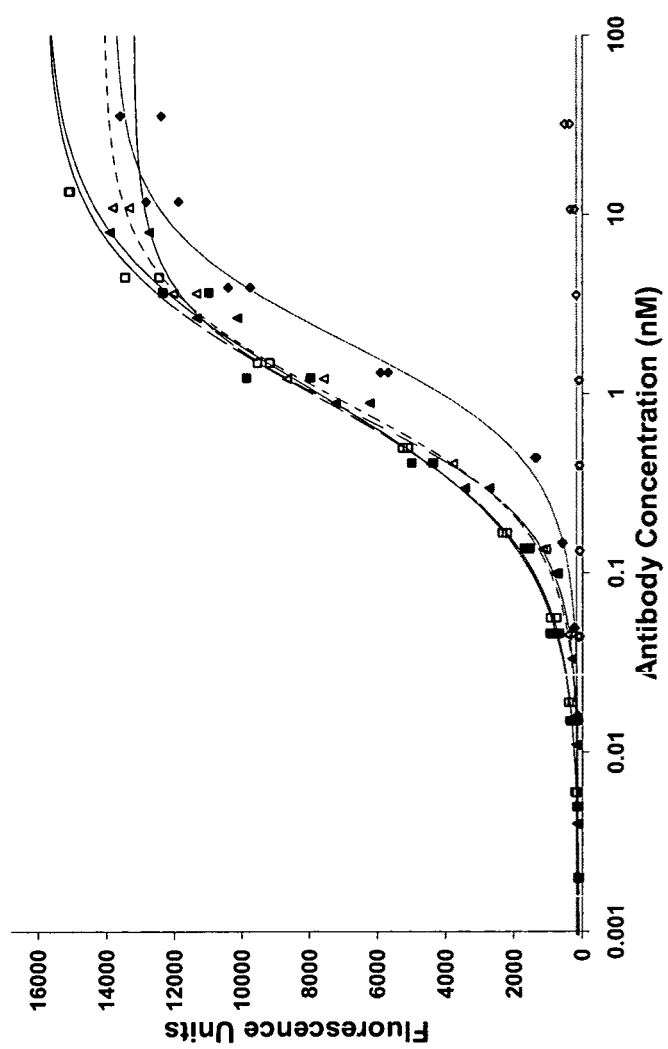
FIG. 10. TF-binding ELISA. Four bispecific antibodies and parental antibodies were analyzed for binding to TF. Antibodies were detected with HRP-conjugated anti-human IgG was used for detection. Curve fitting of the data was performed using a 4-parameter equation with the Solver function in Microsoft Excel. Positive control anti-TF IgG 3E10x: $IC_{50}$=2.0 nM (filled diamond, solid line); Linker 1 (SEQ ID NO: 1) IgG-like bispecific antibody: $IC_{50}$=0.78 nM (filled triangle, large dashed line); Linker 2 (SEQ ID NO: 2) IgG-like bispecific antibody: $IC_{50}$=0.93 nM (open triangle, small dashed line); Linker 3 (SEQ ID NO: 3) IgG-like bispecific antibody: $IC_{50}$=1.06 nM (filled square, alternating small and large dashed line); Linker 4 (SEQ ID NO: 4) IgG-like bispecific antibody: $IC_{50}$=1.01 nM (open square, two large and one small dashed line); and negative control anti-RG1 IgG 19G9: no binding (open diamond, solid line).

Biotinylated TF (1 µg/ml) was added to streptavidin pre-coated 96-well plates (Pierce Chemical, Rockford, Ill.) and incubated for 1 hr. The plates were then washed (5×) with PBS containing 0.5% Tween-20. Samples and controls (serially diluted) were added to the wells and incubated for 1 hr, followed by washes (5×) with PBS containing 0.5% Tween-20. Horseradish peroxidase (HRP)-conjugated anti-human IgG or HRP-conjugated anti-human Fab were diluted in PBS (1:5000) and added to each well. Following a 1 hr incubation, the plates were washed again. Amplex Red (10 µg/ml) was added to each well, and the signal was read using a plate reader. The data was analyzed using Softmax (Molecular Devices, Sunnyvale, Calif.). Results are shown in FIG. 10.

Example 4

RG1-Binding ELISA

Figure 11:
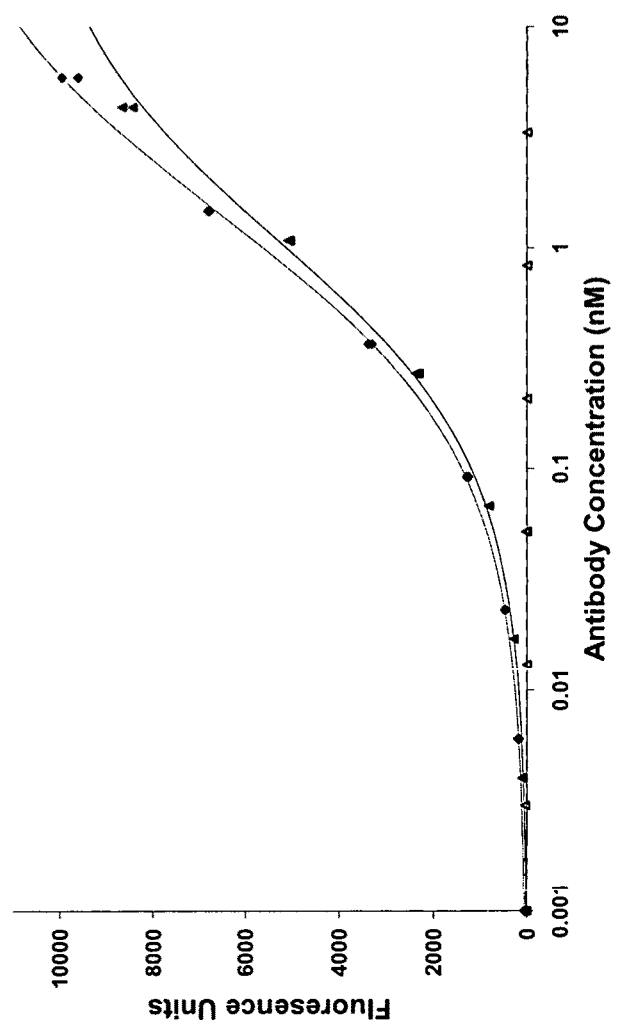
FIG. 11. RG1-binding ELISA. A bispecific antibody containing Linker 1, anti-RG1 antibody 19G9, and polyclonal nonimmune control human IgG kappa were analyzed for binding to RG-1. Curve fitting of the data was performed using a 4-parameter equation with the Solver function in Microsoft Excel. Positive control anti-RG1 IgG 19G9: $IC_{50}$=1.4 nM (filled diamond, solid line); Linker 1 (SEQ ID NO: 1) IgG-like bispecific antibody: $IC_{50}$=1.1 nM (filled triangle, large dashed line); and negative control nonimmune polyclonal human IgG kappa: no binding (open triangle, small dashed line).

Ninety-six well plates were coated with RG1 (1 µg/ml) by overnight incubation, and the plates were then washed (5×) with PBS containing 0.5% Tween-20. Samples and controls (serially diluted) were added to the wells and incubated for 1 hr, followed by washes (5×) with PBS containing 0.5% Tween-20. Horserandish peroxidase (HRP)-conjugated anti-human IgG or HRP-conjugated anti-human Fab were diluted in PBS (1:5000) and added to each well. Following a 1 hr incubation, the plates were washed again. Amplex Red (10 µg/ml) was added to each well, and the signal was read using a plate reader. The data was analyzed using Softmax (Molecular Devices, Sunnyvale, Calif.). Results are shown in FIG. 11.

Example 5

Sandwich Antigen-Binding ELISA

The antigen binding activity of a bispecific protease-regulated antibody (illustrated in FIG. 2) was measured using a sandwich antigen-binding ELISA. This antibody binds two antigens, RG-1 and TF, and the linker contains cleavage sites for enterokinase ("EK").

Figure 12:
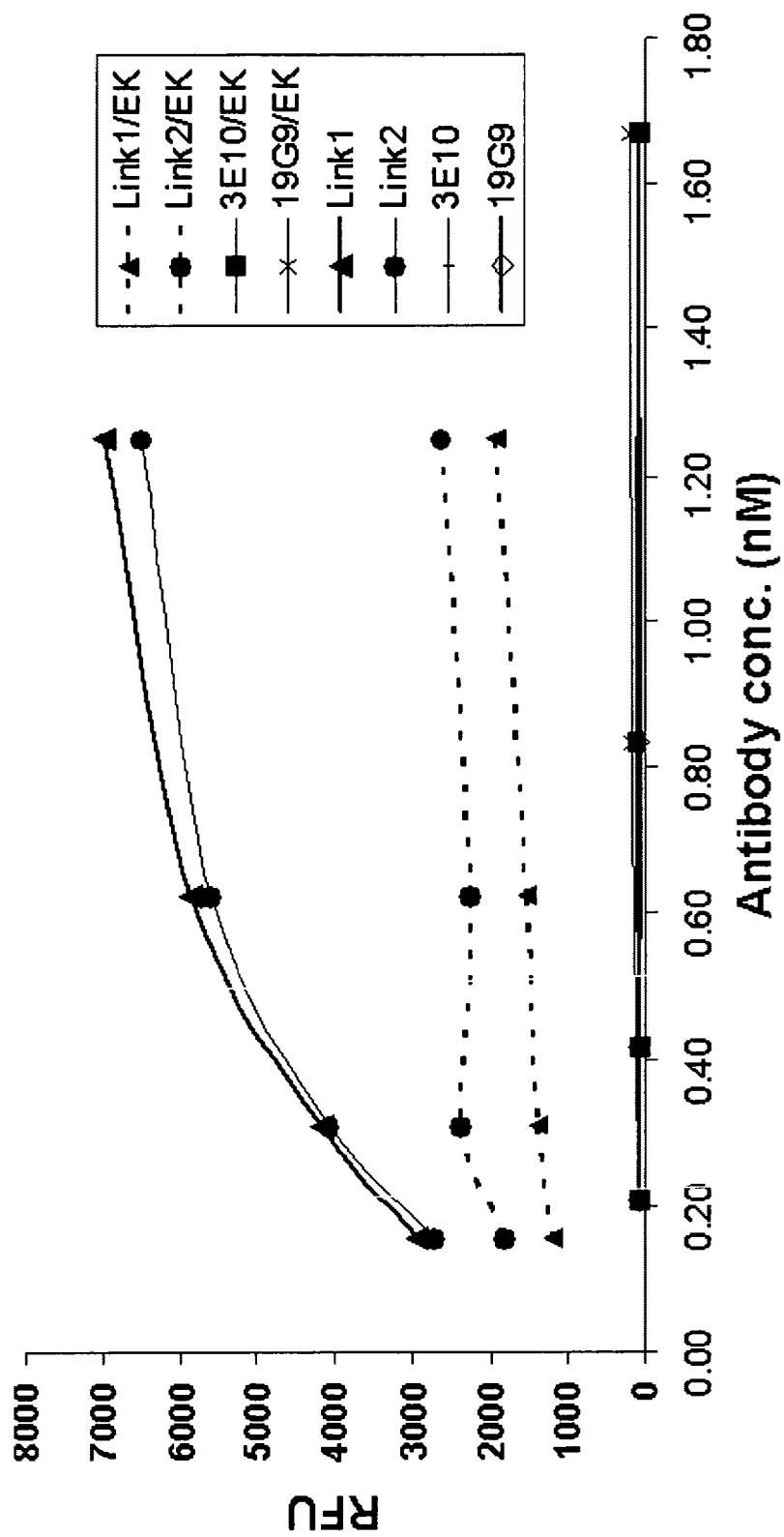
FIG. 12. Measurement of the antigen-binding activity of a bispecific protease-regulated antibody using a sandwich antigen-binding ELISA. The linker of this antibody contained cleavage sites for enterokinase.

Ninety-six well plates were coated with RG1 (1 µg/ml) by overnight incubation. The plates were then washed five times with PBS containing 0.5% Tween-20. Antibody samples and controls were digested with 30 units of enterokinase for 16 hr at 37° C. (see Example 4). The antibody samples, with or without enterokinase digestion, were serially diluted and added to the wells of the ELISA plates. The samples were incubated for one hour, followed by washes (5×) with PBS containing 0.5% Tween-20. Biotinylated TF (0.1 µg/ml) was added to each well and incubated for one hour. Horseradish peroxidase (HRP)-conjugated streptavidin (1:10000 diluted) was then added to each well. Following a one-hour incubation, the plates were washed again. Amplex Red (10 µg/ml) was added to each well, and the signal was read using a plate reader. The data was analyzed using Softmax® (Molecular Devices, Sunnyvale, Calif.). Parental antibodies 3E10, 19G9, and polyclonal human Fab were used as controls. The results are the average of duplicate wells (FIG. 12). The untreated bispecific protease-regulated antibody simultaneously binds to both TF and RG-1 ("Link 1" and "Link2," respectively). However, following enterokinase treatment, the binding to both antigens is greatly reduced ("Link1/EK" and "Link2/EK," respectively).

Figure 13:
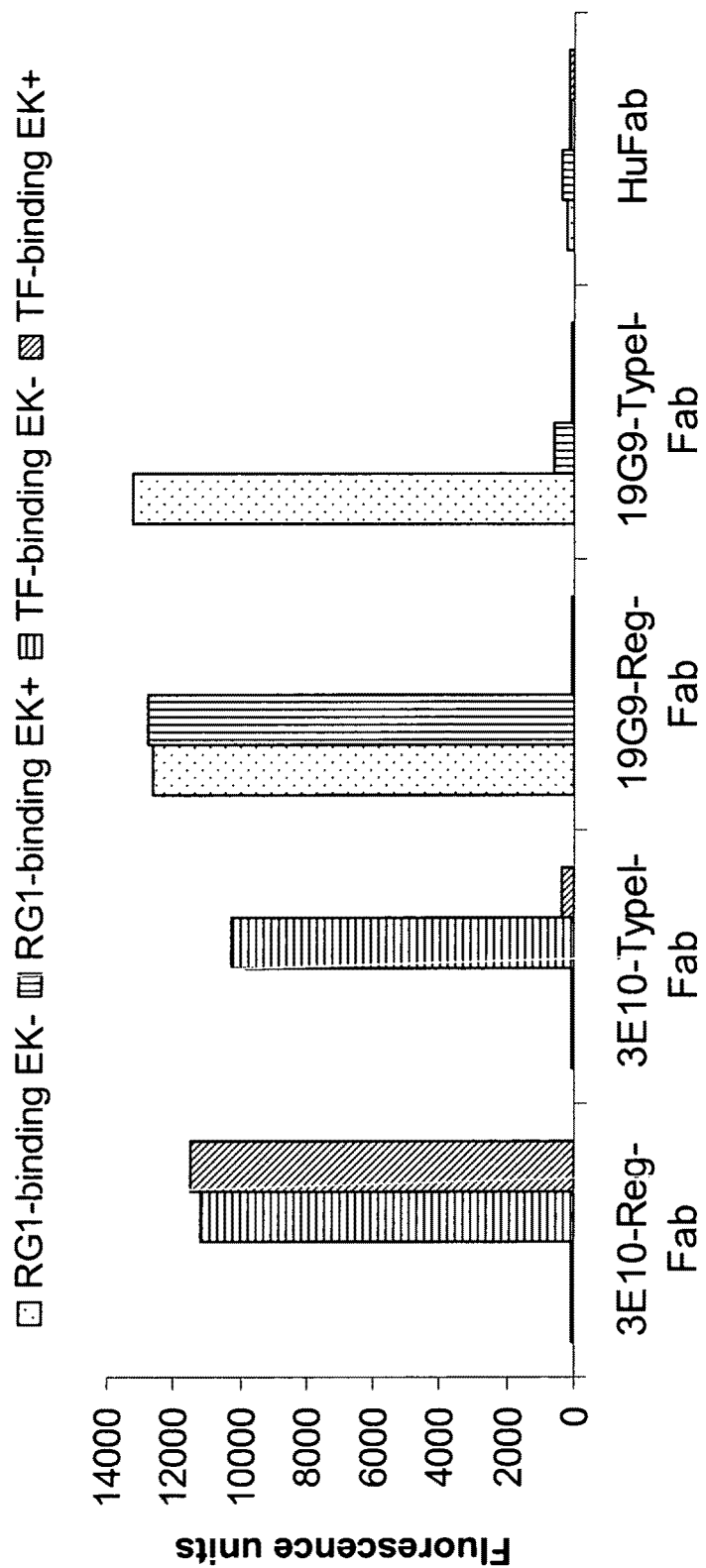
FIG. 13. Measurement of the antigen-binding activity of protease-regulated antibodies 3E10-Type1-Fab and 19G9-Type1-Fab. The controls are designated 3E10-Reg-Fab, 19G9-Reg-Fab, and HuFab.

The antigen binding activity of several examples of protease-regulated antibodies was also measured using this assay. For example, the antigen binding activity of protease-regulated antibodies 3E10-Type1-Fab and 19G9-Type1-Fab is shown in FIG. 13. The controls are designated 3E10-Reg-Fab, 19G9-Reg-Fab, and HuFab.

Figure 14:
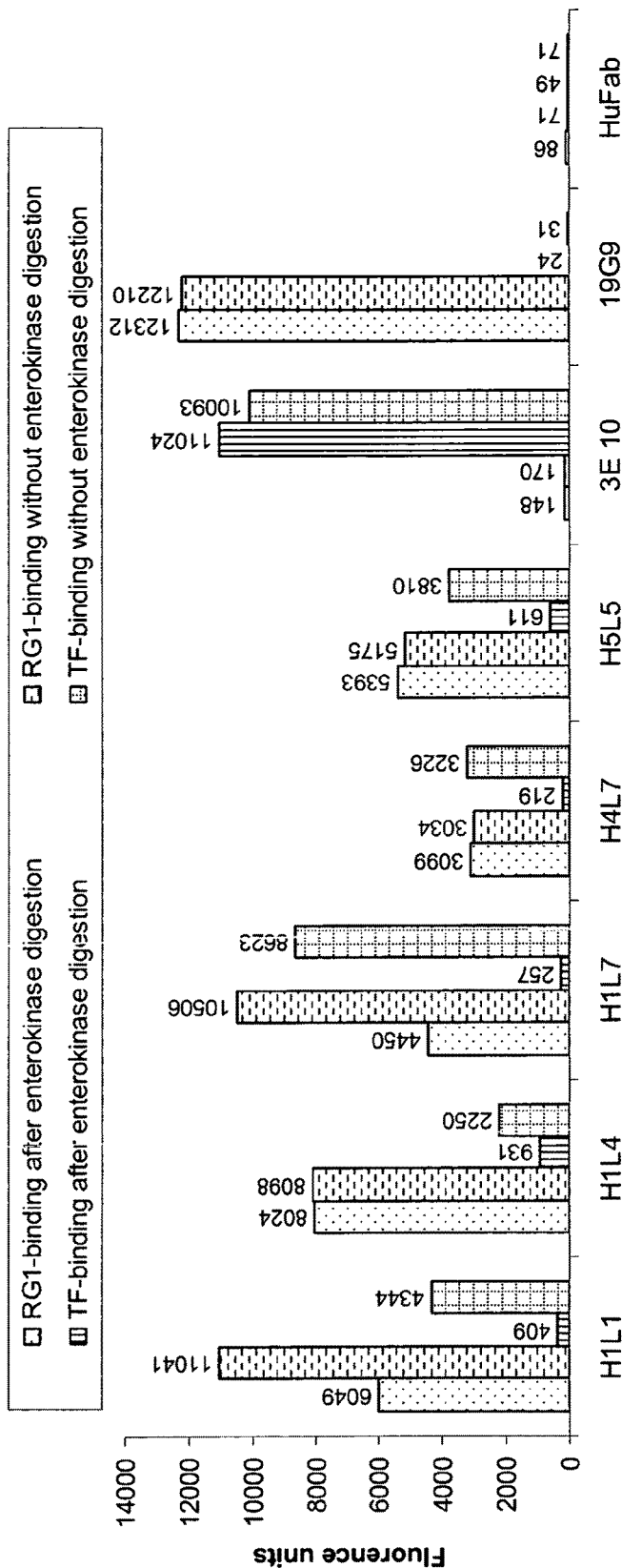
FIG. 14. Measurement of the antigen-binding activity of Fab-like protease-regulated antibodies H1L1, H1L4, H1L7, H4L7, and H5L5 (Type 2) in the absence and presence of enterokinase. Parental antibodies 3E10 and 19G9, and polyclonal human Fab were used as control.
Figure 15:
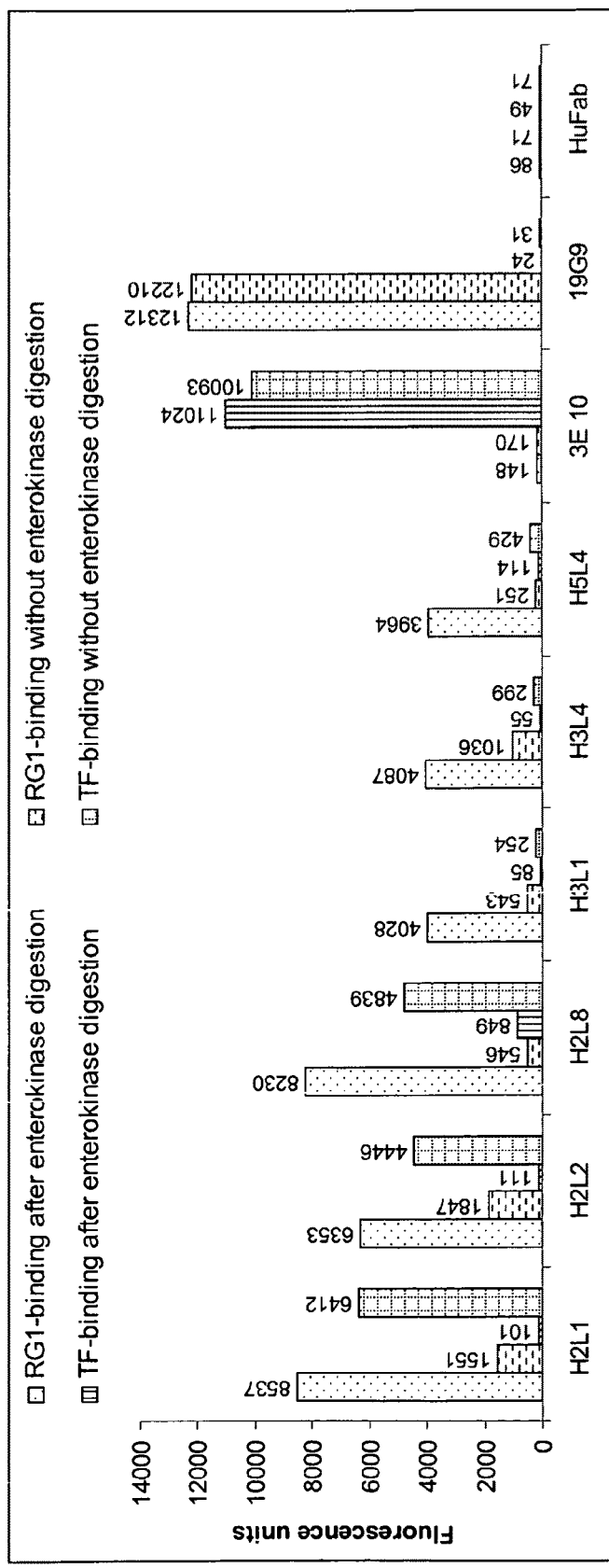
FIG. 15. Measurement of the antigen-binding activity of Fab-like protease-regulated antibodies H2L1, H2L2, and H2L8 (Type 3) and H3L1, H3L4, and H5L4 (Type 4) in the absence and presence of enterokinase. Parental antibodies 3E10 and 19G9, and polyclonal human Fab were used as control.

The antigen binding activity of Fab-like protease-regulated antibodies is demonstrated in FIG. 14. The activity of antibodies H1L1, H1L4, H1L7, H4L7, and H5L5 (Type 2) was measured in the absence and presence of enterokinase. Parental antibodies 3E10, 19G9, and polyclonal human Fab were used as controls. Similarly, FIG. 15 shows the antigen binding activity of Fab-like protease-regulated antibodies H2L1, H2L2, and H2L8 (Type 3) and H3L1, H3L4, and H5L4 (Type 4).

Example 6

Enterokinase Digestion of Protease-Regulated Antibodies

Protease-regulated antibodies were digested with EnterokinaseMax™, the catalytic subunit of enterokinase (Invitrogen, Carlsbad, Calif.). The concentration of antibodies was adjusted to 1-5 µg/ml. A volume of antibody (100 µl) was mixed with 20 µl 10× EnterokinaseMax™ buffer and 75 µl sterile water in a tube. EnterokinaseMax™ (5 µl) was added to each sample and the samples were incubated at 37° C. for 16 hr. For the control group, a volume of water (5 µl) was used.

Example 7

Western Blots of Antibodies

Figure 16:
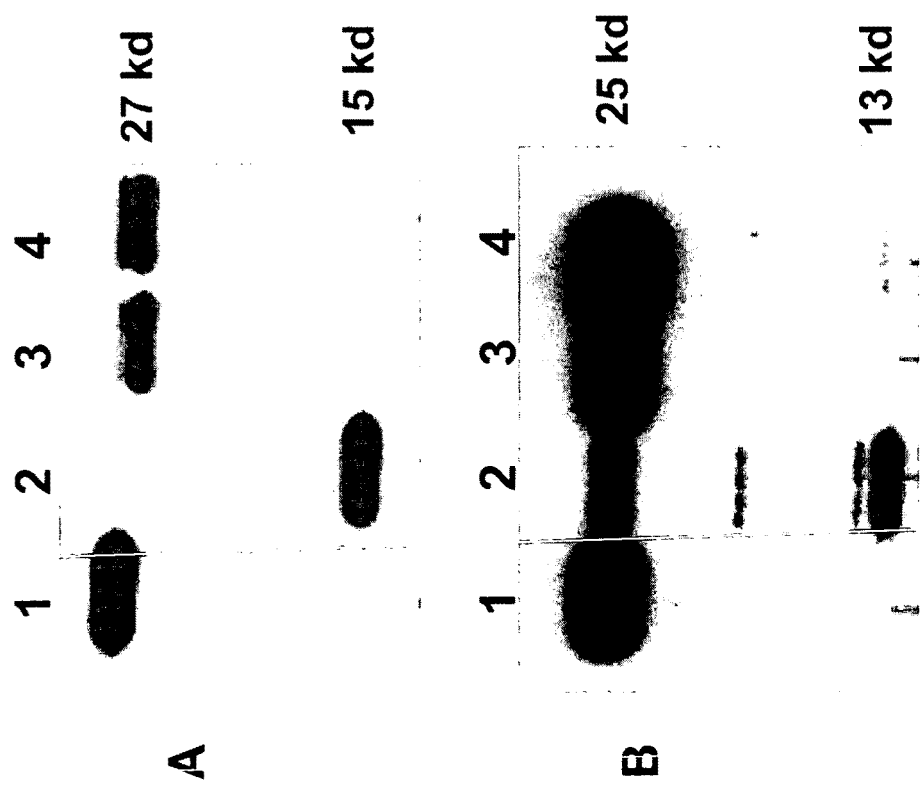
FIG. 16. Western blots of protease-regulated antibody 3E10-Type1-Fab detected with anti-Myc antibody (A) or anti-kappa chain antibody (B). Lane 1 and 2: 3E10-Type1-Fab without or with enterokinase digestion, respectively. Lane 3 and 4: 3E10-Reg-Fab without or with enterokinase digestion, respectively.
Figure 17:
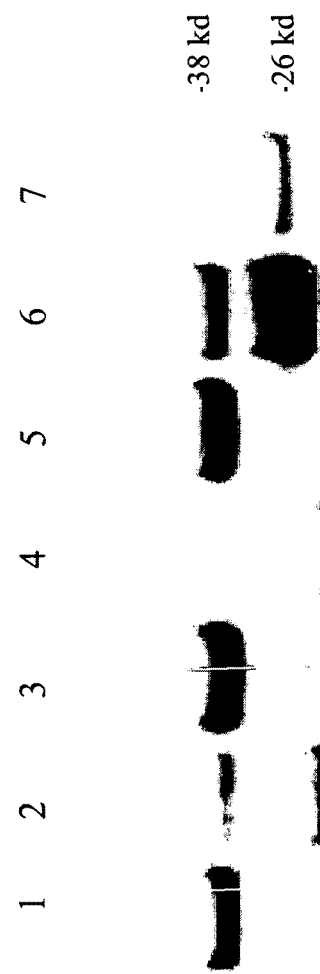
FIG. 17. Western blots of Fab-like protease-regulated antibodies H1L1, H1L7, and H5L5 (Type 2) in the absence and presence of enterokinase. Antibodies were detected with anti-IgG(H+L) antibody. Lane 1 and 2: H1L1 without or with enterokinase digestion, respectively. Lane 3 and 4: H1L7 without or with enterokinase digestion, respectively. Lane 5 and 6: H5L5 without or with enterokinase digestion, respectively. Lane 7: 3E10-Reg-Fab.
Figure 18:
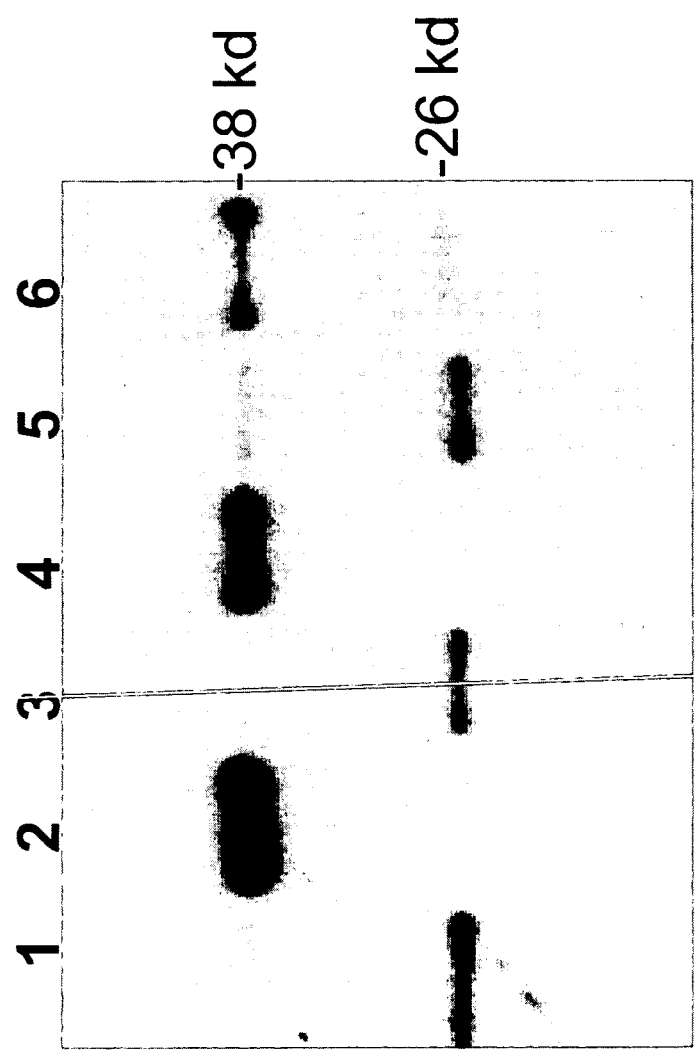
FIG. 18. Western blots of Fab-like protease-regulated antibodies H2L2 and H2L8 (Type 3) and H3L4 (Type 4) in the absence and presence of enterokinase. Antibodies were detected with anti-Myc antibody. Lane 1 and 2: H2L2 without or with enterokinase digestion, respectively. Lane 3 and 4: H2L8 without or with enterokinase digestion, respectively. Lane 5 and 6: H3L4 without or with enterokinase digestion, respectively.

Three detection antibodies were used to probe protease-regulated antibodies: anti-human kappa antibody, anti-human IgG(H+L), and anti-Myc tag antibodies. These detection antibodies were conjugated with horseradish peroxidase (HRP). Approximately 50 ng of antibody samples were mixed with loading buffer containing DTT (Invitrogen, Carlsbad, Calif.) and boiled for 5 min. The samples were then loaded onto a 12% Bis-Tris NuPAGE® gel (Invitrogen, Carlsbad, Calif.), separated, and transferred to nitrocellulose membranes. After blocking with 5% dry milk for 2 hr, the nitrocellulose membrane was incubated with a detection antibody for 1.5 hr. The membrane was then washed in PBS containing 0.5% Tween-20, and incubated with SuperSignal West Femto (Pierce Chemical, Rockford, Ill.), and expose to X-ray film for development. Results are shown in FIGS. 16-18.

Example 8

Subcutaneous Xenograft Cancer Model

Human mammary xenograft, MaTu cells are maintained as adherent cultures in RPMI supplemented with 10% FBS. Ncr nude mice (8-12 weeks of age) are inoculated subcutaneously in the right flank with $5 \times 10^6$ cells in 0.1 mL of 80% matrigel/20% HBSS. When tumors reach an average size of ~180 mg (6 days), treatment is initiated. Antibodies are administered i.v. once every four days (Q4Dx3) at a dose of 10 mg/kg. Control mice are treated with PBS or an unconjugated monoclonal antibody. Daily examinations into the health status of each animal are conducted. Each experimental group consists of 10 mice and the dosing volume was 0.1 mL/10 g body weight. The length and width of each tumor is measured by using an electronic caliper 2-3 times per week and tumor weights (mg) are calculated based on the formula of [length (mm)×width (mm)$^2$]/2. All data, including daily observations, obtained throughout the course of the study are documented. Tumor growth inhibition (TGI) is calculated as 1−T/C×100, where T=final tumor weights from a treated group, and C=final tumor weights from the control group. The data demonstrates the therapeutic utility of antibodies for the treatment of tumors.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

The invention claimed is:

1. An antibody comprising a heavy chain and a light chain, each comprising one or more variable regions, wherein said antibody is capable of binding an antigen or an epitope, and wherein said antibody comprises an amino acid linker which comprises one or more protease cleavage sites, wherein said protease cleavage sites are selected from the group consisting of SEQ ID NOS:26, 27, 28, 29, 30, 31, and 32, wherein the antibody comprises an amino acid sequence selected from the group consisting of SEQ ID NO:33-120.

2. A kit comprising an antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and wherein the light chain comprises the amino acid sequence SEQ ID NO:81.

3. A kit comprising an antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and wherein the heavy chain comprises the amino acid sequence SEQ ID NO:82.

4. A kit comprising an antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and wherein the light chain comprises the amino acid sequence SEQ ID NO:81 and the heavy chain comprises the amino acid sequence SEQ ID NO:82.

5. An antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and wherein the light chain comprises the amino acid sequence SEQ ID NO:81.

6. An antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and, wherein the heavy chain comprises the amino acid sequence SEQ ID NO:82.

7. An antibody which comprises a heavy chain and a light chain, each comprising one or more variable regions, wherein the antibody is capable of binding an antigen or an epitope, and wherein the antibody comprises an amino acid linker which comprises one or more protease cleavage sites, wherein the protease cleavage sites are selected from the group consisting of SEQ ID NOS:26, 27, 28, 29, 30, 31, and 32, wherein the antibody comprises (a) a heavy chain having the structure $NH_2$-$V_H$1-linker-$V_H$2-$C_H$1-CH2-CH3-COOH and (b) a light chain having the structure $NH_2$-$V_L$1-linker-$V_L$2-CL-COOH, and, wherein the light chain comprises the amino acid sequence SEQ ID NO:81 and the heavy chain comprises the amino acid sequence SEQ ID NO:82.

8. The antibody of claim 5 which is conjugated to monomethylauristatin-E (MMAE).

9. The antibody of claim 6 which is conjugated to monomethylauristatin-E (MMAE).

10. The antibody of claim 7 which is conjugated to monomethylauristatin-E (MMAE).

11. A pharmaceutical composition comprising the antibody of claim 5.

12. A pharmaceutical composition comprising the antibody of claim 6.

13. A pharmaceutical composition comprising the antibody of claim 7.

14. The pharmaceutical composition of claim 11, wherein the antibody is conjugated to monomethylauristatin-E (MMAE).

15. The pharmaceutical composition of claim 12, wherein the antibody is conjugated to monomethylauristatin-E (MMAE).

16. The pharmaceutical composition of claim 13, wherein the antibody is conjugated to monomethylauristatin-E (MMAE).

17. A kit comprising:
  an antibody comprising one or more variable regions, wherein each of the one or more variable regions comprises a heavy chain and a light chain and is capable of binding an antigen or an epitope, and wherein the antibody comprises an amino acid linker which comprises one or more protease cleavage sites; and
  solutions for suspending or fixing the cells, detectable labels, solutions for rendering a polypeptide susceptible to the binding of an antibody, solutions for lysing cells, and/or solutions for the purification of polypeptides wherein the antibody comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein the light chain comprises the amino acid sequence SEQ ID NO:81.

18. A kit comprising:
  an antibody comprising one or more variable regions, wherein said antibody binds one or more antigens or epitopes; and
  solutions for suspending or fixing the cells, detectable labels, solutions for rendering a polypeptide susceptible to the binding of an antibody, solutions for lysing cells, and/or solutions for the purification of polypeptides wherein the antibody comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein the heavy chain comprises the amino acid sequence SEQ ID NO:82.

19. The kit of claim 18, wherein the light chain comprises the amino acid sequence SEQ ID NO:81.

20. An antibody comprising one or more variable regions, wherein said antibody binds one or more antigens or epitopes, wherein said variable region comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein said antibody comprises a variable region light chain comprising the amino acid sequence SEQ ID NO:81.

21. An antibody comprising one or more variable regions, wherein said antibody binds one or more antigens or epitopes, wherein said variable region comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein said antibody comprises a variable region heavy chain comprising the amino acid sequence SEQ ID NO:82.

22. The antibody of claim 21, wherein said antibody comprises a variable region light chain comprising the amino acid sequence SEQ ID NO:81.

23. The antibody of claim 20, which is conjugated to monomethylauristatin-E (MMAE).

24. The antibody of claim 21, which is conjugated to monomethylauristatin-E (MMAE).

25. The antibody of claim 22, which is conjugated to monomethylauristatin-E (MMAE).

26. A pharmaceutical composition, comprising an antibody in combination with a pharmaceutically acceptable carrier, wherein the antibody comprises one or more variable regions, wherein said antibody binds one or more antigens or epitopes, wherein said variable region comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein said antibody comprises a variable region light chain comprising the amino acid sequence SEQ ID NO:81.

27. A pharmaceutical composition, comprising an antibody in combination with a pharmaceutically acceptable carrier, wherein the antibody comprises one or more variable regions, wherein said antibody binds one or more antigens or epitopes, wherein said variable region comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH, and wherein said antibody comprises a variable region heavy chain comprising the amino acid sequence SEQ ID NO:82.

28. The pharmaceutical composition of claim 27, wherein the antibody comprises a variable region light chain comprising the amino acid sequence SEQ ID NO:81.

29. The pharmaceutical composition of claim 26, wherein the antibody is conjugated to monomethylauristatin-E (MMAE).

30. The pharmaceutical composition of claim 27, wherein the antibody is conjugated to monomethylauristatin-E (MMAE).

31. The pharmaceutical composition of claim 28, wherein the antibody is conjugated to monomethylauristatin-E (MMAE).

32. The antibody of claim 1, wherein said antibody is conjugated to a therapeutic or cytotoxic agent.

33. The antibody of claim 32, wherein said antibody is conjugated to an agent selected from the group consisting of monomethylauristatin-E (MMAE), aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-I1), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribomiclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin, and functional analogs thereof.

34. A pharmaceutical composition comprising a therapeutically effective amount of an antibody of claim 1 in combination with a pharmaceutically acceptable carrier.

35. The pharmaceutical composition of claim 34 further comprising one or more pharmaceutical agents.

36. A kit comprising an antibody of claim 1.

37. The kit of claim 36, further comprising solutions for suspending or fixing the cells, detectable labels, solutions for rendering a polypeptide susceptible to the binding of an antibody, solutions for lysing cells, and/or solutions for the purification of polypeptides.

38. The kit of claim 37 wherein the antibody comprises a heavy chain having the structure $NH_2$-$V_H$1-linker-$V_H$2-$C_H$1-CH2-CH3-COOH; and a light chain having the structure $NH_2$-$V_L$1-linker-$V_L$2-CL-COOH.

* * * * *

SEQUENCE LISTING

```
<160> NUMBER OF SEQ ID NOS: 120

<210> SEQ ID NO 1
<211> LENGTH: 6
<212> TYPE: PRT
<213> ORGANISM: Artificial Sequence
<220> FEATURE:
<223> OTHER INFORMATION: Linker 1

<400> SEQUENCE: 1

Ser Asp Asp Asp Asp Lys
1               5

<210> SEQ ID NO 2
<211> LENGTH: 10
<212> TYPE: PRT
<213> ORGANISM: Artificial Sequence
<220> FEATURE:
<223> OTHER INFORMATION: Linker 2

<400> SEQUENCE: 2

Gly Gly Gly Gly Ser Asp Asp Asp Asp Lys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Linker 3

<400> SEQUENCE: 3

Gly Gly Gly Gly Ser Asp Asp Asp Asp Lys Gly Gly Gly Gly Ser
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Linker 4

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 20
<212> TYPE: PRT
<213> ORGANISM: Artificial Sequence
<220> FEATURE:
<223> OTHER INFORMATION: Linker 5

<400> SEQUENCE: 5

Ile His Pro Val Leu Ser Gly Leu Ser Arg Ile Val Asn Gly Glu Asp
1               5                   10                  15
```

Ala Val Pro Gly
           20

<210> SEQ ID NO 6
<211> LENGTH: 20
<212> TYPE: PRT
<213> ORGANISM: Artificial Sequence
<220> FEATURE:
<223> OTHER INFORMATION: Linker 6

<400> SEQUENCE: 6

Val Ala Ala Pro Phe Asp Asp Asp Lys Ile Val Gly Gly Tyr Ile
1               5                   10                  15

Cys Glu Glu Asn
           20

<210> SEQ ID NO 7
<211> LENGTH: 20
<212> TYPE: PRT
<213> ORGANISM: Artificial Sequence
<220> FEATURE:
<223> OTHER INFORMATION: Linker 7

<400> SEQUENCE: 7

Glu Leu Leu Glu Ser Tyr Ile Asp Gly Arg Ile Val Glu Gly Ser Asp
1               5                   10                  15

Ala Glu Ile Gly
           20

<210> SEQ ID NO 8
<211> LENGTH: 20
<212> TYPE: PRT
<213> ORGANISM: Artificial Sequence
<220> FEATURE:
<223> OTHER INFORMATION: Linker 8

<400> SEQUENCE: 8

Ser Thr Gln Ser Phe Asn Asp Phe Thr Arg Val Val Gly Gly Glu Asp
1               5                   10                  15

Ala Lys Pro Gly
           20

<210> SEQ ID NO 9
<211> LENGTH: 20
<212> TYPE: PRT
<213> ORGANISM: Artificial Sequence
<220> FEATURE:
<223> OTHER INFORMATION: Linker 9

<400> SEQUENCE: 9

Pro Glu Arg Gly Asp Asn Asn Leu Thr Arg Ile Val Gly Gly Gln Glu
1               5                   10                  15

Cys Lys Asp Gly
           20

<210> SEQ ID NO 10
<211> LENGTH: 20
<212> TYPE: PRT
<213> ORGANISM: Artificial Sequence
<220> FEATURE:
<223> OTHER INFORMATION: Linker 10

<400> SEQUENCE: 10

Glu Asp Gln Glu Asp Gln Val Asp Pro Arg Leu Ile Asp Gly Lys Met

```
1               5                   10                  15
Thr Arg Arg Gly
            20

<210> SEQ ID NO 11
<211> LENGTH: 20
<212> TYPE: PRT
<213> ORGANISM: Artificial Sequence
<220> FEATURE:
<223> OTHER INFORMATION: Linker 11

<400> SEQUENCE: 11

Lys Arg Asn Ala Ser Lys Pro Gln Gly Arg Ile Val Gly Gly Lys Val
1               5                   10                  15

Cys Pro Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Linker 12

<400> SEQUENCE: 12

Ser Val Cys Thr Thr Lys Thr Ser Thr Arg Ile Val Gly Gly Thr Asn
1               5                   10                  15

Ser Ser Trp Gly
            20

<210> SEQ ID NO 13
<211> LENGTH: 5
<212> TYPE: PRT
<213> ORGANISM: Artificial Sequence
<220> FEATURE:
<223> OTHER INFORMATION: Linker 13

<400> SEQUENCE: 13

Ser Arg Ile Val Gly
1               5

<210> SEQ ID NO 14
<211> LENGTH: 20
<212> TYPE: PRT
<213> ORGANISM: Artificial Sequence
<220> FEATURE:
<223> OTHER INFORMATION: Linker 14

<400> SEQUENCE: 14

Gly Ser Leu Val Ser Gly Ser Cys Ser Gln Ile Ile Asn Gly Glu Asp
1               5                   10                  15

Cys Ser Pro His
            20

<210> SEQ ID NO 15
<211> LENGTH: 5
<212> TYPE: PRT
<213> ORGANISM: Artificial Sequence
<220> FEATURE:
<223> OTHER INFORMATION: Linker 15

<400> SEQUENCE: 15

Ser Arg Ile Ile Asn
1               5
```

<210> SEQ ID NO 16
<211> LENGTH: 5
<212> TYPE: PRT
<213> ORGANISM: Artificial Sequence
<220> FEATURE:
<223> OTHER INFORMATION: Linker 16

<400> SEQUENCE: 16

Asn Lys Leu Val His
1               5

<210> SEQ ID NO 17
<211> LENGTH: 5
<212> TYPE: PRT
<213> ORGANISM: Artificial Sequence
<220> FEATURE:
<223> OTHER INFORMATION: Linker 17

<400> SEQUENCE: 17

Asp Lys Ile Ile Asp
1               5

<210> SEQ ID NO 18
<211> LENGTH: 5
<212> TYPE: PRT
<213> ORGANISM: Artificial Sequence
<220> FEATURE:
<223> OTHER INFORMATION: Linker 18

<400> SEQUENCE: 18

Phe Asn Val Leu Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Linker 19

<400> SEQUENCE: 19

Thr Arg Ala Ile Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Linker 20

<400> SEQUENCE: 20

Thr Arg Leu Asp Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Linker 21

<400> SEQUENCE: 21

Thr Arg Ile Ile Lys
1               5

```
<210> SEQ ID NO 22
<211> LENGTH: 5
<212> TYPE: PRT
<213> ORGANISM: Artificial Sequence
<220> FEATURE:
<223> OTHER INFORMATION: Linker 22

<400> SEQUENCE: 22

Ser Gly Ser Asn Gln
1               5

<210> SEQ ID NO 23
<211> LENGTH: 5
<212> TYPE: PRT
<213> ORGANISM: Artificial Sequence
<220> FEATURE:
<223> OTHER INFORMATION: Linker 23

<400> SEQUENCE: 23

Ser Lys Val Leu Asn
1               5

<210> SEQ ID NO 24
<211> LENGTH: 5
<212> TYPE: PRT
<213> ORGANISM: Artificial Sequence
<220> FEATURE:
<223> OTHER INFORMATION: Linker 24

<400> SEQUENCE: 24

Asn Lys Ile Ile Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Linker 25

<400> SEQUENCE: 25

Asp Lys Leu Leu Glu
1               5

<210> SEQ ID NO 26
<211> LENGTH: 5
<212> TYPE: PRT
<213> ORGANISM: Artificial Sequence
<220> FEATURE:
<223> OTHER INFORMATION: Linker cleavage site

<400> SEQUENCE: 26

Asp Asp Asp Asp Lys
1               5

<210> SEQ ID NO 27
<211> LENGTH: 5
<212> TYPE: PRT
<213> ORGANISM: Artificial Sequence
<220> FEATURE:
<223> OTHER INFORMATION: Linker cleavage site

<400> SEQUENCE: 27

Ile Glu Asp Gly Arg
1               5

<210> SEQ ID NO 28
```

```
<211> LENGTH: 6
<212> TYPE: PRT
<213> ORGANISM: Artificial Sequence
<220> FEATURE:
<223> OTHER INFORMATION: Linker cleavage site

<400> SEQUENCE: 28

Leu Val Pro Arg Gly Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Linker cleavage site

<400> SEQUENCE: 29

Glu Asn Leu Tyr Phe Gln Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Linkage cleavage site

<400> SEQUENCE: 30

Leu Glu Val Leu Phe Gln Gly Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Linker cleavage site

<400> SEQUENCE: 31

Ser Ser Val Phe Ala Gln Ser Ile Pro
1               5

<210> SEQ ID NO 32
<211> LENGTH: 8
<212> TYPE: PRT
<213> ORGANISM: Artificial Sequence
<220> FEATURE:
<223> OTHER INFORMATION: Linker cleavage site

<400> SEQUENCE: 32

Lys Gln Leu Arg Val Val Asn Gly
1               5

<210> SEQ ID NO 33
<211> LENGTH: 230
<212> TYPE: PRT
<213> ORGANISM: Artificial Sequence
<220> FEATURE:
<223> OTHER INFORMATION: 3E10 Fab-like Light chain

<400> SEQUENCE: 33

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30
```

Tyr Val Gln Trp Tyr Gln Gln Arg Pro Gly Ser Ser Pro Thr Thr Val
                35                  40                  45

Ile Tyr Glu Asp Asn His Arg Pro Ser Gly Val Pro Asp Arg Phe Ser
 50                  55                  60

Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asn Asn Leu Val Val Phe Gly Gly Gly Thr Lys Leu Thr Val Leu Gly
                100                 105                 110

Ala Gly Gly Gly Ser Asp Asp Asp Lys Arg Thr Val Ala Ala
                115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
                195                 200                 205

Ala Cys Glu Val Thr His Gln Gly Leu Ser Ser Pro Val Thr Lys Ser
                210                 215                 220

Phe Asn Arg Gly Glu Cys
225                 230

<210> SEQ ID NO 34
<211> LENGTH: 233
<212> TYPE: PRT
<213> ORGANISM: Artificial Sequence
<220> FEATURE:
<223> OTHER INFORMATION: 3E10 Fab-like Heavy chain

<400> SEQUENCE: 34

Asp Leu Val Glu Ser Gly Gly Thr Leu Val Gln Pro Gly Gly Ser Leu
 1               5                  10                  15

Arg Leu Ser Cys Ala Ala Ser Gly Phe Ser Phe Thr Asp Ala Trp Met
                 20                  25                  30

Ser Trp Val Arg Gln Ala Pro Gly Lys Glu Leu Glu Trp Val Ser Ser
                 35                  40                  45

Ile Ser Gly Ser Gly Gly Ser Thr Tyr Tyr Ala Gly Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Leu Ser Leu Thr Asp Tyr Tyr Trp Tyr Gly Met Asp Val Trp Gly
                100                 105                 110

Gln Gly Thr Leu Val Thr Val Ser Ala Ser Asp Asp Asp Lys Ser
                115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

```
Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Cys Glu Phe
225                 230
```

<210> SEQ ID NO 35
<211> LENGTH: 219
<212> TYPE: PRT
<213> ORGANISM: Artificial Sequence
<220> FEATURE:
<223> OTHER INFORMATION: 19G9 Fab-like Light chain

<400> SEQUENCE: 35

```
Asp Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Leu
                85                  90                  95

Thr Phe Gly Gly Gly Thr Lys Val Glu Ile Lys Asp Asp Asp Asp Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 36
<211> LENGTH: 231
<212> TYPE: PRT
<213> ORGANISM: Artificial Sequence
<220> FEATURE:
<223> OTHER INFORMATION: 19G9 Fab-like Heavy chain

<400> SEQUENCE: 36

```
Gln Leu Val Gln Ser Gly Gly Gly Leu Val Gln Pro Gly Gly Ser Leu
1               5                   10                  15
```

```
Arg Leu Ser Cys Ala Gly Ser Gly Phe Thr Phe Ser Ser Tyr Val Met
            20                  25                  30

His Trp Leu Arg Gln Ala Pro Gly Lys Gly Leu Glu Trp Val Ser Val
        35                  40                  45

Ile Gly Thr Gly Gly Val Thr His Tyr Ala Asp Ser Val Lys Gly Arg
 50                  55                  60

Phe Thr Ile Ser Arg Asp Asn Ala Lys Asn Ser Leu Tyr Leu Gln Met
 65                  70                  75                  80

Asn Ser Leu Arg Ala Glu Asp Thr Ala Val Tyr Tyr Cys Ala Arg Trp
                85                  90                  95

Gly Tyr Tyr Gly Ser Gly Ser Tyr Glu Asn Asp Ala Phe Asp Ile Trp
            100                 105                 110

Gly Gln Gly Thr Met Val Thr Val Asp Asp Asp Lys Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Cys Glu Phe
225                 230

<210> SEQ ID NO 37
<211> LENGTH: 223
<212> TYPE: PRT
<213> ORGANISM: Artificial Sequence
<220> FEATURE:
<223> OTHER INFORMATION: 3E10 IgG-like Light chain

<400> SEQUENCE: 37

Asn Phe Met Leu Thr Gln Pro His Ser Val Ser Ala Ser Pro Gly Lys
 1               5                  10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
 50                  55                  60

Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Gln Ser Asp Asp Asp Lys Pro Lys Ala Ala Pro Ser Val Thr Leu
        115                 120                 125

Phe Pro Pro Ser Ser Glu Glu Leu Gln Ala Asn Lys Ala Thr Leu Val
    130                 135                 140
```

Cys Leu Ile Ser Asp Phe Tyr Pro Gly Ala Val Thr Val Ala Trp Lys
145                 150                 155                 160

Ala Asp Ser Ser Pro Val Lys Ala Gly Val Glu Thr Thr Thr Pro Ser
            165                 170                 175

Lys Gln Ser Asn Asn Lys Tyr Ala Ala Ser Ser Tyr Leu Ser Leu Thr
        180                 185                 190

Pro Glu Gln Trp Lys Ser His Arg Ser Tyr Ser Cys Gln Val Thr His
    195                 200                 205

Glu Gly Ser Thr Val Glu Lys Thr Val Ala Pro Thr Glu Cys Ser
210                 215                 220

<210> SEQ ID NO 38
<211> LENGTH: 457
<212> TYPE: PRT
<213> ORGANISM: Artificial Sequence
<220> FEATURE:
<223> OTHER INFORMATION: 3E10 IgG-like Heavy chain

<400> SEQUENCE: 38

Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp
        115                 120                 125

Lys Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 39
<211> LENGTH: 220
<212> TYPE: PRT
<213> ORGANISM: Artificial Sequence
<220> FEATURE:
<223> OTHER INFORMATION: 19G9 IgG-like Light chain

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Leu
                85                  90                  95

Thr Phe Gly Gly Gly Thr Lys Val Glu Ile Lys Arg Thr Ser Asp Asp
            100                 105                 110

Asp Asp Lys Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 40
<211> LENGTH: 460
<212> TYPE: PRT
<213> ORGANISM: Artificial Sequence
<220> FEATURE:
<223> OTHER INFORMATION: 19G9 IgG-like Heavy chain

<400> SEQUENCE: 40

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Val Met His Trp Leu Arg Gln Ala Pro Gly Lys Gly Leu Glu Trp Val
        35                  40                  45

Ser Val Ile Gly Thr Gly Gly Val Thr His Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Tyr Tyr Gly Ser Gly Ser Tyr Glu Asn Asp Ala Phe Asp
            100                 105                 110

Ile Trp Gly Gln Gly Thr Met Val Thr Val Ser Ser Ala Ser Asp Asp
        115                 120                 125

Asp Asp Asp Lys Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335
```

Ser Asn Lys Ala Leu Pro Ala Pro Ile Glu Lys Thr Ile Ser Lys Ala
              340                 345                 350

Lys Gly Gln Pro Arg Glu Pro Gln Val Tyr Thr Leu Pro Pro Ser Arg
          355                 360                 365

Glu Glu Met Thr Lys Asn Gln Val Ser Leu Thr Cys Leu Val Lys Gly
      370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 41
<211> LENGTH: 333
<212> TYPE: PRT
<213> ORGANISM: Artificial Sequence
<220> FEATURE:
<223> OTHER INFORMATION: H1L1 Light chain

<400> SEQUENCE: 41

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Glu Ile Val Leu Thr Gln Ser Pro Gly
            115                 120                 125

Thr Leu Ser Leu Ser Pro Gly Glu Arg Ala Thr Leu Ser Cys Arg Ala
    130                 135                 140

Ser Gln Ser Val Ser Ser Ser Tyr Leu Ala Trp Tyr Gln Gln Lys Pro
145                 150                 155                 160

Gly Gln Ala Pro Arg Leu Leu Ile Tyr Gly Ala Ser Ser Arg Ala Thr
                165                 170                 175

Gly Ile Pro Asp Arg Phe Ser Gly Ser Gly Ser Gly Thr Asp Phe Thr
            180                 185                 190

Leu Thr Ile Ser Arg Leu Glu Pro Glu Asp Phe Ala Val Tyr Tyr Cys
        195                 200                 205

Gln Gln Tyr Ser Ser Ser Leu Thr Phe Gly Gly Gly Thr Lys Val Glu
    210                 215                 220

Ile Lys Arg Thr Val Ala Ala Pro Ser Val Phe Ile Phe Pro Pro Ser
225                 230                 235                 240

```
Asp Glu Gln Leu Lys Ser Gly Thr Ala Ser Val Val Cys Leu Leu Asn
            245                 250                 255

Asn Phe Tyr Pro Arg Glu Ala Lys Val Gln Trp Lys Val Asp Asn Ala
        260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
            325                 330

<210> SEQ ID NO 42
<211> LENGTH: 357
<212> TYPE: PRT
<213> ORGANISM: Artificial Sequence
<220> FEATURE:
<223> OTHER INFORMATION: H1L1 Heavy chain

<400> SEQUENCE: 42

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Leu Ser Leu Thr Asp Tyr Tyr Trp Tyr Gly Met Asp Val
        100                 105                 110

Trp Gly Gln Gly Thr Leu Val Thr Val Ser Ala Ser Asp Asp Asp Asp
    115                 120                 125

Lys Glu Val Gln Leu Val Gln Ser Gly Gly Gly Leu Val Gln Pro Gly
    130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
            165                 170                 175

Val Ser Val Ile Gly Thr Gly Val Thr His Tyr Ala Asp Ser Val
        180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
            245                 250                 255

Lys Gly Pro Ser Val Phe Pro Leu Ala Pro Ser Ser Lys Ser Thr Ser
        260                 265                 270
```

```
Gly Gly Thr Ala Ala Leu Gly Cys Leu Val Lys Asp Tyr Phe Pro Glu
            275                 280                 285

Pro Val Thr Val Ser Trp Asn Ser Gly Ala Leu Thr Ser Gly Val His
        290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Cys Glu Phe
            355

<210> SEQ ID NO 43
<211> LENGTH: 330
<212> TYPE: PRT
<213> ORGANISM: Artificial Sequence
<220> FEATURE:
<223> OTHER INFORMATION: H1L4 Light chain

<400> SEQUENCE: 43

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
            85                  90                  95

Asn Asn Leu Val Val Phe Gly Gly Gly Thr Lys Leu Thr Val Leu Gly
        100                 105                 110

Ala Ser Asp Asp Asp Lys Leu Thr Gln Ser Pro Gly Thr Leu Ser
            115                 120                 125

Leu Ser Pro Gly Glu Arg Ala Thr Leu Ser Cys Arg Ala Ser Gln Ser
        130                 135                 140

Val Ser Ser Ser Tyr Leu Ala Trp Tyr Gln Gln Lys Pro Gly Gln Ala
145                 150                 155                 160

Pro Arg Leu Leu Ile Tyr Gly Ala Ser Ser Arg Ala Thr Gly Ile Pro
            165                 170                 175

Asp Arg Phe Ser Gly Ser Gly Ser Gly Thr Asp Phe Thr Leu Thr Ile
        180                 185                 190

Ser Arg Leu Glu Pro Glu Asp Phe Ala Val Tyr Tyr Cys Gln Gln Tyr
    195                 200                 205

Ser Ser Ser Leu Thr Phe Gly Gly Gly Thr Lys Val Glu Ile Lys Arg
210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
            245                 250                 255

Pro Arg Glu Ala Lys Val Gln Trp Lys Val Asp Asn Ala Leu Gln Ser
        260                 265                 270
```

Gly Asn Ser Gln Glu Ser Val Thr Glu Gln Asp Ser Lys Asp Ser Thr
            275                 280                 285

Tyr Ser Leu Ser Ser Thr Leu Thr Leu Ser Lys Ala Asp Tyr Glu Lys
    290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 44
<211> LENGTH: 357
<212> TYPE: PRT
<213> ORGANISM: Artificial Sequence
<220> FEATURE:
<223> OTHER INFORMATION: H1L4 Heavy chain

<400> SEQUENCE: 44

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Glu Val Gln Leu Val Gln Ser Gly Gly Gly Leu Val Gln Pro Gly
    130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
                165                 170                 175

Val Ser Val Ile Gly Thr Gly Gly Val Thr His Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Cys Glu Phe
        355

<210> SEQ ID NO 45
<211> LENGTH: 327
<212> TYPE: PRT
<213> ORGANISM: Artificial Sequence
<220> FEATURE:
<223> OTHER INFORMATION: H1L7 Light chain

<400> SEQUENCE: 45

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
50              55                  60

Gly Ser Ile Asp Thr Ser Ser Asn Ser Ala Ser Leu Thr Ile Ser Gly
65              70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Ser Pro Gly Thr Leu Ser Leu Ser Pro
        115                 120                 125

Gly Glu Arg Ala Thr Leu Ser Cys Arg Ala Ser Gln Ser Val Ser Ser
130                 135                 140

Ser Tyr Leu Ala Trp Tyr Gln Gln Lys Pro Gly Gln Ala Pro Arg Leu
145                 150                 155                 160

Leu Ile Tyr Gly Ala Ser Ser Arg Ala Thr Gly Ile Pro Asp Arg Phe
                165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys Gln Gln Tyr Ser Ser Ser
        195                 200                 205

Leu Thr Phe Gly Gly Gly Thr Lys Val Glu Ile Lys Arg Thr Val Ala
210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
            260                 265                 270

Gln Glu Ser Val Thr Glu Gln Asp Ser Lys Asp Ser Thr Tyr Ser Leu
        275                 280                 285

Ser Ser Thr Leu Thr Leu Ser Lys Ala Asp Tyr Glu Lys His Lys Val
290                 295                 300

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 46
<211> LENGTH: 357
<212> TYPE: PRT
<213> ORGANISM: Artificial Sequence
<220> FEATURE:
<223> OTHER INFORMATION: H1L7 Heavy chain

<400> SEQUENCE: 46

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Glu Val Gln Leu Val Gln Ser Gly Gly Gly Leu Val Gln Pro Gly
    130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
                165                 170                 175

Val Ser Val Ile Gly Thr Gly Gly Val Thr His Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

```
Asn Val Asn His Lys Pro Ser Asn Thr Lys Val Asp Lys Lys Val Glu
            340                 345                 350

Pro Lys Cys Glu Phe
        355

<210> SEQ ID NO 47
<211> LENGTH: 331
<212> TYPE: PRT
<213> ORGANISM: Artificial Sequence
<220> FEATURE:
<223> OTHER INFORMATION: H4L2 Light chain

<400> SEQUENCE: 47

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Asp Asp Asp Asp Lys Glu Ile Val Leu Thr Gln Ser Pro Gly Thr Leu
        115                 120                 125

Ser Leu Ser Pro Gly Glu Arg Ala Thr Leu Ser Cys Arg Ala Ser Gln
130                 135                 140

Ser Val Ser Ser Ser Tyr Leu Ala Trp Tyr Gln Gln Lys Pro Gly Gln
145                 150                 155                 160

Ala Pro Arg Leu Leu Ile Tyr Gly Ala Ser Ser Arg Ala Thr Gly Ile
                165                 170                 175

Pro Asp Arg Phe Ser Gly Ser Gly Ser Gly Thr Asp Phe Thr Leu Thr
            180                 185                 190

Ile Ser Arg Leu Glu Pro Glu Asp Phe Ala Val Tyr Tyr Cys Gln Gln
        195                 200                 205

Tyr Ser Ser Ser Leu Thr Phe Gly Gly Gly Thr Lys Val Glu Ile Lys
210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 48
<211> LENGTH: 349
<212> TYPE: PRT
<213> ORGANISM: Artificial Sequence
<220> FEATURE:
<223> OTHER INFORMATION: H4L2 Heavy chain

<400> SEQUENCE: 48

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Gln Ser
        115                 120                 125

Gly Gly Gly Leu Val Gln Pro Gly Gly Ser Leu Arg Leu Ser Cys Ala
    130                 135                 140

Gly Ser Gly Phe Thr Phe Ser Ser Tyr Val Met His Trp Leu Arg Gln
145                 150                 155                 160

Ala Pro Gly Lys Gly Leu Glu Trp Val Ser Val Ile Gly Thr Gly Gly
                165                 170                 175

Val Thr His Tyr Ala Asp Ser Val Lys Gly Arg Phe Thr Ile Ser Arg
            180                 185                 190

Asp Asn Ala Lys Asn Ser Leu Tyr Leu Gln Met Asn Ser Leu Arg Ala
        195                 200                 205

Glu Asp Thr Ala Val Tyr Tyr Cys Ala Arg Trp Gly Tyr Tyr Gly Ser
    210                 215                 220

Gly Ser Tyr Glu Asn Asp Ala Phe Asp Ile Trp Gly Gln Gly Thr Met
225                 230                 235                 240

Val Thr Val Ser Ser Ala Ser Thr Lys Gly Pro Ser Val Phe Pro Leu
                245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val Glu Pro Lys Cys Glu Phe
            340                 345

<210> SEQ ID NO 49

<211> LENGTH: 328
<212> TYPE: PRT
<213> ORGANISM: Artificial Sequence
<220> FEATURE:
<223> OTHER INFORMATION: H4L5 Light chain

<400> SEQUENCE: 49

```
Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Thr Lys Leu Thr Val Leu Gly
            100                 105                 110

Asp Asp Asp Asp Lys Leu Thr Gln Ser Pro Gly Thr Leu Ser Leu Ser
            115                 120                 125

Pro Gly Glu Arg Ala Thr Leu Ser Cys Arg Ala Ser Gln Ser Val Ser
130                 135                 140

Ser Ser Tyr Leu Ala Trp Tyr Gln Gln Lys Pro Gly Gln Ala Pro Arg
145                 150                 155                 160

Leu Leu Ile Tyr Gly Ala Ser Ser Arg Ala Thr Gly Ile Pro Asp Arg
                165                 170                 175

Phe Ser Gly Ser Gly Ser Gly Thr Asp Phe Thr Leu Thr Ile Ser Arg
            180                 185                 190

Leu Glu Pro Glu Asp Phe Ala Val Tyr Tyr Cys Gln Gln Tyr Ser Ser
        195                 200                 205

Ser Leu Thr Phe Gly Gly Gly Thr Lys Val Glu Ile Lys Arg Thr Val
    210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
            260                 265                 270

Ser Gln Glu Ser Val Thr Glu Gln Asp Ser Lys Asp Ser Thr Tyr Ser
        275                 280                 285

Leu Ser Ser Thr Leu Thr Leu Ser Lys Ala Asp Tyr Glu Lys His Lys
    290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325
```

<210> SEQ ID NO 50
<211> LENGTH: 349
<212> TYPE: PRT
<213> ORGANISM: Artificial Sequence
<220> FEATURE:
<223> OTHER INFORMATION: H4L5 Heavy chain

<400> SEQUENCE: 50

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Gln Ser
        115                 120                 125

Gly Gly Gly Leu Val Gln Pro Gly Gly Ser Leu Arg Leu Ser Cys Ala
130                 135                 140

Gly Ser Gly Phe Thr Phe Ser Ser Tyr Val Met His Trp Leu Arg Gln
145                 150                 155                 160

Ala Pro Gly Lys Gly Leu Glu Trp Val Ser Val Ile Gly Thr Gly Gly
            165                 170                 175

Val Thr His Tyr Ala Asp Ser Val Lys Gly Arg Phe Thr Ile Ser Arg
            180                 185                 190

Asp Asn Ala Lys Asn Ser Leu Tyr Leu Gln Met Asn Ser Leu Arg Ala
            195                 200                 205

Glu Asp Thr Ala Val Tyr Tyr Cys Ala Arg Trp Gly Tyr Tyr Gly Ser
    210                 215                 220

Gly Ser Tyr Glu Asn Asp Ala Phe Asp Ile Trp Gly Gln Gly Thr Met
225                 230                 235                 240

Val Thr Val Ser Ser Ala Ser Thr Lys Gly Pro Ser Val Phe Pro Leu
            245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
            275                 280                 285

Gly Ala Leu Thr Ser Gly Val His Thr Phe Pro Ala Val Leu Gln Ser
290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
            325                 330                 335

Thr Lys Val Asp Lys Lys Val Glu Pro Lys Cys Glu Phe
            340                 345
```

<210> SEQ ID NO 51
<211> LENGTH: 327
<212> TYPE: PRT
<213> ORGANISM: Artificial Sequence
<220> FEATURE:
<223> OTHER INFORMATION: H4L7

<400> SEQUENCE: 51

Asp Ile Val Leu Thr Gln Pro His Ser Val Ser Ala Ser Pro Gly Lys

```
            1               5                  10                 15
          Thr Val Thr Ile Ser Cys Thr Arg Ser Ser Gly Ser Val Ala Ser Tyr
                          20                 25                 30

Tyr Val Gln Trp Tyr Gln Gln Arg Pro Gly Ser Ser Pro Thr Thr Val
                          35                 40                 45

Ile Tyr Glu Asp Asn His Arg Pro Ser Gly Val Pro Asp Arg Phe Ser
                          50                 55                 60

Gly Ser Ile Asp Thr Ser Ser Asn Ser Ala Ser Leu Thr Ile Ser Gly
          65                  70                 75                 80

Leu Lys Thr Glu Asp Glu Ala Asp Tyr Tyr Cys Gln Ser Tyr Asp Ser
                          85                 90                 95

Asn Asn Leu Val Val Phe Gly Gly Thr Lys Leu Thr Val Leu Gly
                          100                105                110

Ala Ser Asp Asp Asp Lys Ser Pro Gly Thr Leu Ser Leu Ser Pro
                          115                120                125

Gly Glu Arg Ala Thr Leu Ser Cys Arg Ala Ser Gln Ser Val Ser Ser
          130                 135                140

Ser Tyr Leu Ala Trp Tyr Gln Gln Lys Pro Gly Gln Ala Pro Arg Leu
          145                 150                155                160

Leu Ile Tyr Gly Ala Ser Ser Arg Ala Thr Gly Ile Pro Asp Arg Phe
                          165                170                175

Ser Gly Ser Gly Ser Gly Thr Asp Phe Thr Leu Thr Ile Ser Arg Leu
                          180                185                190

Glu Pro Glu Asp Phe Ala Val Tyr Tyr Cys Gln Gln Tyr Ser Ser Ser
                          195                200                205

Leu Thr Phe Gly Gly Gly Thr Lys Val Glu Ile Lys Arg Thr Val Ala
          210                 215                220

Ala Pro Ser Val Phe Ile Phe Pro Pro Ser Asp Glu Gln Leu Lys Ser
          225                 230                235                240

Gly Thr Ala Ser Val Val Cys Leu Leu Asn Asn Phe Tyr Pro Arg Glu
                          245                250                255

Ala Lys Val Gln Trp Lys Val Asp Asn Ala Leu Gln Ser Gly Asn Ser
                          260                265                270

Gln Glu Ser Val Thr Glu Gln Asp Ser Lys Asp Ser Thr Tyr Ser Leu
                          275                280                285

Ser Ser Thr Leu Thr Leu Ser Lys Ala Asp Tyr Glu Lys His Lys Val
                          290                295                300

Tyr Ala Cys Glu Val Thr His Gln Gly Leu Ser Ser Pro Val Thr Lys
          305                 310                315                320

Ser Phe Asn Arg Gly Glu Cys
                          325

<210> SEQ ID NO 52
<211> LENGTH: 349
<212> TYPE: PRT
<213> ORGANISM: Artificial Sequence
<220> FEATURE:
<223> OTHER INFORMATION: H4L7 Heavy chain

<400> SEQUENCE: 52

Gln Val Gln Leu Val Glu Ser Gly Gly Thr Leu Val Gln Pro Gly Gly
          1                   5                  10                 15

Ser Leu Arg Leu Ser Cys Ala Ala Ser Gly Phe Ser Phe Thr Asp Ala
                          20                 25                 30

Trp Met Ser Trp Val Arg Gln Ala Pro Gly Lys Glu Leu Glu Trp Val
```

```
                35                  40                  45
Ser Ser Ile Ser Gly Ser Gly Gly Ser Thr Tyr Tyr Ala Gly Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Gln Ser
115                 120                 125

Gly Gly Gly Leu Val Gln Pro Gly Gly Ser Leu Arg Leu Ser Cys Ala
130                 135                 140

Gly Ser Gly Phe Thr Phe Ser Ser Tyr Val Met His Trp Leu Arg Gln
145                 150                 155                 160

Ala Pro Gly Lys Gly Leu Glu Trp Val Ser Val Ile Gly Thr Gly Gly
                165                 170                 175

Val Thr His Tyr Ala Asp Ser Val Lys Gly Arg Phe Thr Ile Ser Arg
            180                 185                 190

Asp Asn Ala Lys Asn Ser Leu Tyr Leu Gln Met Asn Ser Leu Arg Ala
            195                 200                 205

Glu Asp Thr Ala Val Tyr Tyr Cys Ala Arg Trp Gly Tyr Tyr Gly Ser
210                 215                 220

Gly Ser Tyr Glu Asn Asp Ala Phe Asp Ile Trp Gly Gln Gly Thr Met
225                 230                 235                 240

Val Thr Val Ser Ser Ala Ser Thr Lys Gly Pro Ser Val Phe Pro Leu
                245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
            275                 280                 285

Gly Ala Leu Thr Ser Gly Val His Thr Phe Pro Ala Val Leu Gln Ser
290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val Glu Pro Lys Cys Glu Phe
            340                 345

<210> SEQ ID NO 53
<211> LENGTH: 328
<212> TYPE: PRT
<213> ORGANISM: Artificial Sequence
<220> FEATURE:
<223> OTHER INFORMATION: H5L5 Light chain

<400> SEQUENCE: 53

Asp Ile Val Leu Thr Gln Pro His Ser Val Ser Ala Ser Pro Gly Lys
 1               5                  10                  15

Thr Val Thr Ile Ser Cys Thr Arg Ser Ser Gly Ser Val Ala Ser Tyr
                 20                  25                  30

Tyr Val Gln Trp Tyr Gln Gln Arg Pro Gly Ser Ser Pro Thr Thr Val
                 35                  40                  45

Ile Tyr Glu Asp Asn His Arg Pro Ser Gly Val Pro Asp Arg Phe Ser
```

```
                 50                  55                  60
Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                     85                  90                  95

Asn Asn Leu Val Val Phe Gly Gly Gly Thr Lys Leu Thr Val Leu Gly
                    100                 105                 110

Asp Asp Asp Asp Lys Leu Thr Gln Ser Pro Gly Thr Leu Ser Leu Ser
                115                 120                 125

Pro Gly Glu Arg Ala Thr Leu Ser Cys Arg Ala Ser Gln Ser Val Ser
            130                 135                 140

Ser Ser Tyr Leu Ala Trp Tyr Gln Gln Lys Pro Gly Gln Ala Pro Arg
145                 150                 155                 160

Leu Leu Ile Tyr Gly Ala Ser Ser Arg Ala Thr Gly Ile Pro Asp Arg
                165                 170                 175

Phe Ser Gly Ser Gly Ser Gly Thr Asp Phe Thr Leu Thr Ile Ser Arg
                180                 185                 190

Leu Glu Pro Glu Asp Phe Ala Val Tyr Tyr Cys Gln Gln Tyr Ser Ser
                195                 200                 205

Ser Leu Thr Phe Gly Gly Gly Thr Lys Val Glu Ile Lys Arg Thr Val
210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
                260                 265                 270

Ser Gln Glu Ser Val Thr Glu Gln Asp Ser Lys Asp Ser Thr Tyr Ser
                275                 280                 285

Leu Ser Ser Thr Leu Thr Leu Ser Lys Ala Asp Tyr Glu Lys His Lys
                290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325

<210> SEQ ID NO 54
<211> LENGTH: 347
<212> TYPE: PRT
<213> ORGANISM: Artificial Sequence
<220> FEATURE:
<223> OTHER INFORMATION: H5L5 Heavy chain

<400> SEQUENCE: 54

Gln Val Gln Leu Val Glu Ser Gly Gly Thr Leu Val Gln Pro Gly Gly
 1               5                  10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
            35                  40                  45

Ser Ser Ile Ser Gly Ser Gly Ser Thr Tyr Tyr Ala Gly Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
            85                  90                  95
Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp
            115                 120                 125

Lys Leu Val Gln Pro Gly Gly Ser Leu Arg Leu Ser Cys Ala Gly Ser
130                 135                 140

Gly Phe Thr Phe Ser Ser Tyr Val Met His Trp Leu Arg Gln Ala Pro
145                 150                 155                 160

Gly Lys Gly Leu Glu Trp Val Ser Val Ile Gly Thr Gly Gly Val Thr
            165                 170                 175

His Tyr Ala Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg Trp Gly Tyr Tyr Gly Ser Gly Ser
            210                 215                 220

Tyr Glu Asn Asp Ala Phe Asp Ile Trp Gly Gln Gly Thr Met Val Thr
225                 230                 235                 240

Val Ser Ser Ala Ser Thr Lys Gly Pro Ser Val Phe Pro Leu Ala Pro
            245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Glu Pro Lys Cys Glu Phe
            340                 345

<210> SEQ ID NO 55
<211> LENGTH: 333
<212> TYPE: PRT
<213> ORGANISM: Artificial Sequence
<220> FEATURE:
<223> OTHER INFORMATION: 3E10-Linker1-19G9 Light chain

<400> SEQUENCE: 55

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
            50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
            85                  90                  95

Asn Asn Leu Val Val Phe Gly Gly Gly Thr Lys Leu Thr Val Leu Gly
```

```
            100                 105                 110
Ala Ser Asp Asp Asp Lys Glu Ile Val Leu Thr Gln Ser Pro Gly
        115                 120                 125

Thr Leu Ser Leu Ser Pro Gly Glu Arg Ala Thr Leu Ser Cys Arg Ala
    130                 135                 140

Ser Gln Ser Val Ser Ser Ser Tyr Leu Ala Trp Tyr Gln Gln Lys Pro
145                 150                 155                 160

Gly Gln Ala Pro Arg Leu Leu Ile Tyr Gly Ala Ser Ser Arg Ala Thr
                165                 170                 175

Gly Ile Pro Asp Arg Phe Ser Gly Ser Gly Ser Gly Thr Asp Phe Thr
            180                 185                 190

Leu Thr Ile Ser Arg Leu Glu Pro Glu Asp Phe Ala Val Tyr Tyr Cys
        195                 200                 205

Gln Gln Tyr Ser Ser Ser Leu Thr Phe Gly Gly Gly Thr Lys Val Glu
    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 56
<211> LENGTH: 583
<212> TYPE: PRT
<213> ORGANISM: Artificial Sequence
<220> FEATURE:
<223> OTHER INFORMATION: 3E10-Linker1-19G9 Heavy chain

<400> SEQUENCE: 56

Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Glu Val Gln Leu Val Gln Ser Gly Gly Gly Leu Val Gln Pro Gly
```

-continued

```
            130                 135                 140
Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
                165                 170                 175

Val Ser Val Ile Gly Thr Gly Gly Val Thr His Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Arg Val Glu
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560
```

-continued

Cys Ser Val Met His Glu Ala Leu His Asn His Tyr Thr Gln Lys Ser
            565                 570                 575

Leu Ser Leu Ser Pro Gly Lys
            580

<210> SEQ ID NO 57
<211> LENGTH: 337
<212> TYPE: PRT
<213> ORGANISM: Artificial Sequence
<220> FEATURE:
<223> OTHER INFORMATION: 3E10-Linker2-19G9 Light chain

<400> SEQUENCE: 57

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Gly Gly Gly Ser Asp Asp Asp Lys Glu Ile Val Leu Thr
        115                 120                 125

Gln Ser Pro Gly Thr Leu Ser Leu Ser Pro Gly Glu Arg Ala Thr Leu
    130                 135                 140

Ser Cys Arg Ala Ser Gln Ser Val Ser Ser Ser Tyr Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Tyr Ser Ser Ser Leu Thr Phe Gly Gly Gly
    210                 215                 220

Thr Lys Val Glu Ile Lys Arg Thr Val Ala Ala Pro Ser Val Phe Ile
225                 230                 235                 240

Phe Pro Pro Ser Asp Glu Gln Leu Lys Ser Gly Thr Ala Ser Val Val
                245                 250                 255

Cys Leu Leu Asn Asn Phe Tyr Pro Arg Glu Ala Lys Val Gln Trp Lys
            260                 265                 270

Val Asp Asn Ala Leu Gln Ser Gly Asn Ser Gln Glu Ser Val Thr Glu
        275                 280                 285

Gln Asp Ser Lys Asp Ser Thr Tyr Ser Leu Ser Ser Thr Leu Thr Leu
    290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
                325                 330                 335

Cys

<210> SEQ ID NO 58
<211> LENGTH: 587
<212> TYPE: PRT
<213> ORGANISM: Artificial Sequence
<220> FEATURE:
<223> OTHER INFORMATION: 3E10-Linker2-19G9 Heavy chain

<400> SEQUENCE: 58

```
Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Gly Gly Gly Gly Ser
        115                 120                 125

Asp Asp Asp Asp Lys Glu Val Gln Leu Val Gln Ser Gly Gly Gly Leu
    130                 135                 140

Val Gln Pro Gly Gly Ser Leu Arg Leu Ser Cys Ala Gly Ser Gly Phe
145                 150                 155                 160

Thr Phe Ser Ser Tyr Val Met His Trp Leu Arg Gln Ala Pro Gly Lys
                165                 170                 175

Gly Leu Glu Trp Val Ser Val Ile Gly Thr Gly Gly Val Thr His Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Trp Gly Tyr Tyr Gly Ser Gly Ser Tyr Glu
225                 230                 235                 240

Asn Asp Ala Phe Asp Ile Trp Gly Gln Gly Thr Met Val Thr Val Ser
                245                 250                 255

Ser Ala Ser Thr Lys Gly Pro Ser Val Phe Pro Leu Ala Pro Ser Ser
            260                 265                 270

Lys Ser Thr Ser Gly Gly Thr Ala Ala Leu Gly Cys Leu Val Lys Asp
        275                 280                 285

Tyr Phe Pro Glu Pro Val Thr Val Ser Trp Asn Ser Gly Ala Leu Thr
    290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Gln
                325                 330                 335

Thr Tyr Ile Cys Asn Val Asn His Lys Pro Ser Asn Thr Lys Val Asp
            340                 345                 350
```

```
Lys Arg Val Glu Pro Lys Ser Cys Asp Lys Thr His Thr Cys Pro Pro
            355                 360                 365

Cys Pro Ala Pro Glu Leu Leu Gly Gly Pro Ser Val Phe Leu Phe Pro
370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Glu
                485                 490                 495

Glu Met Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
    530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 59
<211> LENGTH: 342
<212> TYPE: PRT
<213> ORGANISM: Artificial Sequence
<220> FEATURE:
<223> OTHER INFORMATION: 3E10-Linker3-19G9 Light chain

<400> SEQUENCE: 59

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Gly Gly Gly Ser Asp Asp Asp Lys Gly Gly Gly Ser
        115                 120                 125
```

```
Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Tyr Leu Ala Trp Tyr Gln Gln Lys Pro Gly Gln Ala Pro Arg Leu Leu
                165                 170                 175

Ile Tyr Gly Ala Ser Ser Arg Ala Thr Gly Ile Pro Asp Arg Phe Ser
                180                 185                 190

Gly Ser Gly Ser Gly Thr Asp Phe Thr Leu Thr Ile Ser Arg Leu Glu
                195                 200                 205

Pro Glu Asp Phe Ala Val Tyr Tyr Cys Gln Gln Tyr Ser Ser Ser Leu
210                 215                 220

Thr Phe Gly Gly Gly Thr Lys Val Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
                260                 265                 270

Lys Val Gln Trp Lys Val Asp Asn Ala Leu Gln Ser Gly Asn Ser Gln
                275                 280                 285

Glu Ser Val Thr Glu Gln Asp Ser Lys Asp Ser Thr Tyr Ser Leu Ser
290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
                340

<210> SEQ ID NO 60
<211> LENGTH: 592
<212> TYPE: PRT
<213> ORGANISM: Artificial Sequence
<220> FEATURE:
<223> OTHER INFORMATION: 3E10-Linker3-19G9 Heavy chain

<400> SEQUENCE: 60

Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
            35                  40                  45

Ser Ser Ile Ser Gly Ser Gly Gly Ser Thr Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
                100                 105                 110

Trp Gly Gln Gly Thr Leu Val Thr Val Ser Ala Gly Gly Gly Gly Ser
            115                 120                 125

Asp Asp Asp Asp Lys Gly Gly Gly Ser Glu Val Gln Leu Val Gln
    130                 135                 140
```

-continued

```
Ser Gly Gly Gly Leu Val Gln Pro Gly Gly Ser Leu Arg Leu Ser Cys
145                 150                 155                 160

Ala Gly Ser Gly Phe Thr Phe Ser Ser Tyr Val Met His Trp Leu Arg
                165                 170                 175

Gln Ala Pro Gly Lys Gly Leu Glu Trp Val Ser Val Ile Gly Thr Gly
            180                 185                 190

Gly Val Thr His Tyr Ala Asp Ser Val Lys Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Arg Trp Gly Tyr Tyr Gly
225                 230                 235                 240

Ser Gly Ser Tyr Glu Asn Asp Ala Phe Asp Ile Trp Gly Gln Gly Thr
                245                 250                 255

Met Val Thr Val Ser Ser Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Arg Val Glu Pro Lys Ser Cys Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
            485                 490                 495

Pro Pro Ser Arg Glu Glu Met Thr Lys Asn Gln Val Ser Leu Thr Cys
        500                 505                 510

Leu Val Lys Gly Phe Tyr Pro Ser Asp Ile Ala Val Glu Trp Glu Ser
    515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
```

```
                        565                 570                 575
Leu His Asn His Tyr Thr Gln Lys Ser Leu Ser Leu Ser Pro Gly Lys
                580                 585                 590

<210> SEQ ID NO 61
<211> LENGTH: 342
<212> TYPE: PRT
<213> ORGANISM: Artificial Sequence
<220> FEATURE:
<223> OTHER INFORMATION: 3E10-Linker4-19G9 Light chain

<400> SEQUENCE: 61

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Gly Gly Gly Ser Gly Gly Gly Ser Gly Gly Gly Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Tyr Leu Ala Trp Tyr Gln Gln Lys Pro Gly Gln Ala Pro Arg Leu Leu
                165                 170                 175

Ile Tyr Gly Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Tyr Ser Ser Ser Leu
    210                 215                 220

Thr Phe Gly Gly Gly Thr Lys Val Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
```

<210> SEQ ID NO 62
<211> LENGTH: 592
<212> TYPE: PRT
<213> ORGANISM: Artificial Sequence
<220> FEATURE:
<223> OTHER INFORMATION: 3E10-Linker4-19G9 Heavy chain

<400> SEQUENCE: 62

```
Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Gly Gly Gly Gly Ser
        115                 120                 125

Gly Gly Gly Gly Ser Gly Gly Gly Ser Glu Val Gln Leu Val Gln
130                 135                 140

Ser Gly Gly Gly Leu Val Gln Pro Gly Gly Ser Leu Arg Leu Ser Cys
145                 150                 155                 160

Ala Gly Ser Gly Phe Thr Phe Ser Ser Tyr Val Met His Trp Leu Arg
                165                 170                 175

Gln Ala Pro Gly Lys Gly Leu Glu Trp Val Ser Val Ile Gly Thr Gly
            180                 185                 190

Gly Val Thr His Tyr Ala Asp Ser Val Lys Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Arg Trp Gly Tyr Tyr Gly
225                 230                 235                 240

Ser Gly Ser Tyr Glu Asn Asp Ala Phe Asp Ile Trp Gly Gln Gly Thr
                245                 250                 255

Met Val Thr Val Ser Ser Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Arg Val Glu Pro Lys Ser Cys Asp Lys Thr
```

```
                355                 360                 365
His Thr Cys Pro Pro Cys Pro Ala Pro Glu Leu Leu Gly Pro Ser
370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                    405                 410                 415

Glu Val Lys Phe Asn Trp Tyr Val Asp Gly Val Glu Val His Asn Ala
                420                 425                 430

Lys Thr Lys Pro Arg Glu Glu Gln Tyr Asn Ser Thr Tyr Arg Val Val
            435                 440                 445

Ser Val Leu Thr Val Leu His Gln Asp Trp Leu Asn Gly Lys Glu Tyr
        450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                    485                 490                 495

Pro Pro Ser Arg Glu Glu Met Thr Lys Asn Gln Val Ser Leu Thr Cys
                500                 505                 510

Leu Val Lys Gly Phe Tyr Pro Ser Asp Ile Ala Val Glu Trp Glu Ser
            515                 520                 525

Asn Gly Gln Pro Glu Asn Asn Tyr Lys Thr Thr Pro Val Leu Asp
        530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                    565                 570                 575

Leu His Asn His Tyr Thr Gln Lys Ser Leu Ser Leu Ser Pro Gly Lys
                580                 585                 590

<210> SEQ ID NO 63
<211> LENGTH: 333
<212> TYPE: PRT
<213> ORGANISM: Artificial Sequence
<220> FEATURE:
<223> OTHER INFORMATION: 3E10-Link1-19G9 Fab Light chain

<400> SEQUENCE: 63

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
                100                 105                 110

Ala Ser Asp Asp Asp Asp Lys Glu Ile Val Leu Thr Gln Ser Pro Gly
            115                 120                 125

Thr Leu Ser Leu Ser Pro Gly Glu Arg Ala Thr Leu Ser Cys Arg Ala
```

```
                    130                 135                 140
Ser Gln Ser Val Ser Ser Tyr Leu Ala Trp Tyr Gln Lys Pro
145                 150                 155                 160

Gly Gln Ala Pro Arg Leu Leu Ile Tyr Gly Ala Ser Ser Arg Ala Thr
                    165                 170                 175

Gly Ile Pro Asp Arg Phe Ser Gly Ser Gly Ser Gly Thr Asp Phe Thr
                    180                 185                 190

Leu Thr Ile Ser Arg Leu Glu Pro Glu Asp Phe Ala Val Tyr Tyr Cys
                    195                 200                 205

Gln Gln Tyr Ser Ser Ser Leu Thr Phe Gly Gly Gly Thr Lys Val Glu
                    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                    245                 250                 255

Asn Phe Tyr Pro Arg Glu Ala Lys Val Gln Trp Lys Val Asp Asn Ala
                    260                 265                 270

Leu Gln Ser Gly Asn Ser Gln Glu Ser Val Thr Glu Gln Asp Ser Lys
                    275                 280                 285

Asp Ser Thr Tyr Ser Leu Ser Ser Thr Leu Thr Leu Ser Lys Ala Asp
                    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Ala
                    325                 330

<210> SEQ ID NO 64
<211> LENGTH: 357
<212> TYPE: PRT
<213> ORGANISM: Artificial Sequence
<220> FEATURE:
<223> OTHER INFORMATION: 3E10-Link1-19G9 Fab Heavy chain

<400> SEQUENCE: 64

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
            35                  40                  45

Ser Ser Ile Ser Gly Ser Gly Gly Ser Thr Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
                100                 105                 110

Trp Gly Gln Gly Thr Leu Val Thr Val Ser Ala Ser Asp Asp Asp
            115                 120                 125

Lys Glu Val Gln Leu Val Gln Ser Gly Gly Gly Leu Val Gln Pro Gly
                130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
```

```
                165                 170                 175
Val Ser Val Ile Gly Thr Gly Val Thr His Tyr Ala Asp Ser Val
            180                 185                 190
Lys Gly Arg Phe Thr Ile Ser Arg Asp Asn Ala Lys Asn Ser Leu Tyr
        195                 200                 205
Leu Gln Met Asn Ser Leu Arg Ala Glu Asp Thr Ala Val Tyr Tyr Cys
    210                 215                 220
Ala Arg Trp Gly Tyr Tyr Gly Ser Gly Ser Tyr Glu Asn Asp Ala Phe
225                 230                 235                 240
Asp Ile Trp Gly Gln Gly Thr Met Val Thr Val Ser Ser Ala Ser Thr
                245                 250                 255
Lys Gly Pro Ser Val Phe Pro Leu Ala Pro Ser Ser Lys Ser Thr Ser
            260                 265                 270
Gly Gly Thr Ala Ala Leu Gly Cys Leu Val Lys Asp Tyr Phe Pro Glu
        275                 280                 285
Pro Val Thr Val Ser Trp Asn Ser Gly Ala Leu Thr Ser Gly Val His
    290                 295                 300
Thr Phe Pro Ala Val Leu Gln Ser Ser Gly Leu Tyr Ser Leu Ser Ser
305                 310                 315                 320
Val Val Thr Val Pro Ser Ser Ser Leu Gly Thr Gln Thr Tyr Ile Cys
                325                 330                 335
Asn Val Asn His Lys Pro Ser Asn Thr Lys Val Asp Lys Lys Val Glu
            340                 345                 350
Pro Lys Ser Glu Phe
        355

<210> SEQ ID NO 65
<211> LENGTH: 328
<212> TYPE: PRT
<213> ORGANISM: Artificial Sequence
<220> FEATURE:
<223> OTHER INFORMATION: H1L5 Light chain

<400> SEQUENCE: 65

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Asp Asp Asp Asp Lys Leu Thr Gln Ser Pro Gly Thr Leu Ser Leu Ser
        115                 120                 125

Pro Gly Glu Arg Ala Thr Leu Ser Cys Arg Ala Ser Gln Ser Val Ser
    130                 135                 140

Ser Ser Tyr Leu Ala Trp Tyr Gln Gln Lys Pro Gly Gln Ala Pro Arg
145                 150                 155                 160

Leu Leu Ile Tyr Gly Ala Ser Ser Arg Ala Thr Gly Ile Pro Asp Arg
```

```
                165                 170                 175
Phe Ser Gly Ser Gly Ser Gly Thr Asp Phe Thr Leu Thr Ile Ser Arg
            180                 185                 190

Leu Glu Pro Glu Asp Phe Ala Val Tyr Tyr Cys Gln Gln Tyr Ser Ser
            195                 200                 205

Ser Leu Thr Phe Gly Gly Gly Thr Lys Val Glu Ile Lys Arg Thr Val
            210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
                260                 265                 270

Ser Gln Glu Ser Val Thr Glu Gln Asp Ser Lys Asp Ser Thr Tyr Ser
                275                 280                 285

Leu Ser Ser Thr Leu Thr Leu Ser Lys Ala Asp Tyr Glu Lys His Lys
                290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325

<210> SEQ ID NO 66
<211> LENGTH: 357
<212> TYPE: PRT
<213> ORGANISM: Artificial Sequence
<220> FEATURE:
<223> OTHER INFORMATION: H1L5 Heavy chain

<400> SEQUENCE: 66

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
                100                 105                 110

Trp Gly Gln Gly Thr Leu Val Thr Val Ser Ala Ser Asp Asp Asp Asp
        115                 120                 125

Lys Glu Val Gln Leu Val Gln Ser Gly Gly Gly Leu Val Gln Pro Gly
            130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
                165                 170                 175

Val Ser Val Ile Gly Thr Gly Gly Val Thr His Tyr Ala Asp Ser Val
                180                 185                 190

Lys Gly Arg Phe Thr Ile Ser Arg Asp Asn Ala Lys Asn Ser Leu Tyr
```

```
                195                 200                 205
Leu Gln Met Asn Ser Leu Arg Ala Glu Asp Thr Ala Val Tyr Tyr Cys
    210                 215                 220
Ala Arg Trp Gly Tyr Tyr Gly Ser Gly Ser Tyr Glu Asn Asp Ala Phe
225                 230                 235                 240
Asp Ile Trp Gly Gln Gly Thr Met Val Thr Val Ser Ser Ala Ser Thr
                245                 250                 255
Lys Gly Pro Ser Val Phe Pro Leu Ala Pro Ser Ser Lys Ser Thr Ser
                260                 265                 270
Gly Gly Thr Ala Ala Leu Gly Cys Leu Val Lys Asp Tyr Phe Pro Glu
            275                 280                 285
Pro Val Thr Val Ser Trp Asn Ser Gly Ala Leu Thr Ser Gly Val His
290                 295                 300
Thr Phe Pro Ala Val Leu Gln Ser Ser Gly Leu Tyr Ser Leu Ser Ser
305                 310                 315                 320
Val Val Thr Val Pro Ser Ser Ser Leu Gly Thr Gln Thr Tyr Ile Cys
                325                 330                 335
Asn Val Asn His Lys Pro Ser Asn Thr Lys Val Asp Lys Lys Val Glu
                340                 345                 350
Pro Lys Cys Glu Phe
            355

<210> SEQ ID NO 67
<211> LENGTH: 333
<212> TYPE: PRT
<213> ORGANISM: Artificial Sequence
<220> FEATURE:
<223> OTHER INFORMATION: H2L1 Light chain

<400> SEQUENCE: 67

Asp Ile Val Leu Thr Gln Pro His Ser Val Ser Ala Ser Pro Gly Lys
1               5                   10                  15
Thr Val Thr Ile Ser Cys Thr Arg Ser Ser Gly Ser Val Ala Ser Tyr
            20                  25                  30
Tyr Val Gln Trp Tyr Gln Gln Arg Pro Gly Ser Ser Pro Thr Thr Val
        35                  40                  45
Ile Tyr Glu Asp Asn His Arg Pro Ser Gly Val Pro Asp Arg Phe Ser
    50                  55                  60
Gly Ser Ile Asp Thr Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Asp Ser
                85                  90                  95
Asn Asn Leu Val Val Phe Gly Gly Gly Thr Lys Leu Thr Val Leu Gly
                100                 105                 110
Ala Ser Asp Asp Asp Lys Glu Ile Val Leu Thr Gln Ser Pro Gly
            115                 120                 125
Thr Leu Ser Leu Ser Pro Gly Glu Arg Ala Thr Leu Ser Cys Arg Ala
        130                 135                 140
Ser Gln Ser Val Ser Ser Ser Tyr Leu Ala Trp Tyr Gln Gln Lys Pro
145                 150                 155                 160
Gly Gln Ala Pro Arg Leu Leu Ile Tyr Gly Ala Ser Ser Arg Ala Thr
                165                 170                 175
Gly Ile Pro Asp Arg Phe Ser Gly Ser Gly Ser Gly Thr Asp Phe Thr
            180                 185                 190
Leu Thr Ile Ser Arg Leu Glu Pro Glu Asp Phe Ala Val Tyr Tyr Cys
```

```
                195                 200                 205
Gln Gln Tyr Ser Ser Ser Leu Thr Phe Gly Gly Gly Thr Lys Val Glu
        210                 215                 220
Ile Lys Arg Thr Val Ala Ala Pro Ser Val Phe Ile Phe Pro Pro Ser
225                 230                 235                 240
Asp Glu Gln Leu Lys Ser Gly Thr Ala Ser Val Val Cys Leu Leu Asn
                245                 250                 255
Asn Phe Tyr Pro Arg Glu Ala Lys Val Gln Trp Lys Val Asp Asn Ala
            260                 265                 270
Leu Gln Ser Gly Asn Ser Gln Glu Ser Val Thr Glu Gln Asp Ser Lys
        275                 280                 285
Asp Ser Thr Tyr Ser Leu Ser Ser Thr Leu Thr Leu Ser Lys Ala Asp
        290                 295                 300
Tyr Glu Lys His Lys Val Tyr Ala Cys Glu Val Thr His Gln Gly Leu
305                 310                 315                 320
Ser Ser Pro Val Thr Lys Ser Phe Asn Arg Gly Glu Cys
                325                 330
```

<210> SEQ ID NO 68
<211> LENGTH: 354
<212> TYPE: PRT
<213> ORGANISM: Artificial Sequence
<220> FEATURE:
<223> OTHER INFORMATION: H2L1 Heavy chain

<400> SEQUENCE: 68

```
Gln Val Gln Leu Val Glu Ser Gly Gly Thr Leu Val Gln Pro Gly Gly
1               5                   10                  15
Ser Leu Arg Leu Ser Cys Ala Ala Ser Gly Phe Ser Phe Thr Asp Ala
            20                  25                  30
Trp Met Ser Trp Val Arg Gln Ala Pro Gly Lys Glu Leu Glu Trp Val
        35                  40                  45
Ser Ser Ile Ser Gly Ser Gly Gly Ser Thr Tyr Tyr Ala Gly Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Leu Ser Leu Thr Asp Tyr Tyr Trp Tyr Gly Met Asp Val
            100                 105                 110
Trp Gly Gln Gly Thr Leu Val Thr Val Asp Asp Asp Lys Glu Val
        115                 120                 125
Gln Leu Val Gln Ser Gly Gly Gly Leu Val Gln Pro Gly Gly Ser Leu
    130                 135                 140
Arg Leu Ser Cys Ala Gly Ser Gly Phe Thr Phe Ser Ser Tyr Val Met
145                 150                 155                 160
His Trp Leu Arg Gln Ala Pro Gly Lys Gly Leu Glu Trp Val Ser Val
                165                 170                 175
Ile Gly Thr Gly Gly Val Thr His Tyr Ala Asp Ser Val Lys Gly Arg
            180                 185                 190
Phe Thr Ile Ser Arg Asp Asn Ala Lys Asn Ser Leu Tyr Leu Gln Met
        195                 200                 205
Asn Ser Leu Arg Ala Glu Asp Thr Ala Val Tyr Tyr Cys Ala Arg Trp
    210                 215                 220
Gly Tyr Tyr Gly Ser Gly Ser Tyr Glu Asn Asp Ala Phe Asp Ile Trp
```

```
                        225                 230                 235                 240
Gly Gln Gly Thr Met Val Thr Val Ser Ser Ala Ser Thr Lys Gly Pro
                        245                 250                 255

Ser Val Phe Pro Leu Ala Pro Ser Ser Lys Ser Thr Ser Gly Gly Thr
                        260                 265                 270

Ala Ala Leu Gly Cys Leu Val Lys Asp Tyr Phe Pro Glu Pro Val Thr
                        275                 280                 285

Val Ser Trp Asn Ser Gly Ala Leu Thr Ser Gly Val His Thr Phe Pro
                        290                 295                 300

Ala Val Leu Gln Ser Ser Gly Leu Tyr Ser Leu Ser Ser Val Val Thr
305                     310                 315                 320

Val Pro Ser Ser Ser Leu Gly Thr Gln Thr Tyr Ile Cys Asn Val Asn
                        325                 330                 335

His Lys Pro Ser Asn Thr Lys Val Asp Lys Lys Val Glu Pro Lys Cys
                        340                 345                 350

Glu Phe

<210> SEQ ID NO 69
<211> LENGTH: 331
<212> TYPE: PRT
<213> ORGANISM: Artificial Sequence
<220> FEATURE:
<223> OTHER INFORMATION: H2L2 Light chain

<400> SEQUENCE: 69

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65              70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
                100                 105                 110

Asp Asp Asp Asp Lys Glu Ile Val Leu Thr Gln Ser Pro Gly Thr Leu
                115                 120                 125

Ser Leu Ser Pro Gly Glu Arg Ala Thr Leu Ser Cys Arg Ala Ser Gln
            130                 135                 140

Ser Val Ser Ser Ser Tyr Leu Ala Trp Tyr Gln Gln Lys Pro Gly Gln
145                 150                 155                 160

Ala Pro Arg Leu Leu Ile Tyr Gly Ala Ser Ser Arg Ala Thr Gly Ile
                165                 170                 175

Pro Asp Arg Phe Ser Gly Ser Gly Ser Gly Thr Asp Phe Thr Leu Thr
                180                 185                 190

Ile Ser Arg Leu Glu Pro Glu Asp Phe Ala Val Tyr Tyr Cys Gln Gln
                195                 200                 205

Tyr Ser Ser Ser Leu Thr Phe Gly Gly Gly Thr Lys Val Glu Ile Lys
            210                 215                 220

Arg Thr Val Ala Ala Pro Ser Val Phe Ile Phe Pro Pro Ser Asp Glu
225                 230                 235                 240
```

```
Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 70
<211> LENGTH: 354
<212> TYPE: PRT
<213> ORGANISM: Artificial Sequence
<220> FEATURE:
<223> OTHER INFORMATION: H2L2 Heavy chain

<400> SEQUENCE: 70

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270
```

```
Ala Ala Leu Gly Cys Leu Val Lys Asp Tyr Phe Pro Glu Pro Val Thr
            275                 280                 285
Val Ser Trp Asn Ser Gly Ala Leu Thr Ser Gly Val His Thr Phe Pro
    290                 295                 300
Ala Val Leu Gln Ser Ser Gly Leu Tyr Ser Leu Ser Ser Val Val Thr
305                 310                 315                 320
Val Pro Ser Ser Ser Leu Gly Thr Gln Thr Tyr Ile Cys Asn Val Asn
                325                 330                 335
His Lys Pro Ser Asn Thr Lys Val Asp Lys Lys Val Glu Pro Lys Cys
            340                 345                 350
Glu Phe

<210> SEQ ID NO 71
<211> LENGTH: 332
<212> TYPE: PRT
<213> ORGANISM: Artificial Sequence
<220> FEATURE:
<223> OTHER INFORMATION: H2L4 Light chain

<400> SEQUENCE: 71

Asp Ile Val Leu Thr Gln Pro His Ser Val Ser Ala Ser Pro Gly Lys
1               5                   10                  15
Thr Val Thr Ile Ser Cys Thr Arg Ser Ser Gly Ser Val Ala Ser Tyr
            20                  25                  30
Tyr Val Gln Trp Tyr Gln Gln Arg Pro Gly Ser Ser Pro Thr Thr Val
        35                  40                  45
Ile Tyr Glu Asp Asn His Arg Pro Ser Gly Val Pro Asp Arg Phe Ser
    50                  55                  60
Gly Ser Ile Asp Thr Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Asp Ser
                85                  90                  95
Asn Asn Leu Val Val Phe Gly Gly Gly Thr Lys Leu Thr Val Leu Gly
            100                 105                 110
Ala Ser Ala Ser Asp Asp Asp Lys Leu Thr Gln Ser Pro Gly Thr
        115                 120                 125
Leu Ser Leu Ser Pro Gly Glu Arg Ala Thr Leu Ser Cys Arg Ala Ser
    130                 135                 140
Gln Ser Val Ser Ser Ser Tyr Leu Ala Trp Tyr Gln Gln Lys Pro Gly
145                 150                 155                 160
Gln Ala Pro Arg Leu Leu Ile Tyr Gly Ala Ser Ser Arg Ala Thr Gly
                165                 170                 175
Ile Pro Asp Arg Phe Ser Gly Ser Gly Ser Gly Thr Asp Phe Thr Leu
            180                 185                 190
Thr Ile Ser Arg Leu Glu Pro Glu Asp Phe Ala Val Tyr Tyr Cys Gln
        195                 200                 205
Gln Tyr Ser Ser Ser Leu Thr Phe Gly Gly Gly Thr Lys Val Glu Ile
    210                 215                 220
Lys Arg Thr Val Ala Ala Pro Ser Val Phe Ile Phe Pro Pro Ser Asp
225                 230                 235                 240
Glu Gln Leu Lys Ser Gly Thr Ala Ser Val Val Cys Leu Leu Asn Asn
                245                 250                 255
Phe Tyr Pro Arg Glu Ala Lys Val Gln Trp Lys Val Asp Asn Ala Leu
            260                 265                 270
```

-continued

```
Gln Ser Gly Asn Ser Gln Glu Ser Val Thr Glu Gln Asp Ser Lys Asp
            275                 280                 285

Ser Thr Tyr Ser Leu Ser Ser Thr Leu Thr Leu Ser Lys Ala Asp Tyr
290                 295                 300

Glu Lys His Lys Val Tyr Ala Cys Glu Val Thr His Gln Gly Leu Ser
305                 310                 315                 320

Ser Pro Val Thr Lys Ser Phe Asn Arg Gly Glu Cys
                325                 330

<210> SEQ ID NO 72
<211> LENGTH: 354
<212> TYPE: PRT
<213> ORGANISM: Artificial Sequence
<220> FEATURE:
<223> OTHER INFORMATION: H2L4 Heavy chain

<400> SEQUENCE: 72

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300
```

```
Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
            325                 330                 335

His Lys Pro Ser Asn Thr Lys Val Asp Lys Lys Val Glu Pro Lys Cys
            340                 345                 350

Glu Phe

<210> SEQ ID NO 73
<211> LENGTH: 328
<212> TYPE: PRT
<213> ORGANISM: Artificial Sequence
<220> FEATURE:
<223> OTHER INFORMATION: H2L5 Light chain

<400> SEQUENCE: 73

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Asp Asp Asp Asp Lys Leu Thr Gln Ser Pro Gly Thr Leu Ser Leu Ser
        115                 120                 125

Pro Gly Glu Arg Ala Thr Leu Ser Cys Arg Ala Ser Gln Ser Val Ser
130                 135                 140

Ser Ser Tyr Leu Ala Trp Tyr Gln Gln Lys Pro Gly Gln Ala Pro Arg
145                 150                 155                 160

Leu Leu Ile Tyr Gly Ala Ser Ser Arg Ala Thr Gly Ile Pro Asp Arg
                165                 170                 175

Phe Ser Gly Ser Gly Ser Gly Thr Asp Phe Thr Leu Thr Ile Ser Arg
            180                 185                 190

Leu Glu Pro Glu Asp Phe Ala Val Tyr Tyr Cys Gln Gln Tyr Ser Ser
        195                 200                 205

Ser Leu Thr Phe Gly Gly Gly Thr Lys Val Glu Ile Lys Arg Thr Val
    210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
            260                 265                 270

Ser Gln Glu Ser Val Thr Glu Gln Asp Ser Lys Asp Ser Thr Tyr Ser
        275                 280                 285

Leu Ser Ser Thr Leu Thr Leu Ser Lys Ala Asp Tyr Glu Lys His Lys
    290                 295                 300

Val Tyr Ala Cys Glu Val Thr His Gln Gly Leu Ser Ser Pro Val Thr
```

Lys Ser Phe Asn Arg Gly Glu Cys
                325

<210> SEQ ID NO 74
<211> LENGTH: 354
<212> TYPE: PRT
<213> ORGANISM: Artificial Sequence
<220> FEATURE:
<223> OTHER INFORMATION: H2L5 Heavy chain

<400> SEQUENCE: 74

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Glu Val
            115                 120                 125

Gln Leu Val Gln Ser Gly Gly Gly Leu Val Gln Pro Gly Gly Ser Leu
        130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys

Glu Phe

<210> SEQ ID NO 75
<211> LENGTH: 327
<212> TYPE: PRT
<213> ORGANISM: Artificial Sequence
<220> FEATURE:
<223> OTHER INFORMATION: H2L7 Light chain

<400> SEQUENCE: 75

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Ser Pro Gly Thr Leu Ser Leu Ser Pro
            115                 120                 125

Gly Glu Arg Ala Thr Leu Ser Cys Arg Ala Ser Gln Ser Val Ser Ser
130                 135                 140

Ser Tyr Leu Ala Trp Tyr Gln Gln Lys Pro Gly Gln Ala Pro Arg Leu
145                 150                 155                 160

Leu Ile Tyr Gly Ala Ser Ser Arg Ala Thr Gly Ile Pro Asp Arg Phe
                165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys Gln Gln Tyr Ser Ser Ser
        195                 200                 205

Leu Thr Phe Gly Gly Gly Thr Lys Val Glu Ile Lys Arg Thr Val Ala
    210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
            260                 265                 270

Gln Glu Ser Val Thr Glu Gln Asp Ser Lys Asp Ser Thr Tyr Ser Leu
        275                 280                 285

Ser Ser Thr Leu Thr Leu Ser Lys Ala Asp Tyr Glu Lys His Lys Val
    290                 295                 300

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 76

<211> LENGTH: 354
<212> TYPE: PRT
<213> ORGANISM: Artificial Sequence
<220> FEATURE:
<223> OTHER INFORMATION: H2L7 Heavy chain

<400> SEQUENCE: 76

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe
```

<210> SEQ ID NO 77
<211> LENGTH: 325

```
<212> TYPE: PRT
<213> ORGANISM: Artificial Sequence
<220> FEATURE:
<223> OTHER INFORMATION: H2L8 Light chain

<400> SEQUENCE: 77

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Asp Asp Asp Lys Ser Pro Gly Thr Leu Ser Leu Ser Pro Gly Glu
            115                 120                 125

Arg Ala Thr Leu Ser Cys Arg Ala Ser Gln Ser Val Ser Ser Ser Tyr
130                 135                 140

Leu Ala Trp Tyr Gln Gln Lys Pro Gly Gln Ala Pro Arg Leu Leu Ile
145                 150                 155                 160

Tyr Gly Ala Ser Ser Arg Ala Thr Gly Ile Pro Asp Arg Phe Ser Gly
            165                 170                 175

Ser Gly Ser Gly Thr Asp Phe Thr Leu Thr Ile Ser Arg Leu Glu Pro
            180                 185                 190

Glu Asp Phe Ala Val Tyr Tyr Cys Gln Gln Tyr Ser Ser Ser Leu Thr
            195                 200                 205

Phe Gly Gly Gly Thr Lys Val Glu Ile Lys Arg Thr Val Ala Ala Pro
210                 215                 220

Ser Val Phe Ile Phe Pro Pro Ser Asp Glu Gln Leu Lys Ser Gly Thr
225                 230                 235                 240

Ala Ser Val Val Cys Leu Leu Asn Asn Phe Tyr Pro Arg Glu Ala Lys
            245                 250                 255

Val Gln Trp Lys Val Asp Asn Ala Leu Gln Ser Gly Asn Ser Gln Glu
            260                 265                 270

Ser Val Thr Glu Gln Asp Ser Lys Asp Ser Thr Tyr Ser Leu Ser Ser
            275                 280                 285

Thr Leu Thr Leu Ser Lys Ala Asp Tyr Glu Lys His Lys Val Tyr Ala
            290                 295                 300

Cys Glu Val Thr His Gln Gly Leu Ser Ser Pro Val Thr Lys Ser Phe
305                 310                 315                 320

Asn Arg Gly Glu Cys
            325

<210> SEQ ID NO 78
<211> LENGTH: 354
<212> TYPE: PRT
<213> ORGANISM: Artificial Sequence
<220> FEATURE:
<223> OTHER INFORMATION: H2L8 Heavy chain

<400> SEQUENCE: 78
```

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
            35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Glu Val
            115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Tyr Val Met
145                 150                 155                 160

His Trp Leu Arg Gln Ala Pro Gly Lys Gly Leu Glu Trp Val Ser Val
            165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Arg Trp
210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
            245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
            290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
            325                 330                 335

His Lys Pro Ser Asn Thr Lys Val Asp Lys Lys Val Glu Pro Lys Cys
            340                 345                 350

Glu Phe

<210> SEQ ID NO 79
<211> LENGTH: 330
<212> TYPE: PRT
<213> ORGANISM: Artificial Sequence
<220> FEATURE:
<223> OTHER INFORMATION: 3E10-Linker1a-19G9 Light chain

<400> SEQUENCE: 79
```

```
Asn Phe Met Leu Thr Gln Pro His Ser Val Ser Ala Ser Pro Gly Lys
 1               5                  10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Thr Lys Leu Thr Val Ser Asp
            100                 105                 110

Asp Asp Asp Lys Glu Ile Val Leu Thr Gln Ser Pro Gly Thr Leu Ser
            115                 120                 125

Leu Ser Pro Gly Glu Arg Ala Thr Leu Ser Cys Arg Ala Ser Gln Ser
        130                 135                 140

Val Ser Ser Ser Tyr Leu Ala Trp Tyr Gln Gln Lys Pro Gly Gln Ala
145                 150                 155                 160

Pro Arg Leu Leu Ile Tyr Gly Ala Ser Ser Arg Ala Thr Gly Ile Pro
                165                 170                 175

Asp Arg Phe Ser Gly Ser Gly Ser Gly Thr Asp Phe Thr Leu Thr Ile
            180                 185                 190

Ser Arg Leu Glu Pro Glu Asp Phe Ala Val Tyr Tyr Cys Gln Gln Tyr
        195                 200                 205

Ser Ser Ser Leu Thr Phe Gly Gly Gly Thr Lys Val Glu Ile Lys Arg
210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
            260                 265                 270

Gly Asn Ser Gln Glu Ser Val Thr Glu Gln Asp Ser Lys Asp Ser Thr
        275                 280                 285

Tyr Ser Leu Ser Ser Thr Leu Thr Leu Ser Lys Ala Asp Tyr Glu Lys
        290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 80
<211> LENGTH: 580
<212> TYPE: PRT
<213> ORGANISM: Artificial Sequence
<220> FEATURE:
<223> OTHER INFORMATION: 3E10-Linker1a-19G9 Heavy chain

<400> SEQUENCE: 80

Gln Val Asn Leu Arg Glu Ser Gly Gly Thr Leu Val Gln Pro Gly Gly
 1               5                  10                  15

Ser Leu Arg Leu Ser Cys Ala Ala Ser Gly Phe Ser Thr Asp Ala
            20                  25                  30
```

-continued

```
Trp Met Ser Trp Val Arg Gln Ala Pro Gly Lys Glu Leu Glu Trp Val
         35                  40                  45

Ser Ser Ile Ser Gly Ser Gly Gly Ser Thr Tyr Tyr Ala Gly Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Ser Leu Thr Asp Tyr Tyr Trp Tyr Gly Met Asp Val
             100                 105                 110

Trp Gly Gln Gly Thr Leu Val Thr Val Asp Asp Asp Lys Glu Val
             115                 120                 125

Gln Leu Val Gln Ser Gly Gly Leu Val Gln Pro Gly Gly Ser Leu
 130                 135                 140

Arg Leu Ser Cys Ala Gly Ser Gly Phe Thr Phe Ser Ser Tyr Val Met
 145                 150                 155                 160

His Trp Leu Arg Gln Ala Pro Gly Lys Gly Leu Glu Trp Val Ser Val
                 165                 170                 175

Ile Gly Thr Gly Gly Val Thr His Tyr Ala Asp Ser Val Lys Gly Arg
             180                 185                 190

Phe Thr Ile Ser Arg Asp Asn Ala Lys Asn Ser Leu Tyr Leu Gln Met
         195                 200                 205

Asn Ser Leu Arg Ala Glu Asp Thr Ala Val Tyr Tyr Cys Ala Arg Trp
 210                 215                 220

Gly Tyr Tyr Gly Ser Gly Ser Tyr Glu Asn Asp Ala Phe Asp Ile Trp
 225                 230                 235                 240

Gly Gln Gly Thr Met Val Thr Val Ser Ser Ala Ser Thr Lys Gly Pro
                 245                 250                 255

Ser Val Phe Pro Leu Ala Pro Ser Ser Lys Ser Thr Ser Gly Gly Thr
             260                 265                 270

Ala Ala Leu Gly Cys Leu Val Lys Asp Tyr Phe Pro Glu Pro Val Thr
         275                 280                 285

Val Ser Trp Asn Ser Gly Ala Leu Thr Ser Gly Val His Thr Phe Pro
 290                 295                 300

Ala Val Leu Gln Ser Ser Gly Leu Tyr Ser Leu Ser Ser Val Val Thr
 305                 310                 315                 320

Val Pro Ser Ser Ser Leu Gly Thr Gln Thr Tyr Ile Cys Asn Val Asn
                 325                 330                 335

His Lys Pro Ser Asn Thr Lys Val Asp Lys Arg Val Glu Pro Lys Ser
             340                 345                 350

Cys Asp Lys Thr His Thr Cys Pro Pro Cys Pro Ala Pro Glu Leu Leu
         355                 360                 365

Gly Gly Pro Ser Val Phe Leu Phe Pro Pro Lys Pro Lys Asp Thr Leu
 370                 375                 380

Met Ile Ser Arg Thr Pro Glu Val Thr Cys Val Val Val Asp Val Ser
 385                 390                 395                 400

His Glu Asp Pro Glu Val Lys Phe Asn Trp Tyr Val Asp Gly Val Glu
                 405                 410                 415

Val His Asn Ala Lys Thr Lys Pro Arg Glu Glu Gln Tyr Asn Ser Thr
             420                 425                 430

Tyr Arg Val Val Ser Val Leu Thr Val Leu His Gln Asp Trp Leu Asn
         435                 440                 445

Gly Lys Glu Tyr Lys Cys Lys Val Ser Asn Lys Ala Leu Pro Ala Pro
```

```
                450                 455                 460
Ile Glu Lys Thr Ile Ser Lys Ala Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
                500                 505                 510

Glu Trp Glu Ser Asn Gly Gln Pro Glu Asn Asn Tyr Lys Thr Thr Pro
                515                 520                 525

Pro Val Leu Asp Ser Asp Gly Ser Phe Phe Leu Tyr Ser Lys Leu Thr
                530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 81
<211> LENGTH: 327
<212> TYPE: PRT
<213> ORGANISM: Artificial Sequence
<220> FEATURE:
<223> OTHER INFORMATION: 3E10-Linker1b-19G9 Light chain

<400> SEQUENCE: 81

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Ser Asp
                100                 105                 110

Asp Asp Asp Lys Leu Thr Gln Ser Pro Gly Thr Leu Ser Leu Ser Pro
            115                 120                 125

Gly Glu Arg Ala Thr Leu Ser Cys Arg Ala Ser Gln Ser Val Ser Ser
130                 135                 140

Ser Tyr Leu Ala Trp Tyr Gln Gln Lys Pro Gly Gln Ala Pro Arg Leu
145                 150                 155                 160

Leu Ile Tyr Gly Ala Ser Ser Arg Ala Thr Gly Ile Pro Asp Arg Phe
            165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys Gln Gln Tyr Ser Ser Ser
            195                 200                 205

Leu Thr Phe Gly Gly Gly Thr Lys Val Glu Ile Lys Arg Thr Val Ala
        210                 215                 220

Ala Pro Ser Val Phe Ile Phe Pro Pro Ser Asp Glu Gln Leu Lys Ser
```

```
                225                 230                 235                 240
Gly Thr Ala Ser Val Val Cys Leu Leu Asn Asn Phe Tyr Pro Arg Glu
                    245                 250                 255

Ala Lys Val Gln Trp Lys Val Asp Asn Ala Leu Gln Ser Gly Asn Ser
                260                 265                 270

Gln Glu Ser Val Thr Glu Gln Asp Ser Lys Asp Ser Thr Tyr Ser Leu
                275                 280                 285

Ser Ser Thr Leu Thr Leu Ser Lys Ala Asp Tyr Glu Lys His Lys Val
            290                 295                 300

Tyr Ala Cys Glu Val Thr His Gln Gly Leu Ser Ser Pro Val Thr Lys
305                 310                 315                 320

Ser Phe Asn Arg Gly Glu Cys
                    325

<210> SEQ ID NO 82
<211> LENGTH: 575
<212> TYPE: PRT
<213> ORGANISM: Artificial Sequence
<220> FEATURE:
<223> OTHER INFORMATION: 3E10-Linker1b-19G9 Heavy chain

<400> SEQUENCE: 82

Gln Val Asn Leu Arg Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
            35                  40                  45

Ser Ser Ile Ser Gly Ser Gly Gly Ser Thr Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
                100                 105                 110

Trp Gly Gln Gly Thr Leu Val Thr Val Asp Asp Asp Lys Gln Ser
            115                 120                 125

Gly Gly Gly Leu Val Gln Pro Gly Gly Ser Leu Arg Leu Ser Cys Ala
            130                 135                 140

Gly Ser Gly Phe Thr Phe Ser Ser Tyr Val Met His Trp Leu Arg Gln
145                 150                 155                 160

Ala Pro Gly Lys Gly Leu Glu Trp Val Ser Val Ile Gly Thr Gly Gly
                165                 170                 175

Val Thr His Tyr Ala Asp Ser Val Lys Gly Arg Phe Thr Ile Ser Arg
                180                 185                 190

Asp Asn Ala Lys Asn Ser Leu Tyr Leu Gln Met Asn Ser Leu Arg Ala
            195                 200                 205

Glu Asp Thr Ala Val Tyr Tyr Cys Ala Arg Trp Gly Tyr Tyr Gly Ser
        210                 215                 220

Gly Ser Tyr Glu Asn Asp Ala Phe Asp Ile Trp Gly Gln Gly Thr Met
225                 230                 235                 240

Val Thr Val Ser Ser Ala Ser Thr Lys Gly Pro Ser Val Phe Pro Leu
                245                 250                 255

Ala Pro Ser Ser Lys Ser Thr Ser Gly Gly Thr Ala Ala Leu Gly Cys
```

```
            260                 265                 270
Leu Val Lys Asp Tyr Phe Pro Glu Pro Val Thr Val Ser Trp Asn Ser
                275                 280                 285

Gly Ala Leu Thr Ser Gly Val His Thr Phe Pro Ala Val Leu Gln Ser
            290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Arg Val Glu Pro Lys Ser Cys Asp Lys Thr His
            340                 345                 350

Thr Cys Pro Pro Cys Pro Ala Pro Glu Leu Leu Gly Gly Pro Ser Val
            355                 360                 365

Phe Leu Phe Pro Pro Lys Pro Lys Asp Thr Leu Met Ile Ser Arg Thr
            370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
            435                 440                 445

Cys Lys Val Ser Asn Lys Ala Leu Pro Ala Pro Ile Glu Lys Thr Ile
        450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
            530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 83
<211> LENGTH: 330
<212> TYPE: PRT
<213> ORGANISM: Artificial Sequence
<220> FEATURE:
<223> OTHER INFORMATION: 3E10-Linker1c-19G9 Light chain

<400> SEQUENCE: 83

Asn Phe Met Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
```

```
                    50                  55                  60
Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                     85                  90                  95

Asn Asn Leu Val Val Phe Gly Gly Gly Thr Lys Leu Thr Val Leu Gly
                100                 105                 110

Ala Ser Asp Asp Asp Lys Leu Thr Gln Ser Pro Gly Thr Leu Ser
                115                 120                 125

Leu Ser Pro Gly Glu Arg Ala Thr Leu Ser Cys Arg Ala Ser Gln Ser
            130                 135                 140

Val Ser Ser Tyr Leu Ala Trp Tyr Gln Gln Lys Pro Gly Gln Ala
145                 150                 155                 160

Pro Arg Leu Leu Ile Tyr Gly Ala Ser Ser Arg Ala Thr Gly Ile Pro
                165                 170                 175

Asp Arg Phe Ser Gly Ser Gly Ser Gly Thr Asp Phe Thr Leu Thr Ile
                180                 185                 190

Ser Arg Leu Glu Pro Glu Asp Phe Ala Val Tyr Tyr Cys Gln Gln Tyr
            195                 200                 205

Ser Ser Ser Leu Thr Phe Gly Gly Gly Thr Lys Val Glu Ile Lys Arg
            210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
                260                 265                 270

Gly Asn Ser Gln Glu Ser Val Thr Glu Gln Asp Ser Lys Asp Ser Thr
            275                 280                 285

Tyr Ser Leu Ser Ser Thr Leu Thr Leu Ser Lys Ala Asp Tyr Glu Lys
            290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 84
<211> LENGTH: 578
<212> TYPE: PRT
<213> ORGANISM: Artificial Sequence
<220> FEATURE:
<223> OTHER INFORMATION: 3E10-Linker1c-19G9 Heavy chain

<400> SEQUENCE: 84

Gln Val Asn Leu Arg Glu Ser Gly Gly Thr Leu Val Gln Pro Gly Gly
  1               5                  10                  15

Ser Leu Arg Leu Ser Cys Ala Ala Ser Gly Phe Ser Thr Asp Ala
             20                  25                  30

Trp Met Ser Trp Val Arg Gln Ala Pro Gly Lys Glu Leu Glu Trp Val
         35                  40                  45

Ser Ser Ile Ser Gly Ser Gly Gly Ser Thr Tyr Tyr Ala Gly Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                 85                  90                  95
Ala Arg Val Leu Ser Leu Thr Asp Tyr Tyr Trp Tyr Gly Met Asp Val
            100                 105                 110
Trp Gly Gln Gly Thr Leu Val Thr Val Ser Ala Ser Asp Asp Asp
            115                 120                 125
Lys Gln Ser Gly Gly Leu Val Gln Pro Gly Ser Leu Arg Leu
        130                 135                 140
Ser Cys Ala Gly Ser Gly Phe Thr Phe Ser Ser Tyr Val Met His Trp
145                 150                 155                 160
Leu Arg Gln Ala Pro Gly Lys Gly Leu Glu Trp Val Ser Val Ile Gly
                165                 170                 175
Thr Gly Gly Val Thr His Tyr Ala Asp Ser Val Lys Gly Arg Phe Thr
                180                 185                 190
Ile Ser Arg Asp Asn Ala Lys Asn Ser Leu Tyr Leu Gln Met Asn Ser
            195                 200                 205
Leu Arg Ala Glu Asp Thr Ala Val Tyr Tyr Cys Ala Arg Trp Gly Tyr
        210                 215                 220
Tyr Gly Ser Gly Ser Tyr Glu Asn Asp Ala Phe Asp Ile Trp Gly Gln
225                 230                 235                 240
Gly Thr Met Val Thr Val Ser Ser Ala Ser Thr Lys Gly Pro Ser Val
                245                 250                 255
Phe Pro Leu Ala Pro Ser Ser Lys Ser Thr Ser Gly Gly Thr Ala Ala
            260                 265                 270
Leu Gly Cys Leu Val Lys Asp Tyr Phe Pro Glu Pro Val Thr Val Ser
        275                 280                 285
Trp Asn Ser Gly Ala Leu Thr Ser Gly Val His Thr Phe Pro Ala Val
        290                 295                 300
Leu Gln Ser Ser Gly Leu Tyr Ser Leu Ser Ser Val Val Thr Val Pro
305                 310                 315                 320
Ser Ser Ser Leu Gly Thr Gln Thr Tyr Ile Cys Asn Val Asn His Lys
                325                 330                 335
Pro Ser Asn Thr Lys Val Asp Lys Arg Val Glu Pro Lys Ser Cys Asp
            340                 345                 350
Lys Thr His Thr Cys Pro Pro Cys Pro Ala Pro Glu Leu Leu Gly Gly
        355                 360                 365
Pro Ser Val Phe Leu Phe Pro Pro Lys Pro Lys Asp Thr Leu Met Ile
        370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                405                 410                 415
Asn Ala Lys Thr Lys Pro Arg Glu Glu Gln Tyr Asn Ser Thr Tyr Arg
            420                 425                 430
Val Val Ser Val Leu Thr Val Leu His Gln Asp Trp Leu Asn Gly Lys
        435                 440                 445
Glu Tyr Lys Cys Lys Val Ser Asn Lys Ala Leu Pro Ala Pro Ile Glu
        450                 455                 460
Lys Thr Ile Ser Lys Ala Lys Gly Gln Pro Arg Glu Pro Gln Val Tyr
465                 470                 475                 480
Thr Leu Pro Pro Ser Arg Glu Glu Met Thr Lys Asn Gln Val Ser Leu
                485                 490                 495
Thr Cys Leu Val Lys Gly Phe Tyr Pro Ser Asp Ile Ala Val Glu Trp
            500                 505                 510
```

```
Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Lys Leu Thr Val Asp
            530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
            565                 570                 575

Gly Lys

<210> SEQ ID NO 85
<211> LENGTH: 333
<212> TYPE: PRT
<213> ORGANISM: Artificial Sequence
<220> FEATURE:
<223> OTHER INFORMATION: H3L1 Light chain

<400> SEQUENCE: 85

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
            85                  90                  95

Asn Asn Leu Val Val Phe Gly Gly Gly Thr Lys Leu Thr Val Leu Gly
            100                 105                 110

Ala Ser Asp Asp Asp Lys Glu Ile Val Leu Thr Gln Ser Pro Gly
            115                 120                 125

Thr Leu Ser Leu Ser Pro Gly Glu Arg Ala Thr Leu Ser Cys Arg Ala
            130                 135                 140

Ser Gln Ser Val Ser Ser Ser Tyr Leu Ala Trp Tyr Gln Gln Lys Pro
145                 150                 155                 160

Gly Gln Ala Pro Arg Leu Leu Ile Tyr Gly Ala Ser Ser Arg Ala Thr
            165                 170                 175

Gly Ile Pro Asp Arg Phe Ser Gly Ser Gly Ser Gly Thr Asp Phe Thr
            180                 185                 190

Leu Thr Ile Ser Arg Leu Glu Pro Glu Asp Phe Ala Val Tyr Tyr Cys
            195                 200                 205

Gln Gln Tyr Ser Ser Ser Leu Thr Phe Gly Gly Gly Thr Lys Val Glu
            210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
            245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
            275                 280                 285
```

```
Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330
```

<210> SEQ ID NO 86
<211> LENGTH: 352
<212> TYPE: PRT
<213> ORGANISM: Artificial Sequence
<220> FEATURE:
<223> OTHER INFORMATION: H3L1 Heavy chain

<400> SEQUENCE: 86

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Gln Ser Gly Gly Gly Leu Val Gln Pro Gly Gly Ser Leu Arg Leu
130                 135                 140

Ser Cys Ala Gly Ser Gly Phe Thr Phe Ser Ser Tyr Val Met His Trp
145                 150                 155                 160

Leu Arg Gln Ala Pro Gly Lys Gly Leu Glu Trp Val Ser Val Ile Gly
                165                 170                 175

Thr Gly Gly Val Thr His Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Trp Gly Tyr
    210                 215                 220

Tyr Gly Ser Gly Ser Tyr Glu Asn Asp Ala Phe Asp Ile Trp Gly Gln
225                 230                 235                 240

Gly Thr Met Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Leu Tyr Ser Leu Ser Ser Val Val Thr Val Pro
305                 310                 315                 320
```

```
Ser Ser Ser Leu Gly Thr Gln Thr Tyr Ile Cys Asn Val Asn His Lys
                325                 330                 335

Pro Ser Asn Thr Lys Val Asp Lys Lys Val Glu Pro Lys Cys Glu Phe
            340                 345                 350

<210> SEQ ID NO 87
<211> LENGTH: 331
<212> TYPE: PRT
<213> ORGANISM: Artificial Sequence
<220> FEATURE:
<223> OTHER INFORMATION: H3L2 Light chain

<400> SEQUENCE: 87

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Asp Asp Asp Asp Lys Glu Ile Val Leu Thr Gln Ser Pro Gly Thr Leu
        115                 120                 125

Ser Leu Ser Pro Gly Glu Arg Ala Thr Leu Ser Cys Arg Ala Ser Gln
130                 135                 140

Ser Val Ser Ser Ser Tyr Leu Ala Trp Tyr Gln Gln Lys Pro Gly Gln
145                 150                 155                 160

Ala Pro Arg Leu Leu Ile Tyr Gly Ala Ser Ser Arg Ala Thr Gly Ile
                165                 170                 175

Pro Asp Arg Phe Ser Gly Ser Gly Ser Gly Thr Asp Phe Thr Leu Thr
            180                 185                 190

Ile Ser Arg Leu Glu Pro Glu Asp Phe Ala Val Tyr Tyr Cys Gln Gln
        195                 200                 205

Tyr Ser Ser Ser Leu Thr Phe Gly Gly Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

```
<210> SEQ ID NO 88
<211> LENGTH: 352
<212> TYPE: PRT
<213> ORGANISM: Artificial Sequence
<220> FEATURE:
<223> OTHER INFORMATION: H3L2 Heavy chain

<400> SEQUENCE: 88

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Gln Ser Gly Gly Gly Leu Val Gln Pro Gly Gly Ser Leu Arg Leu
130                 135                 140

Ser Cys Ala Gly Ser Gly Phe Thr Phe Ser Ser Tyr Val Met His Trp
145                 150                 155                 160

Leu Arg Gln Ala Pro Gly Lys Gly Leu Glu Trp Val Ser Val Ile Gly
                165                 170                 175

Thr Gly Gly Val Thr His Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Trp Gly Tyr
    210                 215                 220

Tyr Gly Ser Gly Ser Tyr Glu Asn Asp Ala Phe Asp Ile Trp Gly Gln
225                 230                 235                 240

Gly Thr Met Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Lys Val Glu Pro Lys Cys Glu Phe
            340                 345                 350

<210> SEQ ID NO 89
<211> LENGTH: 330
```

<212> TYPE: PRT
<213> ORGANISM: Artificial Sequence
<220> FEATURE:
<223> OTHER INFORMATION: H3L4 Light chain

<400> SEQUENCE: 89

```
Asp Ile Val Leu Thr Gln Pro His Ser Val Ser Ala Ser Pro Gly Lys
 1               5                  10                  15
Thr Val Thr Ile Ser Cys Thr Arg Ser Ser Gly Ser Val Ala Ser Tyr
            20                  25                  30
Tyr Val Gln Trp Tyr Gln Gln Arg Pro Gly Ser Ser Pro Thr Thr Val
        35                  40                  45
Ile Tyr Glu Asp Asn His Arg Pro Ser Gly Val Pro Asp Arg Phe Ser
    50                  55                  60
Gly Ser Ile Asp Thr Ser Ser Asn Ser Ala Ser Leu Thr Ile Ser Gly
 65                  70                  75                  80
Leu Lys Thr Glu Asp Glu Ala Asp Tyr Tyr Cys Gln Ser Tyr Asp Ser
                85                  90                  95
Asn Asn Leu Val Val Phe Gly Gly Gly Thr Lys Leu Thr Val Leu Gly
            100                 105                 110
Ala Ser Asp Asp Asp Lys Leu Thr Gln Ser Pro Gly Thr Leu Ser
        115                 120                 125
Leu Ser Pro Gly Glu Arg Ala Thr Leu Ser Cys Arg Ala Ser Gln Ser
    130                 135                 140
Val Ser Ser Ser Tyr Leu Ala Trp Tyr Gln Gln Lys Pro Gly Gln Ala
145                 150                 155                 160
Pro Arg Leu Leu Ile Tyr Gly Ala Ser Ser Arg Ala Thr Gly Ile Pro
                165                 170                 175
Asp Arg Phe Ser Gly Ser Gly Ser Gly Thr Asp Phe Thr Leu Thr Ile
            180                 185                 190
Ser Arg Leu Glu Pro Glu Asp Phe Ala Val Tyr Tyr Cys Gln Gln Tyr
        195                 200                 205
Ser Ser Ser Leu Thr Phe Gly Gly Gly Thr Lys Val Glu Ile Lys Arg
    210                 215                 220
Thr Val Ala Ala Pro Ser Val Phe Ile Phe Pro Pro Ser Asp Glu Gln
225                 230                 235                 240
Leu Lys Ser Gly Thr Ala Ser Val Val Cys Leu Leu Asn Asn Phe Tyr
                245                 250                 255
Pro Arg Glu Ala Lys Val Gln Trp Lys Val Asp Asn Ala Leu Gln Ser
            260                 265                 270
Gly Asn Ser Gln Glu Ser Val Thr Glu Gln Asp Ser Lys Asp Ser Thr
        275                 280                 285
Tyr Ser Leu Ser Ser Thr Leu Thr Leu Ser Lys Ala Asp Tyr Glu Lys
    290                 295                 300
His Lys Val Tyr Ala Cys Glu Val Thr His Gln Gly Leu Ser Ser Pro
305                 310                 315                 320
Val Thr Lys Ser Phe Asn Arg Gly Glu Cys
                325                 330
```

<210> SEQ ID NO 90
<211> LENGTH: 352
<212> TYPE: PRT
<213> ORGANISM: Artificial Sequence
<220> FEATURE:
<223> OTHER INFORMATION: H3L4 Heavy chain

<400> SEQUENCE: 90

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Gln Ser Gly Gly Gly Leu Val Gln Pro Gly Gly Ser Leu Arg Leu
130                 135                 140

Ser Cys Ala Gly Ser Gly Phe Thr Phe Ser Ser Tyr Val Met His Trp
145                 150                 155                 160

Leu Arg Gln Ala Pro Gly Lys Gly Leu Glu Trp Val Ser Val Ile Gly
                165                 170                 175

Thr Gly Gly Val Thr His Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Trp Gly Tyr
210                 215                 220

Tyr Gly Ser Gly Ser Tyr Glu Asn Asp Ala Phe Asp Ile Trp Gly Gln
225                 230                 235                 240

Gly Thr Met Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Lys Val Glu Pro Lys Cys Glu Phe
            340                 345                 350

<210> SEQ ID NO 91
<211> LENGTH: 328
<212> TYPE: PRT
<213> ORGANISM: Artificial Sequence
<220> FEATURE:
<223> OTHER INFORMATION: H3L5 Light chain

<400> SEQUENCE: 91

Asp Ile Val Leu Thr Gln Pro His Ser Val Ser Ala Ser Pro Gly Lys
1               5                   10                  15

```
Thr Val Thr Ile Ser Cys Thr Arg Ser Ser Gly Ser Val Ala Ser Tyr
             20                  25                  30

Tyr Val Gln Trp Tyr Gln Gln Arg Pro Gly Ser Ser Pro Thr Thr Val
         35                  40                  45

Ile Tyr Glu Asp Asn His Arg Pro Ser Gly Val Pro Asp Arg Phe Ser
 50                  55                  60

Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asn Asn Leu Val Val Phe Gly Gly Gly Thr Lys Leu Thr Val Leu Gly
             100                 105                 110

Asp Asp Asp Lys Leu Thr Gln Ser Pro Gly Thr Leu Ser Leu Ser
             115                 120                 125

Pro Gly Glu Arg Ala Thr Leu Ser Cys Arg Ala Ser Gln Ser Val Ser
130                 135                 140

Ser Ser Tyr Leu Ala Trp Tyr Gln Gln Lys Pro Gly Gln Ala Pro Arg
145                 150                 155                 160

Leu Leu Ile Tyr Gly Ala Ser Ser Arg Ala Thr Gly Ile Pro Asp Arg
                 165                 170                 175

Phe Ser Gly Ser Gly Ser Gly Thr Asp Phe Thr Leu Thr Ile Ser Arg
             180                 185                 190

Leu Glu Pro Glu Asp Phe Ala Val Tyr Tyr Cys Gln Gln Tyr Ser Ser
             195                 200                 205

Ser Leu Thr Phe Gly Gly Gly Thr Lys Val Glu Ile Lys Arg Thr Val
210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
             245                 250                 255

Glu Ala Lys Val Gln Trp Lys Val Asp Asn Ala Leu Gln Ser Gly Asn
             260                 265                 270

Ser Gln Glu Ser Val Thr Glu Gln Asp Ser Lys Asp Ser Thr Tyr Ser
             275                 280                 285

Leu Ser Ser Thr Leu Thr Leu Ser Lys Ala Asp Tyr Glu Lys His Lys
290                 295                 300

Val Tyr Ala Cys Glu Val Thr His Gln Gly Leu Ser Ser Pro Val Thr
305                 310                 315                 320

Lys Ser Phe Asn Arg Gly Glu Cys
             325

<210> SEQ ID NO 92
<211> LENGTH: 352
<212> TYPE: PRT
<213> ORGANISM: Artificial Sequence
<220> FEATURE:
<223> OTHER INFORMATION: H3L5 Heavy chain

<400> SEQUENCE: 92

Gln Val Gln Leu Val Glu Ser Gly Gly Thr Leu Val Gln Pro Gly Gly
 1               5                  10                  15

Ser Leu Arg Leu Ser Cys Ala Ala Ser Gly Phe Ser Phe Thr Asp Ala
             20                  25                  30

Trp Met Ser Trp Val Arg Gln Ala Pro Gly Lys Glu Leu Glu Trp Val
         35                  40                  45
```

```
Ser Ser Ile Ser Gly Ser Gly Gly Ser Thr Tyr Tyr Ala Gly Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
            115                 120                 125

Lys Gln Ser Gly Gly Leu Val Gln Pro Gly Gly Ser Leu Arg Leu
    130                 135                 140

Ser Cys Ala Gly Ser Gly Phe Thr Phe Ser Ser Tyr Val Met His Trp
145                 150                 155                 160

Leu Arg Gln Ala Pro Gly Lys Gly Leu Glu Trp Val Ser Val Ile Gly
                165                 170                 175

Thr Gly Gly Val Thr His Tyr Ala Asp Ser Val Lys Gly Arg Phe Thr
                180                 185                 190

Ile Ser Arg Asp Asn Ala Lys Asn Ser Leu Tyr Leu Gln Met Asn Ser
            195                 200                 205

Leu Arg Ala Glu Asp Thr Ala Val Tyr Tyr Cys Ala Arg Trp Gly Tyr
    210                 215                 220

Tyr Gly Ser Gly Ser Tyr Glu Asn Asp Ala Phe Asp Ile Trp Gly Gln
225                 230                 235                 240

Gly Thr Met Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
                260                 265                 270

Leu Gly Cys Leu Val Lys Asp Tyr Phe Pro Glu Pro Val Thr Val Ser
            275                 280                 285

Trp Asn Ser Gly Ala Leu Thr Ser Gly Val His Thr Phe Pro Ala Val
290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Lys Val Glu Pro Lys Cys Glu Phe
                340                 345                 350

<210> SEQ ID NO 93
<211> LENGTH: 327
<212> TYPE: PRT
<213> ORGANISM: Artificial Sequence
<220> FEATURE:
<223> OTHER INFORMATION: H3L7 Light chain

<400> SEQUENCE: 93

Asp Ile Val Leu Thr Gln Pro His Ser Val Ser Ala Ser Pro Gly Lys
 1               5                  10                  15

Thr Val Thr Ile Ser Cys Thr Arg Ser Ser Gly Ser Val Ala Ser Tyr
                 20                  25                  30

Tyr Val Gln Trp Tyr Gln Gln Arg Pro Gly Ser Ser Pro Thr Thr Val
             35                  40                  45

Ile Tyr Glu Asp Asn His Arg Pro Ser Gly Val Pro Asp Arg Phe Ser
 50                  55                  60
```

```
Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
                100                 105                 110

Ala Ser Asp Asp Asp Lys Ser Pro Gly Thr Leu Ser Leu Ser Pro
            115                 120                 125

Gly Glu Arg Ala Thr Leu Ser Cys Arg Ala Ser Gln Ser Val Ser Ser
            130                 135                 140

Ser Tyr Leu Ala Trp Tyr Gln Gln Lys Pro Gly Gln Ala Pro Arg Leu
145                 150                 155                 160

Leu Ile Tyr Gly Ala Ser Ser Arg Ala Thr Gly Ile Pro Asp Arg Phe
                165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys Gln Gln Tyr Ser Ser Ser
            195                 200                 205

Leu Thr Phe Gly Gly Gly Thr Lys Val Glu Ile Lys Arg Thr Val Ala
210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
                260                 265                 270

Gln Glu Ser Val Thr Glu Gln Asp Ser Lys Asp Ser Thr Tyr Ser Leu
            275                 280                 285

Ser Ser Thr Leu Thr Leu Ser Lys Ala Asp Tyr Glu Lys His Lys Val
            290                 295                 300

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 94
<211> LENGTH: 352
<212> TYPE: PRT
<213> ORGANISM: Artificial Sequence
<220> FEATURE:
<223> OTHER INFORMATION: H3L7 Heavy chain

<400> SEQUENCE: 94

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
            35                  40                  45

Ser Ser Ile Ser Gly Ser Gly Ser Thr Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp
            115                 120                 125

Lys Gln Ser Gly Gly Leu Val Gln Pro Gly Gly Ser Leu Arg Leu
            130                 135                 140

Ser Cys Ala Gly Ser Gly Phe Thr Phe Ser Ser Tyr Val Met His Trp
145                 150                 155                 160

Leu Arg Gln Ala Pro Gly Lys Gly Leu Glu Trp Val Ser Val Ile Gly
            165                 170                 175

Thr Gly Gly Val Thr His Tyr Ala Asp Ser Val Lys Gly Arg Phe Thr
            180                 185                 190

Ile Ser Arg Asp Asn Ala Lys Asn Ser Leu Tyr Leu Gln Met Asn Ser
            195                 200                 205

Leu Arg Ala Glu Asp Thr Ala Val Tyr Tyr Cys Ala Arg Trp Gly Tyr
            210                 215                 220

Tyr Gly Ser Gly Ser Tyr Glu Asn Asp Ala Phe Asp Ile Trp Gly Gln
225                 230                 235                 240

Gly Thr Met Val Thr Val Ser Ser Ala Ser Thr Lys Gly Pro Ser Val
            245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
            275                 280                 285

Trp Asn Ser Gly Ala Leu Thr Ser Gly Val His Thr Phe Pro Ala Val
            290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
            325                 330                 335

Pro Ser Asn Thr Lys Val Asp Lys Lys Val Glu Pro Lys Cys Glu Phe
            340                 345                 350

<210> SEQ ID NO 95
<211> LENGTH: 331
<212> TYPE: PRT
<213> ORGANISM: Artificial Sequence
<220> FEATURE:
<223> OTHER INFORMATION: H1L2 Light chain

<400> SEQUENCE: 95

Asp Ile Val Leu Thr Gln Pro His Ser Val Ser Ala Ser Pro Gly Lys
1                   5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
            50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
            85                  90                  95

Asn Asn Leu Val Val Phe Gly Gly Gly Thr Lys Leu Thr Val Leu Gly
            100                 105                 110

Asp Asp Asp Asp Lys Glu Ile Val Leu Thr Gln Ser Pro Gly Thr Leu
                115                 120                 125

Ser Leu Ser Pro Gly Glu Arg Ala Thr Leu Ser Cys Arg Ala Ser Gln
    130                 135                 140

Ser Val Ser Ser Tyr Leu Ala Trp Tyr Gln Gln Lys Pro Gly Gln
145                 150                 155                 160

Ala Pro Arg Leu Leu Ile Tyr Gly Ala Ser Ser Arg Ala Thr Gly Ile
                165                 170                 175

Pro Asp Arg Phe Ser Gly Ser Gly Ser Gly Thr Asp Phe Thr Leu Thr
                180                 185                 190

Ile Ser Arg Leu Glu Pro Glu Asp Phe Ala Val Tyr Tyr Cys Gln Gln
                195                 200                 205

Tyr Ser Ser Ser Leu Thr Phe Gly Gly Gly Thr Lys Val Glu Ile Lys
                210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
                275                 280                 285

Thr Tyr Ser Leu Ser Ser Thr Leu Thr Leu Ser Lys Ala Asp Tyr Glu
                290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 96
<211> LENGTH: 357
<212> TYPE: PRT
<213> ORGANISM: Artificial Sequence
<220> FEATURE:
<223> OTHER INFORMATION: H1L2 Heavy chain

<400> SEQUENCE: 96

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
                20                  25                  30

Trp Met Ser Trp Val Arg Gln Ala Pro Gly Lys Glu Leu Glu Trp Val
                35                  40                  45

Ser Ser Ile Ser Gly Ser Gly Gly Ser Thr Tyr Tyr Ala Gly Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
                100                 105                 110

Trp Gly Gln Gly Thr Leu Val Thr Val Ser Ala Ser Asp Asp Asp Asp
            115                 120                 125

Lys Glu Val Gln Leu Val Gln Ser Gly Gly Gly Leu Val Gln Pro Gly
                130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
            165                 170                 175

Val Ser Val Ile Gly Thr Gly Val Thr His Tyr Ala Asp Ser Val
        180                 185                 190

Lys Gly Arg Phe Thr Ile Ser Arg Asp Asn Ala Lys Asn Ser Leu Tyr
            195                 200                 205

Leu Gln Met Asn Ser Leu Arg Ala Glu Asp Thr Ala Val Tyr Tyr Cys
        210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
            245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Leu Gly Thr Gln Thr Tyr Ile Cys
            325                 330                 335

Asn Val Asn His Lys Pro Ser Asn Thr Lys Val Asp Lys Lys Val Glu
            340                 345                 350

Pro Lys Cys Glu Phe
        355

<210> SEQ ID NO 97
<211> LENGTH: 333
<212> TYPE: PRT
<213> ORGANISM: Artificial Sequence
<220> FEATURE:
<223> OTHER INFORMATION: H5L1 Light chain

<400> SEQUENCE: 97

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
            85                  90                  95

Asn Asn Leu Val Val Phe Gly Gly Gly Thr Lys Leu Thr Val Leu Gly
            100                 105                 110

Ala Ser Asp Asp Asp Lys Glu Ile Val Leu Thr Gln Ser Pro Gly
        115                 120                 125

Thr Leu Ser Leu Ser Pro Gly Glu Arg Ala Thr Leu Ser Cys Arg Ala
        130                 135                 140

Ser Gln Ser Val Ser Ser Tyr Leu Ala Trp Tyr Gln Gln Lys Pro
145                 150                 155                 160

Gly Gln Ala Pro Arg Leu Leu Ile Tyr Gly Ala Ser Ser Arg Ala Thr
                165                 170                 175

Gly Ile Pro Asp Arg Phe Ser Gly Ser Gly Ser Gly Thr Asp Phe Thr
            180                 185                 190

Leu Thr Ile Ser Arg Leu Glu Pro Glu Asp Phe Ala Val Tyr Tyr Cys
        195                 200                 205

Gln Gln Tyr Ser Ser Ser Leu Thr Phe Gly Gly Gly Thr Lys Val Glu
    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 98
<211> LENGTH: 347
<212> TYPE: PRT
<213> ORGANISM: Artificial Sequence
<220> FEATURE:
<223> OTHER INFORMATION: H5L1 Heavy chain

<400> SEQUENCE: 98

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Leu Val Gln Pro Gly Gly Ser Leu Arg Leu Ser Cys Ala Gly Ser
    130                 135                 140

Gly Phe Thr Phe Ser Ser Tyr Val Met His Trp Leu Arg Gln Ala Pro
145                 150                 155                 160

Gly Lys Gly Leu Glu Trp Val Ser Val Ile Gly Thr Gly Gly Val Thr
                165                 170                 175

```
His Tyr Ala Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg Trp Gly Tyr Gly Ser Gly Ser
            210                 215                 220

Tyr Glu Asn Asp Ala Phe Asp Ile Trp Gly Gln Gly Thr Met Val Thr
225                 230                 235                 240

Val Ser Ser Ala Ser Thr Lys Gly Pro Ser Val Phe Pro Leu Ala Pro
            245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Glu Pro Lys Cys Glu Phe
            340                 345

<210> SEQ ID NO 99
<211> LENGTH: 330
<212> TYPE: PRT
<213> ORGANISM: Artificial Sequence
<220> FEATURE:
<223> OTHER INFORMATION: H5L4 Light chain

<400> SEQUENCE: 99

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Leu Thr Gln Ser Pro Gly Thr Leu Ser
            115                 120                 125

Leu Ser Pro Gly Glu Arg Ala Thr Leu Ser Cys Arg Ala Ser Gln Ser
    130                 135                 140

Val Ser Ser Ser Tyr Leu Ala Trp Tyr Gln Gln Lys Pro Gly Gln Ala
145                 150                 155                 160

Pro Arg Leu Leu Ile Tyr Gly Ala Ser Ser Arg Ala Thr Gly Ile Pro
                165                 170                 175

Asp Arg Phe Ser Gly Ser Gly Ser Gly Thr Asp Phe Thr Leu Thr Ile
            180                 185                 190
```

```
Ser Arg Leu Glu Pro Glu Asp Phe Ala Val Tyr Tyr Cys Gln Gln Tyr
        195                 200                 205

Ser Ser Ser Leu Thr Phe Gly Gly Gly Thr Lys Val Glu Ile Lys Arg
    210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
            260                 265                 270

Gly Asn Ser Gln Glu Ser Val Thr Glu Gln Asp Ser Lys Asp Ser Thr
        275                 280                 285

Tyr Ser Leu Ser Ser Thr Leu Thr Leu Ser Lys Ala Asp Tyr Glu Lys
    290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 100
<211> LENGTH: 347
<212> TYPE: PRT
<213> ORGANISM: Artificial Sequence
<220> FEATURE:
<223> OTHER INFORMATION: H5L4 Heavy chain

<400> SEQUENCE: 100

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Leu Val Gln Pro Gly Gly Ser Leu Arg Leu Ser Cys Ala Gly Ser
    130                 135                 140

Gly Phe Thr Phe Ser Ser Tyr Val Met His Trp Leu Arg Gln Ala Pro
145                 150                 155                 160

Gly Lys Gly Leu Glu Trp Val Ser Val Ile Gly Thr Gly Gly Val Thr
                165                 170                 175

His Tyr Ala Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Trp Gly Tyr Tyr Gly Ser Gly Ser
    210                 215                 220
```

-continued

Tyr Glu Asn Asp Ala Phe Asp Ile Trp Gly Gln Gly Thr Met Val Thr
225                 230                 235                 240

Val Ser Ser Ala Ser Thr Lys Gly Pro Ser Val Phe Pro Leu Ala Pro
            245                 250                 255

Ser Ser Lys Ser Thr Ser Gly Gly Thr Ala Ala Leu Gly Cys Leu Val
        260                 265                 270

Lys Asp Tyr Phe Pro Glu Pro Val Thr Val Ser Trp Asn Ser Gly Ala
    275                 280                 285

Leu Thr Ser Gly Val His Thr Phe Pro Ala Val Leu Gln Ser Ser Gly
290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Glu Pro Lys Cys Glu Phe
        340                 345

<210> SEQ ID NO 101
<211> LENGTH: 327
<212> TYPE: PRT
<213> ORGANISM: Artificial Sequence
<220> FEATURE:
<223> OTHER INFORMATION: H5L7 Light chain

<400> SEQUENCE: 101

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Ser Pro Gly Thr Leu Ser Leu Ser Pro
        115                 120                 125

Gly Glu Arg Ala Thr Leu Ser Cys Arg Ala Ser Gln Ser Val Ser Ser
    130                 135                 140

Ser Tyr Leu Ala Trp Tyr Gln Gln Lys Pro Gly Gln Ala Pro Arg Leu
145                 150                 155                 160

Leu Ile Tyr Gly Ala Ser Ser Arg Ala Thr Gly Ile Pro Asp Arg Phe
                165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys Gln Gln Tyr Ser Ser Ser
        195                 200                 205

Leu Thr Phe Gly Gly Gly Thr Lys Val Glu Ile Lys Arg Thr Val Ala
    210                 215                 220

Ala Pro Ser Val Phe Ile Phe Pro Pro Ser Asp Glu Gln Leu Lys Ser
225                 230                 235                 240

```
Gly Thr Ala Ser Val Val Cys Leu Leu Asn Asn Phe Tyr Pro Arg Glu
            245                 250                 255

Ala Lys Val Gln Trp Lys Val Asp Asn Ala Leu Gln Ser Gly Asn Ser
        260                 265                 270

Gln Glu Ser Val Thr Glu Gln Asp Ser Lys Asp Ser Thr Tyr Ser Leu
    275                 280                 285

Ser Ser Thr Leu Thr Leu Ser Lys Ala Asp Tyr Glu Lys His Lys Val
290                 295                 300

Tyr Ala Cys Glu Val Thr His Gln Gly Leu Ser Ser Pro Val Thr Lys
305                 310                 315                 320

Ser Phe Asn Arg Gly Glu Cys
            325

<210> SEQ ID NO 102
<211> LENGTH: 347
<212> TYPE: PRT
<213> ORGANISM: Artificial Sequence
<220> FEATURE:
<223> OTHER INFORMATION: H5L7 Heavy chain

<400> SEQUENCE: 102

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Leu Val Gln Pro Gly Gly Ser Leu Arg Leu Ser Cys Ala Gly Ser
    130                 135                 140

Gly Phe Thr Phe Ser Ser Tyr Val Met His Trp Leu Arg Gln Ala Pro
145                 150                 155                 160

Gly Lys Gly Leu Glu Trp Val Ser Val Ile Gly Thr Gly Gly Val Thr
                165                 170                 175

His Tyr Ala Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Trp Gly Tyr Tyr Gly Ser Gly Ser
    210                 215                 220

Tyr Glu Asn Asp Ala Phe Asp Ile Trp Gly Gln Gly Thr Met Val Thr
225                 230                 235                 240

Val Ser Ser Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270
```

```
Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Glu Pro Lys Cys Glu Phe
            340                 345

<210> SEQ ID NO 103
<211> LENGTH: 325
<212> TYPE: PRT
<213> ORGANISM: Artificial Sequence
<220> FEATURE:
<223> OTHER INFORMATION: H5L8 Light chain

<400> SEQUENCE: 103

Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
                100                 105                 110

Asp Asp Asp Asp Lys Ser Pro Gly Thr Leu Ser Leu Ser Pro Gly Glu
            115                 120                 125

Arg Ala Thr Leu Ser Cys Arg Ala Ser Gln Ser Val Ser Ser Ser Tyr
    130                 135                 140

Leu Ala Trp Tyr Gln Gln Lys Pro Gly Gln Ala Pro Arg Leu Leu Ile
145                 150                 155                 160

Tyr Gly Ala Ser Ser Arg Ala Thr Gly Ile Pro Asp Arg Phe Ser Gly
                165                 170                 175

Ser Gly Ser Gly Thr Asp Phe Thr Leu Thr Ile Ser Arg Leu Glu Pro
            180                 185                 190

Glu Asp Phe Ala Val Tyr Tyr Cys Gln Gln Tyr Ser Ser Ser Leu Thr
    195                 200                 205

Phe Gly Gly Gly Thr Lys Val Glu Ile Lys Arg Thr Val Ala Ala Pro
210                 215                 220

Ser Val Phe Ile Phe Pro Pro Ser Asp Glu Gln Leu Lys Ser Gly Thr
225                 230                 235                 240

Ala Ser Val Val Cys Leu Leu Asn Asn Phe Tyr Pro Arg Glu Ala Lys
                245                 250                 255

Val Gln Trp Lys Val Asp Asn Ala Leu Gln Ser Gly Asn Ser Gln Glu
            260                 265                 270

Ser Val Thr Glu Gln Asp Ser Lys Asp Ser Thr Tyr Ser Leu Ser Ser
    275                 280                 285
```

Thr Leu Thr Leu Ser Lys Ala Asp Tyr Glu Lys His Lys Val Tyr Ala
    290                 295                 300

Cys Glu Val Thr His Gln Gly Leu Ser Ser Pro Val Thr Lys Ser Phe
305                 310                 315                 320

Asn Arg Gly Glu Cys
            325

<210> SEQ ID NO 104
<211> LENGTH: 347
<212> TYPE: PRT
<213> ORGANISM: Artificial Sequence
<220> FEATURE:
<223> OTHER INFORMATION: H5L8 Heavy chain

<400> SEQUENCE: 104

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Ser Ala Ser Asp Asp Asp Asp
        115                 120                 125

Lys Leu Val Gln Pro Gly Gly Ser Leu Arg Leu Ser Cys Ala Gly Ser
    130                 135                 140

Gly Phe Thr Phe Ser Ser Tyr Val Met His Trp Leu Arg Gln Ala Pro
145                 150                 155                 160

Gly Lys Gly Leu Glu Trp Val Ser Val Ile Gly Thr Gly Gly Val Thr
                165                 170                 175

His Tyr Ala Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Trp Gly Tyr Tyr Gly Ser Gly Ser
    210                 215                 220

Tyr Glu Asn Asp Ala Phe Asp Ile Trp Gly Gln Gly Thr Met Val Thr
225                 230                 235                 240

Val Ser Ser Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

```
Thr Gln Thr Tyr Ile Cys Asn Val Asn His Lys Pro Ser Asn Thr Lys
                325                 330                 335

Val Asp Lys Lys Val Glu Pro Lys Cys Glu Phe
            340                 345
```

<210> SEQ ID NO 105
<211> LENGTH: 333
<212> TYPE: PRT
<213> ORGANISM: Artificial Sequence
<220> FEATURE:
<223> OTHER INFORMATION: H6L1 Light chain

<400> SEQUENCE: 105

```
Asp Ile Val Leu Thr Gln Pro His Ser Val Ser Ala Ser Pro Gly Lys
1               5                   10                  15

Thr Val Thr Ile Ser Cys Thr Arg Ser Ser Gly Ser Val Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Asn His Arg Pro Ser Gly Val Pro Asp Arg Phe Ser
        50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Leu Thr Val Leu Gly
            100                 105                 110

Ala Ser Asp Asp Asp Lys Glu Ile Val Leu Thr Gln Ser Pro Gly
        115                 120                 125

Thr Leu Ser Leu Ser Pro Gly Glu Arg Ala Thr Leu Ser Cys Arg Ala
    130                 135                 140

Ser Gln Ser Val Ser Ser Ser Tyr Leu Ala Trp Tyr Gln Gln Lys Pro
145                 150                 155                 160

Gly Gln Ala Pro Arg Leu Leu Ile Tyr Gly Ala Ser Ser Arg Ala Thr
                165                 170                 175

Gly Ile Pro Asp Arg Phe Ser Gly Ser Gly Ser Gly Thr Asp Phe Thr
            180                 185                 190

Leu Thr Ile Ser Arg Leu Glu Pro Glu Asp Phe Ala Val Tyr Tyr Cys
        195                 200                 205

Gln Gln Tyr Ser Ser Leu Thr Phe Gly Gly Gly Thr Lys Val Glu
    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330
```

```
<210> SEQ ID NO 106
<211> LENGTH: 344
<212> TYPE: PRT
<213> ORGANISM: Artificial Sequence
<220> FEATURE:
<223> OTHER INFORMATION: H6L1 Heavy chain

<400> SEQUENCE: 106

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ser Leu Thr Asp Tyr Tyr Trp Tyr Gly Met Asp Val
            100                 105                 110

Trp Gly Gln Gly Thr Leu Val Thr Val Asp Asp Asp Lys Leu Val
        115                 120                 125

Gln Pro Gly Gly Ser Leu Arg Leu Ser Cys Ala Gly Ser Gly Phe Thr
    130                 135                 140

Phe Ser Ser Tyr Val Met His Trp Leu Arg Gln Ala Pro Gly Lys Gly
145                 150                 155                 160

Leu Glu Trp Val Ser Val Ile Gly Thr Gly Gly Val Thr His Tyr Ala
                165                 170                 175

Asp Ser Val Lys Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Arg Trp Gly Tyr Tyr Gly Ser Gly Ser Tyr Glu Asn
210                 215                 220

Asp Ala Phe Asp Ile Trp Gly Gln Gly Thr Met Val Thr Val Ser Ser
225                 230                 235                 240

Ala Ser Thr Lys Gly Pro Ser Val Phe Pro Leu Ala Pro Ser Ser Lys
                245                 250                 255

Ser Thr Ser Gly Gly Thr Ala Ala Leu Gly Cys Leu Val Lys Asp Tyr
            260                 265                 270

Phe Pro Glu Pro Val Thr Val Ser Trp Asn Ser Gly Ala Leu Thr Ser
        275                 280                 285

Gly Val His Thr Phe Pro Ala Val Leu Gln Ser Ser Gly Leu Tyr Ser
    290                 295                 300

Leu Ser Ser Val Val Thr Val Pro Ser Ser Ser Leu Gly Thr Gln Thr
305                 310                 315                 320

Tyr Ile Cys Asn Val Asn His Lys Pro Ser Asn Thr Lys Val Asp Lys
                325                 330                 335

Lys Val Glu Pro Lys Cys Glu Phe
            340

<210> SEQ ID NO 107
```

```
<211> LENGTH: 357
<212> TYPE: PRT
<213> ORGANISM: Artificial Sequence
<220> FEATURE:
<223> OTHER INFORMATION: H1L5a Heavy chain

<400> SEQUENCE: 107
```

| | | | | | | | | | | | | | | | |
|---|---|---|---|---|---|---|---|---|---|---|---|---|---|---|---|
| Gln | Val | Gln | Leu | Val | Glu | Ser | Gly | Gly | Thr | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Ser | Phe | Thr | Asp | Ala |
| | | | 20 | | | | | 25 | | | | | 30 | | |
| Trp | Met | Ser | Trp | Val | Arg | Gln | Ala | Pro | Gly | Lys | Glu | Leu | Glu | Trp | Val |
| | | 35 | | | | | 40 | | | | | 45 | | | |
| Ser | Ser | Ile | Ser | Gly | Ser | Gly | Gly | Ser | Thr | Tyr | Tyr | Ala | Gly | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ala | Ala | Ala | Ala | Ala | Ala | Ala | Ala | Ala | Ala | Ala | Ala | Ala | Ala |
| | | | 100 | | | | | 105 | | | | | 110 | | |
| Trp | Gly | Gln | Gly | Thr | Leu | Val | Thr | Val | Ser | Ala | Ser | Asp | Asp | Asp | Asp |
| | | 115 | | | | | 120 | | | | | 125 | | | |
| Lys | Glu | Val | Gln | Leu | Val | Gln | Ser | Gly | Gly | Gly | Leu | Val | Gln | Pro | Gly |
| | 130 | | | | | 135 | | | | | 140 | | | | |
| Gly | Ser | Leu | Arg | Leu | Ser | Cys | Ala | Gly | Ser | Gly | Phe | Thr | Phe | Ser | Ser |
| 145 | | | | | 150 | | | | | 155 | | | | | 160 |
| Tyr | Val | Met | His | Trp | Leu | Arg | Gln | Ala | Pro | Gly | Lys | Gly | Leu | Glu | Trp |
| | | | | 165 | | | | | 170 | | | | | 175 | |
| Val | Ser | Val | Ile | Gly | Thr | Gly | Gly | Val | Thr | His | Tyr | Ala | Asp | Ser | Val |
| | | | 180 | | | | | 185 | | | | | 190 | | |
| Lys | Gly | Arg | Phe | Thr | Ile | Ser | Arg | Asp | Asn | Ala | Lys | Asn | Ser | Leu | Tyr |
| | | 195 | | | | | 200 | | | | | 205 | | | |
| Leu | Gln | Met | Asn | Ser | Leu | Arg | Ala | Glu | Asp | Thr | Ala | Val | Tyr | Tyr | Cys |
| | 210 | | | | | 215 | | | | | 220 | | | | |
| Ala | Arg | Trp | Gly | Tyr | Tyr | Gly | Ser | Gly | Ser | Tyr | Glu | Asn | Asp | Ala | Phe |
| 225 | | | | | 230 | | | | | 235 | | | | | 240 |
| Asp | Ile | Trp | Gly | Gln | Gly | Thr | Met | Val | Thr | Val | Ser | Ser | Ala | Ser | Thr |
| | | | | 245 | | | | | 250 | | | | | 255 | |
| Lys | Gly | Pro | Ser | Val | Phe | Pro | Leu | Ala | Pro | Ser | Ser | Lys | Ser | Thr | Ser |
| | | | 260 | | | | | 265 | | | | | 270 | | |
| Gly | Gly | Thr | Ala | Ala | Leu | Gly | Cys | Leu | Val | Lys | Asp | Tyr | Phe | Pro | Glu |
| | | 275 | | | | | 280 | | | | | 285 | | | |
| Pro | Val | Thr | Val | Ser | Trp | Asn | Ser | Gly | Ala | Leu | Thr | Ser | Gly | Val | His |
| | 290 | | | | | 295 | | | | | 300 | | | | |
| Thr | Phe | Pro | Ala | Val | Leu | Gln | Ser | Ser | Gly | Leu | Tyr | Ser | Leu | Ser | Ser |
| 305 | | | | | 310 | | | | | 315 | | | | | 320 |
| Val | Val | Thr | Val | Pro | Ser | Ser | Ser | Leu | Gly | Thr | Gln | Thr | Tyr | Ile | Cys |
| | | | | 325 | | | | | 330 | | | | | 335 | |
| Asn | Val | Asn | His | Lys | Pro | Ser | Asn | Thr | Lys | Val | Asp | Lys | Lys | Val | Glu |
| | | | 340 | | | | | 345 | | | | | 350 | | |
| Pro | Lys | Cys | Glu | Phe | | | | | | | | | | | |
| | | | 355 | | | | | | | | | | | | |

```
<210> SEQ ID NO 108
```

```
<211> LENGTH: 357
<212> TYPE: PRT
<213> ORGANISM: Artificial Sequence
<220> FEATURE:
<223> OTHER INFORMATION: H1L5a Heavy chain

<400> SEQUENCE: 108

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Ser Ala Ser Asp Asp Asp Asp
        115                 120                 125

Lys Glu Val Gln Leu Val Gln Ser Gly Gly Gly Leu Val Gln Pro Gly
    130                 135                 140

Gly Ser Leu Arg Leu Ser Cys Ala Gly Ser Gly Phe Thr Phe Ser Ser
145                 150                 155                 160

Tyr Val Met His Trp Leu Arg Gln Ala Pro Gly Lys Gly Leu Glu Trp
                165                 170                 175

Val Ser Val Ile Gly Thr Gly Gly Val Thr His Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Trp Gly Tyr Tyr Gly Ser Gly Ser Tyr Glu Asn Asp Ala Phe
225                 230                 235                 240

Asp Ile Trp Gly Gln Gly Thr Met Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Cys Glu Phe
        355

<210> SEQ ID NO 109
```

<211> LENGTH: 354
<212> TYPE: PRT
<213> ORGANISM: Artificial Sequence
<220> FEATURE:
<223> OTHER INFORMATION: H2L1a Heavy chain

<400> SEQUENCE: 109

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe
```

<210> SEQ ID NO 110
<211> LENGTH: 354

<212> TYPE: PRT
<213> ORGANISM: Artificial Sequence
<220> FEATURE:
<223> OTHER INFORMATION: H2L1a Heavy chain

<400> SEQUENCE: 110

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe

<210> SEQ ID NO 111
<211> LENGTH: 354
<212> TYPE: PRT

<213> ORGANISM: Artificial Sequence
<220> FEATURE:
<223> OTHER INFORMATION: H2L2a Heavy chain

<400> SEQUENCE: 111

| | | | | | | | | | | | | | | |
|---|---|---|---|---|---|---|---|---|---|---|---|---|---|---|
| Gln | Val | Gln | Leu | Val | Glu | Ser | Gly | Gly | Thr | Leu | Val | Gln | Pro | Gly | Gly |
| 1 | | | | 5 | | | | | 10 | | | | | 15 | |

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe

<210> SEQ ID NO 112
<211> LENGTH: 354
<212> TYPE: PRT
<213> ORGANISM: Artificial Sequence
<220> FEATURE:
<223> OTHER INFORMATION: H2L2a Heavy chain

<400> SEQUENCE: 112

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe

<210> SEQ ID NO 113
<211> LENGTH: 354
<212> TYPE: PRT
<213> ORGANISM: Artificial Sequence
<220> FEATURE:

<223> OTHER INFORMATION: H2L4a Heavy chain

<400> SEQUENCE: 113

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
    130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe
```

<210> SEQ ID NO 114
<211> LENGTH: 354
<212> TYPE: PRT
<213> ORGANISM: Artificial Sequence
<220> FEATURE:
<223> OTHER INFORMATION: H2L4a Heavy chain

```
<400> SEQUENCE: 114

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe

<210> SEQ ID NO 115
<211> LENGTH: 354
<212> TYPE: PRT
<213> ORGANISM: Artificial Sequence
<220> FEATURE:
<223> OTHER INFORMATION: H2L5a Heavy chain
```

<400> SEQUENCE: 115

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Trp
    210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ala Ser Thr Lys Gly Pro
                245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
            340                 345                 350

Glu Phe

<210> SEQ ID NO 116
<211> LENGTH: 354
<212> TYPE: PRT
<213> ORGANISM: Artificial Sequence
<220> FEATURE:
<223> OTHER INFORMATION: H2L5a Heavy chain

<400> SEQUENCE: 116

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
        35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
        115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Tyr Val Met
145                 150                 155                 160

His Trp Leu Arg Gln Ala Pro Gly Lys Gly Leu Glu Trp Val Ser Val
            165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Arg Trp
210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
            245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
            290                 295                 300

Ala Val Leu Gln Ser Ser Gly Leu Tyr Ser Leu Ser Ser Val Val Thr
305                 310                 315                 320

Val Pro Ser Ser Leu Gly Thr Gln Thr Tyr Ile Cys Asn Val Asn
            325                 330                 335

His Lys Pro Ser Asn Thr Lys Val Asp Lys Lys Val Glu Pro Lys Cys
            340                 345                 350

Glu Phe

<210> SEQ ID NO 117
<211> LENGTH: 354
<212> TYPE: PRT
<213> ORGANISM: Artificial Sequence
<220> FEATURE:
<223> OTHER INFORMATION: H2L7a Heavy chain

<400> SEQUENCE: 117
```

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Ser Phe Thr Asp Ala
            20                  25                  30

Trp Met Ser Trp Val Arg Gln Ala Pro Gly Lys Glu Leu Glu Trp Val
            35                  40                  45

Ser Ser Ile Ser Gly Ser Gly Gly Ser Thr Tyr Tyr Ala Gly Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ala Ala Ala Ala Ala Ala Ala Ala Ala Ala Ala Ala Ala Ala
            100                 105                 110

Trp Gly Gln Gly Thr Leu Val Thr Val Asp Asp Asp Lys Glu Val
            115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
            165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Arg Trp
210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
            245                 250                 255

Ser Val Phe Pro Leu Ala Pro Ser Ser Lys Ser Thr Ser Gly Gly Thr
            260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
            325                 330                 335

His Lys Pro Ser Asn Thr Lys Val Asp Lys Lys Val Glu Pro Lys Cys
            340                 345                 350

Glu Phe
```

<210> SEQ ID NO 118
<211> LENGTH: 354
<212> TYPE: PRT
<213> ORGANISM: Artificial Sequence
<220> FEATURE:
<223> OTHER INFORMATION: H2L7a Heavy chain

<400> SEQUENCE: 118

```
Gln Val Gln Leu Val Glu Ser Gly Gly Thr Leu Val Gln Pro Gly Gly
```

```
            1               5                  10                 15
        Ser Leu Arg Leu Ser Cys Ala Ala Ser Gly Phe Ser Phe Thr Asp Ala
                    20                  25                  30

Trp Met Ser Trp Val Arg Gln Ala Pro Gly Lys Glu Leu Glu Trp Val
                    35                  40                  45

Ser Ser Ile Ser Gly Ser Gly Gly Ser Thr Tyr Tyr Ala Gly Ser Val
                    50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                            85                  90                  95

Ala Arg Ala Ala Ala Ala Ala Ala Ala Ala Ala Ala Ala Ala Ala Ala
                        100                 105                 110

Trp Gly Gln Gly Thr Leu Val Thr Val Asp Asp Asp Lys Glu Val
                        115                 120                 125

Gln Leu Val Gln Ser Gly Gly Gly Leu Val Gln Pro Gly Gly Ser Leu
                    130                 135                 140

Arg Leu Ser Cys Ala Gly Ser Gly Phe Thr Phe Ser Ser Tyr Val Met
        145                 150                 155                 160

His Trp Leu Arg Gln Ala Pro Gly Lys Gly Leu Glu Trp Val Ser Val
                            165                 170                 175

Ile Gly Thr Gly Gly Val Thr His Tyr Ala Asp Ser Val Lys Gly Arg
                        180                 185                 190

Phe Thr Ile Ser Arg Asp Asn Ala Lys Asn Ser Leu Tyr Leu Gln Met
                        195                 200                 205

Asn Ser Leu Arg Ala Glu Asp Thr Ala Val Tyr Tyr Cys Ala Arg Trp
                    210                 215                 220

Gly Tyr Tyr Gly Ser Gly Ser Tyr Glu Asn Asp Ala Phe Asp Ile Trp
        225                 230                 235                 240

Gly Gln Gly Thr Met Val Thr Val Ser Ser Ala Ser Thr Lys Gly Pro
                        245                 250                 255

Ser Val Phe Pro Leu Ala Pro Ser Ser Lys Ser Thr Ser Gly Gly Thr
                        260                 265                 270

Ala Ala Leu Gly Cys Leu Val Lys Asp Tyr Phe Pro Glu Pro Val Thr
                    275                 280                 285

Val Ser Trp Asn Ser Gly Ala Leu Thr Ser Gly Val His Thr Phe Pro
                    290                 295                 300

Ala Val Leu Gln Ser Ser Gly Leu Tyr Ser Leu Ser Ser Val Val Thr
        305                 310                 315                 320

Val Pro Ser Ser Ser Leu Gly Thr Gln Thr Tyr Ile Cys Asn Val Asn
                        325                 330                 335

His Lys Pro Ser Asn Thr Lys Val Asp Lys Lys Val Glu Pro Lys Cys
                        340                 345                 350

Glu Phe

<210> SEQ ID NO 119
<211> LENGTH: 354
<212> TYPE: PRT
<213> ORGANISM: Artificial Sequence
<220> FEATURE:
<223> OTHER INFORMATION: H2L8a Heavy chain

<400> SEQUENCE: 119

Gln Val Gln Leu Val Glu Ser Gly Gly Thr Leu Val Gln Pro Gly Gly
        1               5                   10                  15
```

```
Ser Leu Arg Leu Ser Cys Ala Ala Ser Gly Phe Ser Phe Thr Asp Ala
         20                  25                  30

Trp Met Ser Trp Val Arg Gln Ala Pro Gly Lys Glu Leu Glu Trp Val
     35                  40                  45

Ser Ser Ile Ser Gly Ser Gly Gly Ser Thr Tyr Tyr Ala Gly Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Ala Ala Ala Ala Ala Ala Ala Ala Ala Ala Ala Ala
                100                 105                 110

Trp Gly Gln Gly Thr Leu Val Thr Val Asp Asp Asp Lys Glu Val
            115                 120                 125

Gln Leu Val Gln Ser Gly Gly Gly Leu Val Gln Pro Gly Gly Ser Leu
130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Arg Trp
210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
            245                 250                 255

Ser Val Phe Pro Leu Ala Pro Ser Ser Lys Ser Thr Ser Gly Gly Thr
                260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
                340                 345                 350

Glu Phe

<210> SEQ ID NO 120
<211> LENGTH: 354
<212> TYPE: PRT
<213> ORGANISM: Artificial Sequence
<220> FEATURE:
<223> OTHER INFORMATION: H2L8a Heavy chain

<400> SEQUENCE: 120

Gln Val Gln Leu Val Glu Ser Gly Gly Thr Leu Val Gln Pro Gly Gly
1               5                   10                  15
```

```
Ser Leu Arg Leu Ser Cys Ala Ala Ser Gly Phe Ser Phe Thr Asp Ala
         20                  25                  30

Trp Met Ser Trp Val Arg Gln Ala Pro Gly Lys Glu Leu Glu Trp Val
         35                  40                  45

Ser Ser Ile Ser Gly Ser Gly Gly Ser Thr Tyr Tyr Ala Gly Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Ala Ala Ala Ala Ala Ala Ala Ala Ala Ala Ala Ala
                100                 105                 110

Trp Gly Gln Gly Thr Leu Val Thr Val Asp Asp Asp Lys Glu Val
         115                 120                 125

Gln Leu Val Gln Ser Gly Gly Gly Leu Val Gln Pro Gly Gly Ser Leu
         130                 135                 140

Arg Leu Ser Cys Ala Gly Ser Gly Phe Thr Phe Ser Ser Tyr Val Met
145                 150                 155                 160

His Trp Leu Arg Gln Ala Pro Gly Lys Gly Leu Glu Trp Val Ser Val
                165                 170                 175

Ile Gly Thr Gly Gly Val Thr His Tyr Ala Asp Ser Val Lys Gly Arg
                180                 185                 190

Phe Thr Ile Ser Arg Asp Asn Ala Lys Asn Ser Leu Tyr Leu Gln Met
                195                 200                 205

Asn Ser Leu Arg Ala Glu Asp Thr Ala Val Tyr Tyr Cys Ala Arg Trp
                210                 215                 220

Gly Tyr Tyr Gly Ser Gly Ser Tyr Glu Asn Asp Ala Phe Asp Ile Trp
225                 230                 235                 240

Gly Gln Gly Thr Met Val Thr Val Ser Ser Ala Ser Thr Lys Gly Pro
                245                 250                 255

Ser Val Phe Pro Leu Ala Pro Ser Ser Lys Ser Thr Ser Gly Gly Thr
                260                 265                 270

Ala Ala Leu Gly Cys Leu Val Lys Asp Tyr Phe Pro Glu Pro Val Thr
                275                 280                 285

Val Ser Trp Asn Ser Gly Ala Leu Thr Ser Gly Val His Thr Phe Pro
                290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Cys
                340                 345                 350

Glu Phe
```